US009493776B2

(12) United States Patent
Kumon et al.

(10) Patent No.: US 9,493,776 B2
(45) Date of Patent: *Nov. 15, 2016

(54) SYSTEM FOR INCREASING GENE EXPRESSION AND VECTOR COMPRISING THE SYSTEM

(75) Inventors: Hiromi Kumon, Okayama (JP);
Nam-Ho Huh, Okayama (JP);
Masakiyo Sakaguchi, Okayama (JP);
Masami Watanabe, Okayama (JP)

(73) Assignees: National University Corporation Okayama University, Okayama (JP);
Momotaro-Gene Inc., Okayama (JP)

(*) Notice: Subject to any disclaimer, the term of this patent is extended or adjusted under 35 U.S.C. 154(b) by 720 days.

This patent is subject to a terminal disclaimer.

(21) Appl. No.: 13/510,719

(22) PCT Filed: Nov. 19, 2010

(86) PCT No.: PCT/JP2010/071196
§ 371 (c)(1),
(2), (4) Date: Aug. 6, 2012

(87) PCT Pub. No.: WO2011/062298
PCT Pub. Date: May 26, 2011

(65) Prior Publication Data
US 2012/0309050 A1 Dec. 6, 2012

(30) Foreign Application Priority Data
Nov. 19, 2009 (JP) ................................ 2009-264299

(51) Int. Cl.
*C12N 15/86* (2006.01)
*A61K 48/00* (2006.01)
*A61K 38/00* (2006.01)
*C12N 15/67* (2006.01)
*C12N 15/85* (2006.01)
*A61K 38/17* (2006.01)
*C12P 21/02* (2006.01)

(52) U.S. Cl.
CPC .......... *C12N 15/67* (2013.01); *A61K 38/1761* (2013.01); *C12N 15/85* (2013.01); *C12P 21/02* (2013.01); *C12N 2799/025* (2013.01); *C12N 2830/00* (2013.01); *C12N 2830/50* (2013.01)

(58) Field of Classification Search
None
See application file for complete search history.

(56) References Cited

U.S. PATENT DOCUMENTS

| 5,849,522 | A | 12/1998 | Fleckenstein et al. |
| 6,218,140 | B1 | 4/2001 | Fleckenstein et al. |
| 6,777,203 | B1 | 8/2004 | Morin et al. |
| 2003/0138954 | A1 | 7/2003 | Trono et al. |
| 2005/0059146 | A1 | 3/2005 | Otto et al. |

FOREIGN PATENT DOCUMENTS

| JP | 2007-502608 | | 2/2007 |
| RU | 2305708 | C2 | 10/2005 |
| UZ | 3319 | C | 4/2007 |
| WO | WO 98/56923 | A1 | 12/1998 |
| WO | WO-2008/091276 | A2 | 7/2008 |

OTHER PUBLICATIONS

Hull et al., "RU5 of Mason-Pfizer Monkey Virus 5' Long Terminal Repeat Enhances Cytoplasmic Expression of Human Immunodeficiency Virus Type 1 gag-pol and Nonviral Reporter RNA," Journal of Virology, Oct. 2002, 76(20):10211-10218.
CN Application No. 201080061897.9 Office Action and English Translation Issued Mar. 12, 2013.
Dennis Frisby et al., "Analysis of the Upstream Activiating Sequence and Site of Carbon and Nitrogen Source Repression in the Promoter of an Early-Induced Sporulation Gene of Bacillus subtilis", Journal of Bacteriology, Dec. 1991, vol. 173, No. 23., pp. 7557-7564.
EP Application No. 10831684.5 Search Report Issued Apr. 5, 2013.
N. Silvestre et al., "Characterization of upstream activating sequences involved in activation and regulation of pho4 expression in Schizosaccharomyces pombe", Molecular and General Genetics, vol. 253, No. 4, 1997, pp. 428-438.
Takemoto et al., "The promoter of the *endo A* cytokeratin gene is activated by a 3' downstream enhancer," Nucleic Acids Research, 1991, 19(10):2761-2765.
International Search Report PCT/JP2010/071196 dated Mar. 8, 2011.
James P.F. Latham et al., "Prostate-specific Antigen Promoter/Enhancer Driven Gene Therapy for Prostate Cancer: Construction and Testing of a Tissue-specific Adenovirus Vector", Cancer Research 60, Jan. 15, 2000, pp. 334-341.
Joe Attal et al., "The optimal use of IRES (internal ribosome entry site) in expression vectors", Genetic Analysis: Biomolecular Engineering, 15 (1999), 161-165.
Joe Attal et al., "The stimulation of gene expression by the R region from HTLV-1 and BLV", Journal of Biotechnology, 77 (2000) 179-189.
Julie M. Cherrington et al., "Human Cytomegalovirus ie1 Transactivates the α Promoter-Enhancer via an 18-Base-Pair Repeat Element", Journal of Virology, Mar. 1989, vol. 63, No. 3, pp. 1435-1440.
Michael Boshart et al., "A Very Strong Enhancer Is Located Upstream of an Immediate Early Gene of Human Cytomegalovirus", Cell, vol. 41, 521-530, Jun. 1985.
Sung Jin Kim et al., "Preferentially enhanced gene expression from a synthetic human telomerase reverse transcriptase promoter in human cancer cells", Oncology Reports 16: 975-979, 2006.

(Continued)

*Primary Examiner* — Catherine S Hibbert
*Assistant Examiner* — Channing S Mahatan
(74) *Attorney, Agent, or Firm* — Foley & Lardner LLP

(57) ABSTRACT

An object of the present invention is to provide a method for increasing the expression of foreign genes, in particular, using a promoter, an enhancer, and the like, and an expression cassette containing a promoter, an enhancer, and the like, by which gene expression can be increased. The purpose is achieved with the use of the gene expression cassette comprising a DNA construct containing a gene to be expressed and a poly A addition sequence that are located downstream of a $1^{st}$ promoter, and further comprising an enhancer or a $2^{nd}$ promoter ligated downstream of the DNA construct.

16 Claims, 75 Drawing Sheets

(56) References Cited

OTHER PUBLICATIONS

Yutaka Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, Jan. 1988, vol. 8, No. 1, pp. 466-472.

Zhi-Li Xu et al., "Optimization of transcriptional regulatory elements for constructing plasmid vectors", Gene 272 (2001) 149-156.

Technical Manual pCAT3 Reporter Vectors [online], Promega, 2008, http://www.promega.com.cn/techserve/tbs/TM001-310/tm036,pdf, retrieved on Aug. 28, 2014.

Sadeghi et al., "Transcriptionally Targeted Adenovirus Vectors," Current Gene Therapy, 2005, 5:411-427.

Tanimoto et al., "REIC/Dkk-3 as a potential gene therapeutic agent against human testicular cancer," International Journal of Molecular Medicine, 2007, 19(3):363-368.

China Application No. 201080061897.9, Office Action issued Nov. 27, 2013.

China Application No. 201080061897.9, Search Report issued Nov. 27, 2013.

Notice of Allowance dated Dec. 15, 2015, in Russian Application No. 2012125253, 8 pages. (Not in English).

Fig. 5-2
A
FuGENE-HD alone
(Day 5)
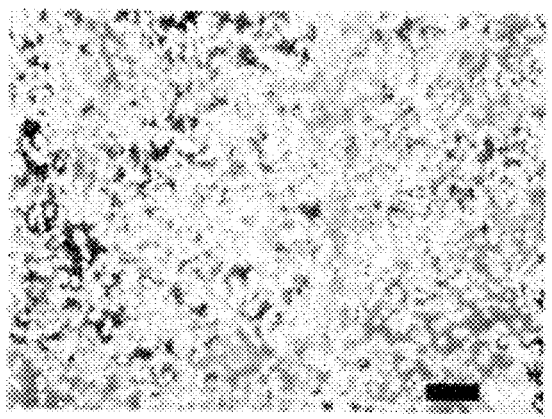
Bar = 200 μm
B
Control gene (IRES)
+ FuGENE-HD
(Day 5)
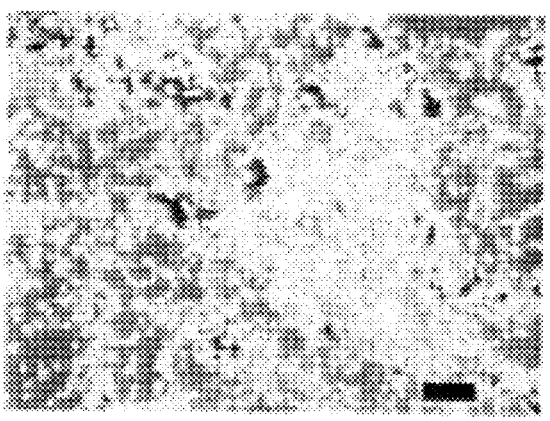
C
N78-REIC gene
+ FuGENE-HD
(Day 5)
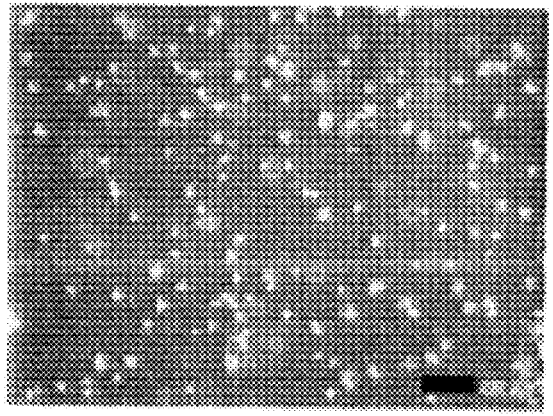

Fig. 8 Construct No.2

Construct No.3

Fig. 10 Construct No.4

Fig. 11 Construct No.5

Fig. 12 Construct No.6

Construct No.7

Construct No. 8

Construct No.9

Fig. 16 Construct No.10

Construct No.11

Construct No. 12

Construct No. 13

Construct No. 14

Fig. 22-1

Full nucleotide sequence of pDNR-1r Donor vector a) Ampicillin resistance
b) Multicloning site in bold character style `GTCGAC`: SalI, `GCGCGC`: BssHII GCGGCCGCATAACTTCGTATAGCATACATTATACGAAGTTATCAGTCGAC Insert a gene to be expressed.
GCGCGCGGGCCCAGTAGGTAAGTGAACATGGTCATAGCTGTTTCCTAGGAGATCCTGGTCAT
GACTAGTGCTTGGATTCTCACCAATAAAAAACGCCCGGCGGCAACCGAGCGTTCTGAACAAA
TCCAGATGGAGTTCTGAGGTCATTACTGGATCTATCAACAGGAGTCCAAGCGAGCTCGATAT
CAAATTACGCCCCGCCCTGCCACTCATCGCAGTACTGTTGTAATTCATTAAGCATTCTGCCG
ACATGGAAGCCATCACAAACGGCATGATGAACCTGAATCGCCAGCGGCATCAGCACCTTGTC
GCCTTGCGTATAATATTTGCCCATGGTGAAAACGGGGGCGAAGAAGTTGTCCATATTGGCCA
CGTTTAAATCAAAACTGGTGAAACTCACCCAGGGATTGGCTGAGACGAAAAACATATTCTCA
ATAAACCCTTTAGGGAAATAGGCCAGGTTTTCACCGTAACACGCCACATCTTGCGAATATAT
GTGTAGAAACTGCCGGAAATCGTCGTGGTATTCACTCCAGAGCGATGAAAACGTTTCAGTTT
GCTCATGGAAAACGGTGTAACAAGGGTGAACACTATCCCATATCACCAGCTCACCGTCTTTC
ATTGCCATACGAAATTCCGGATGAGCATTCATCAGGCGGGCAAGAATGTGAATAAAGGCCGG
ATAAAACTTGTGCTTATTTTTCTTTACGGTCTTTAAAAGGCCGTAATATCCAGCTGAACGG
TCTGGTTATAGGTACATTGTGTGATTAAAAAGGCAACTTTATGCCCATGCAACAGAAACTAT
AAAAAATACAGAGAATGAAAAGAAACAGATAGATTTTTTAGTTCTTTAGGCCCGTAGTCTGC
AAATCCTTTTATGATTTCTATCAAACAAAAGAGGAAAATAGACCAGTTGCAATCCAAACGA
GAGTCTAATAGAATGAGGTCGAAAAGTAAATCGCGCGGGTTTGTTACTGATAAAGCAGGCAA
GACCTAAAATGTGTAAAGGGCAAAGTGTATACTTTTGGCGTCACCCCTTACATATTTTAGGTC
TTTTTTTATTGTGCGTAACTAACTTGCCATCTTCAAACAGGAGGGCTGGAAGAAGCAGACCG
CTAACACAGTACATAAAAAGGAGACATGAACGATGAACATCAAAAAGTTTGCAAAACAAGC
AACAGTATTAACCTTTACTACCGCACTGCTGGCAGGAGGCGCAACTCAAGCTTTTGCGAAAG
AAACGAACCAAAAGCCATATAAGGAAACATACGGCATTTCCCATATTACACGCCATGATATG
CTGCAAATCCCTGAACAGCAAAAAATGAAAATATCAAGTTCCTGAGTTCGATTCGTCCAC
AATTAAAAATATCTCTTCTGCAAAAGGCCTGGACGTTTGGGACAGCTGGCCATTACAAAACG
CTGACGGCACTGTCGCAAACTATCACGGCTACCACATCGTCTTTGCATTAGCCGGAGATCCT
AAAAATGCGGATGAACACATCGATTACATGTTCTATCAAAAAGTCGGCGAAACTTCTATTGA
CAGCTGGAAAAACGCTGGCCGCGTCTTTAAAGACAGCGACAAATTCGATGCAAATGATTCTA
TCCTAAAAGACCAAACACAAGAATGGTCAGGTTCAGCCACATTTACATCTGACGGAAAAATC
CGTTTATTCTACACTGATTTCTCCGGTAAACATTACGGCAAACAAACACTGACAACTGCACA
AGTTAACGTATCAGCATCAGACAGCTCTTTGAACATCAACGGTGTAGAGGATTATAAATCAA
TCTTTGACGGTGACGGAAAAACGTATCAAAATGTACAGCAGTTCATCGATGAAGGCAACTAC
AGCTCAGGCGACAACCATACGCTGAGAGATCCTCACTACGTAGAAGATAAAGGCCACAAATA
CTTAGTATTTGAAGCAAACACTGGAACTGAAGATGGCTACCAAGGCGAAGAATCTTTATTTA

Fig. 22-2

```
ACAAAGCATACTATGGCAAAAGCACATCATTCTTCCGTCAAGAAAGTCAAAAACTTCTGCAA
AGCGATAAAAAACGCACGGCTGAGTTAGCAAACGGCGCTCTCGGTATGATTGAGCTAAACGA
TGATTACACACTGAAAAAAGTGATGAAACCGCTGATTGCATCTAACACAGTAACAGATGAAA
TTGAACGCGCGAACGTCTTTAAAATGAACGGCAAATGGTACCTGTTCACTGACTCCCGCGGA
TCAAAAATGACGATTGACGGCATTACGTCTAACGATATTACATGCTTGGTTATGTTTCTAA
TTCTTTAACTGGCCCATACAAGCCGCTGAACAAAACTGGCCTTGTGTTAAAAATGGATCTTG
ATCCTAACGATGTAACCTTTACTTACTCACACTTCGCTGTACCTCAAGCGAAAGGAAACAAT
GTCGTGATTACAAGCTATATGACAAACAGAGGATTCTACGCAGACAAACAATCAACGTTTGC
GCCTAGCTTCCTGCTGAACATCAAAGGCAAGAAAACATCTGTTGTCAAAGACAGCATCCTTG
AACAAGGACAATTAACAGTTAACAAATAAAAACGCAAAAGAAAATGCCGATATCCTATTGGC
ATTGACGTCAGGTGGCACTTTTCGGGGAAATGTGCGCGGAACCCCTATTTGTTTATTTTCT
AAATACATTCAAATATGTATCCGCTCATGAGACAATAACCCTGATAAATGCTTCAATAATAT
TGAAAAAGGAAGAGTATGAGTATTCAACATTTCCGTGTCGCCCTTATTCCCTTTTTTGCGGC
ATTTTGCCTTCCTGTTTTTGCTCACCCAGAAACGCTGGTGAAAGTAAAAGATGCTGAAGATC
AGTTGGGTGCACGAGTGGGTTACATCGAACTGGATCTCAACAGCGGTAAGATCCTTGAGAGT
TTTCGCCCCGAAGAACGTTTTCCAATGATGAGCACTTTTAAAGTTCTGCTATGTGGCGCGGT
ATTATCCCGTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAGTAAGAGAA
TTATGCAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGCCT
GTAGCAATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAGC
ATTGGTAACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTT
TGTTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGTAG
CACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATACC
TACAGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTT
TGCTGGCCTTTTGCTCACATGTTCTTTCCTGCGTTATCCCCTGATTCTGTGGATAACCGTAT
TACCGCCTTACGCGTGTAAAACGACGGCCAGTAGATCTGTAATACGACTCACTATAGGGCGC
TAGCTGCTCGCCGCAGCCGAACGACCGAGCGCAGCGAGTCAGTGAGCGAGGAA
```

Fig. 23

Full nucleotide sequence of pIDT-SMART vector a) Kanamycin resistance
b) Multicloning site in bold character style `GATATC`: EcoRV

```
GGGCTGTGTGCACGAACCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATT
AGCAGAGCGAGGTATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCTCGGAAAAAGAGT
TGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATTTTCTACCGAAGAAAG
GCCCACCCGTGAAGGTGAGCCAGTGAGTTGATTGCAGTCCAGTTACGCTGGAGTCTGACGCT
CGTCCTGAATGTGTAAAACGACGGCCAGTTTATCTAGTCAGCTTGATTCTAGCTGATCGTGG
ACCGGAAGGTGAGCCAGTGAGTTGATTGCAGTCCAGTTACGCTGGAGTCTGAGGCTCGTCCT
GAATGATATACGCGTCGGAGGGTTGCGTTTGAGACGGGCGACAGAT insert a gene to be
expressed.
ATCAGTTCTGGACGAGCGAGCTGTCGTCCGGCGGCCGCGATCTTACGGCATTATACGTATGA
TCGGTCCACGATCAGCTAGATTATCTAGTCAGCTTGATGTCATAGCTGTTTCCTGAGGCTCA
ATACTGACCATTTAAATCATACCTGACCTCCATAGCAGAAAGTCAAAAGCCTCCGACCGGAG
GCTTTTGACTTGATCGGCACGTAAGAGGTTCCAACTTTCACCATAATGAAATAAGATCACTA
CCGGGCGTATTTTTTGAGTTATCGAGATTTTCAGGAGCTAAGGAAGCTAAAATGAGCCATAT
TCAACGGGAAACGTCTTGCTTGAAGCCGCGATTAAATTCCAACATGGATGCTGATTTATATG
GGTATAAATGGGCTCGCGATAATGTCGGGCAATCAGGTGCGACAATCTATCGATTGTATGG
AAGCCCGATGCGCCAGAGTTGTTTCTGAAACATGGCAAAGGTAGCGTTGCCAATGATGTTAC
AGATGAGATGGTCAGGCTAAACTGGCTGACGGAATTTATGCCTCTTCCGACCATCAAGCATT
TTATCCGTACTCCTGATGATGCATGGTTACTCACCACTGCGATCCCAGGGAAAACAGCATTC
CAGGTATTAGAAGAATATCCTGATTCAGGTGAAAATATTGTTGATGCGCTGGCAGTGTTCCT
GCGCCGGTTGCATTCGATTCCTGTTTGTAATTGTCCTTTTAACGGCGATCGCGTATTTCGTC
TCGCTCAGGCGCAATCACGAATGAATAACGGTTTGGTTGGTGCGAGTGATTTTGATGACGAG
CGTAATGGCTGGCCTGTTGAACAAGTCTGGAAAGAAATGCATAAACTCTTGCCATTCTCACC
GGATTCAGTCGTCACTCATGGTGATTTCTCACTTGATAACCTTATTTTTGACGAGGGGAAAT
TAATAGGTTGTATTGATGTTGGACGAGTCGGAATCGCAGACCGATACCAGGATCTTGCCATC
CTATGGAACTGCCTCGGTGAGTTTTCTCCTTCATTACAGAAACGGCTTTTTCAAAAATATGG
TATTGATAATCCTGATATGAATAAATTGCAGTTTCACTTGATGCTCGATGAGTTTTTCTAAT
GAGGACCTAAATGTAATCACCTGGCTCACCTTCGGGTGGGCCTTTCTGCGTTGCTGGCGTTT
TTCCATAGGCTCCGCCCCCTGACGAGCATCACAAAAATCGATGCTCAAGTCAGAGGTGGCG
AAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCT
```

Fig. 24

Nucleotide sequence of CMVi promoter (hCMV + intron promoter) region

```
tcgcgttacataacttacggtaaatggcccgcctggctgaccgcccaacgacccccgcca
ttgacgtcaataatgacgtatgttcccatagtaacgccaatagggactttccattgacgtca
atgggtggagtatttacggtaaactgcccacttggcagtacatcaagtgtatcatatgccaa
gtacgccccctattgacgtcaatgacggtaaatggcccgcctggcattatgcccagtacatg
accttatgggactttcctacttggcagtacatctacgtattagtcatcgctattaccatggt
gatgcggttttggcagtacatcaatgggcgtggatagcggtttgactcacggggatttccaa
gtctccaccccattgacgtcaatgggagtttgttttggcaccaaaatcaacgggactttcca
aaatgtcgtaacaactccgccccattgacgcaaatgggcggtaggcgtgtacggtgggaggt
ctatataagcagagctcgtttagtgaaccgtcagatcgcctggagacgccatccacgctgtt
ttgacctccatagaagacaccgggaccgatccagcctccgcggccgggaacggtgcattgga
acgcggattccccgtgccaagagtgacgtaagtacgcctatagactctataggcacaccc
tttggctcttatgcatgaattaatacgactcactatagggagacagactgttcctttcctgg
gtcttttctg
```

Fig. 25

Nucleotide sequence of BGH polyA (3 x stop + BGH poly A) region tgactgactgacGTTTAAACCCGCTGATCAGCCTCGACTGTGCCTTCTAGTTGCCAGCCATC
TGTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGGATGC
GGTGGGCTCTATGG

Fig. 26

Nucleotide sequence of CMV enhancer region

Tccgcgttacataacttacggtaaatggcccgcctggctgaccgcccaacgacccccgccca
ttgacgtcaataatgacgtatgttcccatagtaacgccaatagggactttccattgacgtca
atgggtggagtatttacggtaaactgcccacttggcagtacatcaagtgtatcatatgccaa
gtacgccccctattgacgtcaatgacggtaaatggcccgcctggcattatgcccagtacatg
accttatgggactttcctacttggcagtacatctacgtattagtcatcgctattaccatggt

Fig. 27

Nucleotide sequence of human β-actin promoter region gttccatgtccttatatggactcatctttgcctattgcgacacacactcagtgaacacctac
tacgcgctgcaaagagccccgcaggctgaggtgccccacctcaccactcttcctattttt
gtgtaaaaatccagcttcttgtcaccacctccaaggagggggaggaggaggaaggcaggttc
ctctaggctgagccgaatgcccctctgtggtcccacgccactgatcgctgcatgccaccac
ctgggtacacacagtctgtgattcccggagcagaacggaccctgccacccggtcttgtgtg
ctactcagtggacagacccaaggcaagaaaggtgacaaggacagggtcttcccaggctggc
tttgagttcctagcaccgccccgccccaatcctctgtggcacatggagtcttggtcccag
agtccccagcggcctccagatggtctgggaggcagttcagctgtggctgcgcatagcaga
catcaacggacggtgggcccagacccaggctgtgtagacccagcccccgccccgcagtg
cctaggtcaccactaacgcccaggccttgtcttggctgggcgtgactgttaccctcaaaa
gcaggcagctccagggtaaaggtgccctgcctgtagagccaccttccttcccagggctg
cggctgggtaggtttgtagccttcatcacgggccacctcagccactggaccgctggcccct
gccctgtcctgggagtgtggtcctgcgacttctaagtggccgcaagccacctgactcccc
aacaccacactctacctctcaagccaggtctctcccagtgaccacccagcacatttagc
tagctgagccccacagccagaggtcctcaggcctgctttcagggcagttgctctgaagtcg
gcaaggggagtgactgctggccactccatgccctccaagagctccttctgcaggagcgta
cagaacccagggcctggcaccgtgcagaccctggcccaccccacctgggcgctcagtgcc
caagagatgtccacacctaggatgtcccgcggtgggtgggggcccgagagacgggcaggcc
ggggcaggcctggccatgcggggccgaaccggcactgcccagcgtggggcgcggggcca
cggccgcgcgccccagccccggggcccagcaccccaaggcggccaacgccaaaactctccct
cctcctcttcctcaatctcgctctcgctctttttttttttcgcaaaaggagggggagaggggg
taaaaaatgctgcactgtgcggcgaagccggtgagtgagcggcgcggggccaatcagcgtg
cgccgttccgaaagttgcctttatggctcgagcggccgcggcggcgccctataaaacccag
cggcgcgacgcgccaccaccgccgagaccgcgtccgccccgcgagcacagagcctcgcctttt
gccgatccgccgccgtcca

Fig. 28

Nucleotide sequence of RU5' forward (R segment of HTLV Type 1 long terminal repeat and a portion (R-U5') of the U5 sequence ) region agcttcgagggctcgcatctctccttcacgcgcccgccgccctacctgaggccgccatcca
cgccggttgagtcgcgttctgccgcctcccgcctgtggtgcctcctgaactgcgtccgccgt
ctaggtaagtttaaagctcaggtcgagaccgggcctttgtccgggctcccttggagcctac
ctagactcagccggctctccacgctttgcctgaccctgcttgctcaactctacgtctttgtt
tcgttttctgttctgcgccgttacagatccaagccacc

Fig. 29

Nucleotide sequence of RU5' reverse (R segment of HTLV Type 1 long terminal repeat and a portion (R-U5) of the U5 sequence ) region ggtggcttggatctgtaacggcgcagaacagaaacgaaacaaagacgtagagttgagcaag
cagggtcaggcaaagcgtggagagccggctgagtctaggtaggctccaagggagcgccggac
aaaggcccggtctcgacctgagctttaaacttacctagacggcggacgcagttcaggaggca
ccacaggcgggaggcggcagaacgcgactcaaccggcgtggatggcggcctcaggtagggcg
gcgggcgcgtgaaggagagatgcgagcccctcgaagct

Fig. 30

Nucleotide sequence of 4 x CMV enhancer region gtcgacgtcgcccattgacgtcaatgggcgttacataacttacggtaaatggcccgcctgg
ctgaccgcccaacgacccccgcccattgacgtcaataatgacgtatgttcccatagtaacgc
caatagggactttccattgacgtcaatgggtggagtatttacggtaaactgcccacttggca
gtacatcaagtgtatcatatgccaagtacgccccctattgacgtcaatgacggtaaatggcc
cgcctggcattatgcccagtacatgaccttatgggactttcctacttggcagtacatctacg
tattagtcatcgctattaccatggtcccattgacgtcaatgggcgttacataacttacggt
aaatggcccgcctggctgaccgcccaacgacccccgcccattgacgtcaataatgacgtatg
ttcccatagtaacgccaatagggactttccattgacgtcaatgggtggagtatttacggtaa
actgcccacttggcagtacatcaagtgtatcatatgccaagtacgccccctattgacgtcaa
tgacggtaaatggcccgcctggcattatgcccagtacatgaccttatgggactttcctactt
ggcagtacatctacgtattagtcatcgctattaccatggtcccattgacgtcaatgggcgt
tacataacttacggtaaatggcccgcctggctgaccgcccaacgacccccgcccattgacgt
caataatgacgtatgttcccatagtaacgccaatagggactttccattgacgtcaatgggtg
gagtatttacggtaaactgcccacttggcagtacatcaagtgtatcatatgccaagtacgcc
ccctattgacgtcaatgacggtaaatggcccgcctggcattatgcccagtacatgaccttat
gggactttcctacttggcagtacatctacgtattagtcatcgctattaccatggtcccatt
gacgtcaatgggGGACTAGT

Fig. 31

Nucleotide sequence of CAG promoter region

ATTGATTATTGACTAGTTATTAATAGTAATCAATTACGGGGTCATTAGTTCATAGCCCATAT
ATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATT
GACGTCAATGGGTGGAGTATTTACGGTAAACTGCCCACTTGGCAGTACATCAAGTGTATCAT
ATGCCAAGTACGCCCCCTATTGACGTCAATGACGGTAAATGGCCCGCCTGGCATTATGCCCA
GTACATGACCTTATGGGACTTTCCTACTTGGCAGTACATCTACGTATTAGTCATCGCTATTA
CCATGGTCGAGGTGAGCCCCACGTTCTGCTTCACTCTCCCCATCTCCCCCCCTCCCCACCC
CCAATTTTGTATTTATTTATTTTTAATTATTTTGTGCAGCGATGGGGGCGGGGGGGGGGGG
CGCGCGCCAGGCGGGGCGGGGCGGGGCGAGGGGCGGGGCGGGGCGAGGCGGAGAGGTGCGGC
GGCAGCCAATCAGAGCGGCGCGCTCCGAAAGTTTCCTTTTATGGCGAGGCGGCGGCGGCGGC
GGCCCTATAAAAAGCGAAGCGCGCGGCGGGCGGGAGTCGCTGCGCGCTGCCTTCGCCCCGTG
CCCCGCTCCGCCGCCGCCTCGCGCCGCCCGCCCCGGCTCTGACTGACCGCGTTACTCCCACA
GGTGAGCGGGCGGGACGGCCCTTCTCCTCCGGGCTGTAATTAGCGCTTGGTTTAATGACGGC
TTGTTTCTTTTCTGTGGCTGCGTGAAAGCCTTGAGGGGCTCCGGGAGGGCCCTTTGTGCGGG
GGGAGCGGCTCGGGGGGTGCGTGCGTGTGTGTGCGTGGGGAGCGCCGCGTGCGGCTCCGC
GCTGCCCGGCGGCTGTGAGCGCTGCGGGCGCGGCGCGGGGCTTTGTGCGCTCCGCAGTGTGC
GCGAGGGGAGCGCGGCCGGGGGCGGTGCCCCGCGGTGCGGGGGGGCTGCGAGGGGAACAAA
GGCTGCGTGCGGGGTGTGTGCGTGGGGGGGTGAGCAGGGGGTGTGGGCGCGTCGGTCGGGCT
GCAACCCCCCTGCACCCCCCTCCCCGAGTTGCTGAGCACGGCCCGGCTTCGGGTGCGGGGC
TCCGTACGGGGCGTGGCGCGGGGCTCGCCGTGCCGGCGGGGGTGCGGCAGGTGGGGGTG
CCGGGCGGGGCGGGGCCGCCTCGGGCCGGGGAGGGCTCGGGGGAGGGGCGCGGCGGCCCCCG
GAGCGCCGGCGGCTGTCGAGGCGCGGCGAGCCGCAGCCATTGCCTTTTATGGTAATCGTGCG
AGAGGGCGCAGGGACTTCCTTTGTCCCAAATCTGTGCGGAGCCGAAATCTGGGAGGCGCCGC
CGCACCCCCTCTAGCGGGCGCGGGGCGAAGCGGTGCGGCGCCGGCAGGAAGGAAATGGGCGG
GGAGGGCCTTCGTGCGTCGCCGCGCCGCCGTCCCCTTCTCCCTCTCCAGCCTCGGGGCTGTC
CGCGGGGGGACGGCTGCCTTCGGGGGGGACGGGGCAGGGCGGGGTTCGGCTTCTGGCGTGTG
ACCGGCGGC

Fig. 32

Nucleotide sequence of 2IRES insert region

Sal I-EcoRI-BglII-KpnI-SpeI-Bip IRES-BamHI-HindIII-NheI-Myc IRES-XhoI-StuI-XbaI-BssHII

```
ACGCGTCGACGTCGGCCATACCGGAATTCCGGGGAGATCTTCCCGGGGTACCTCGAGGACT
AGTtcgacgccggccaagacagacagacagattgacctattggggtgtttcgcgagtgtga
gagggaagcgccgcggctgtattactagacctgcccttcgcctggttcgtggcgccttgtg
accccgggccctgccgcctgcaagtcgaaattgcgctgtgctcctgtgctacggcctgtgg
ctggactacctgctgctgccctactggctggcaagatcaagctctcctggtggccgcgatc
ctCGCGGATCCGCGGCCCAAGCTTGGGTTAGCTAGCccctaattccagcgagaggcagaggga
gcgagcgggcggccggctagggtggaagagccgggcgagcagagctgcgctgcgggcgtcct
gggaagggagatccggagcgaataggggcttcgcctctggcccagccctcccgctgatccc
ccagccagcggtccgcaaccctttgccgcatccacgaaactttgcccatagcagcgggcggc
actttgcactggaacttacaacacccgagcaaggacgcgactctcccgacgcgggaggcta
ttctgcccatttggggacacttccccgccgctgccaggacccgcttctctgaaaggctctcc
ttgcagctgcttagacgctggatttttttcgggtagtggaaaaccagcagcctcccgcgCCG
CTCGAGCGGAAAGGCCTTTTGCTCTAGAGCTTGCGCGCAA
```

Fig. 33

Nucleotide sequence of SV40ori-UAS-CMVi-RU5' region (1)     (2)   (3)
SalI-SV40 ori + UAS + CMVi + RU5'-EcoRI GTCGACGTCGCCCATA
aattttttgcaaaagcctt ggcctccaaaaaagcctcctcactacttctggaatagctcaga (1)
ggccgaggcggcctcggcctctgcataaataaaaaaaatta gtcagccttgggtcggagaaa
ctatcgttgctgactaattgagat cggagtactgtcctccg tgttacataacttacggtaaa (2)
tggcccgcctggctgaccgcccaacgacccccgcccattgacgtcaataatgacgtatgttc
ccatagtaacgccaatagggactttccattgacgtcaatgggtggagtatttacggtaaact
gcccacttggcagtacatcaagtgtatcatatgccaagtacgccccctattgacgtcaatga
cggtaaatggcccgcctggcattatgcccagtacatgaccttatgggactttcctacttggc
agtacatctacgtattagtcatcgctattaccatggtgatgcggttttggcagtacatcaat
gggcgtggatagcggtttgactcacggggatttccaagtctccaccccattgacgtcaatgg
gagtttgttttggcaccaaaatcaacgggactttccaaaatgtcgtaacaactccgccccat
tgacgcaaatgggcggtaggcgtgtacggtgggaggtctatataagcagagctcgtttagtg
aaccgtcagatcgcctggagacgccatccacgctgttttgacctccatagaagacaccgga
ccgatccagcctccgcggccgggaacggtgcattggaacgcggattccccgtgccaagagtg
acgtaagtaccgcctatagactctataggcacacccctttggctcttatccatcaattaata
cgactcactatagggagacagactgttcctttcctgggtctttctg gcttcgaggggctcg (3)
catctctccttcacgcgcccgccgccctacctgaggccgccatccacgccggttgagtcgcg
ttctgccgcctcccgcctgtggtgcctctgaactgcgtccgccgtctaggtaagtttaaag
ctcaggtcgagaccgggcctttgtccggcgctcccttggagcctacctagactcagccggct
ctccacgctttgcctgaccctgcttgctcaactctacgtctttgtttcgttttctgttctgc
gccgttacagatccaagccacc CCGAATTC

Fig. 34

Nucleotide sequence of 3 x stop-BGH-polyA-UAS-hTERT enhancer + SV40 enhancer + CMV enhancer region XbaI-3xstop-BGHpA-UAS-hTERT enh-SV40 enh.-CMV enh.-BssHII

```
TCTAGAgctagatgactaacTTTAAACCGCTGATCAGCCTCGACTGTGCCTTCTAGTTGC  (1)
CAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTC
TGGGGGGTGGGGTGGGGCAGGACAGCAAGGGGGAGGATTGGGAAGACAATAGCAGGCATGCT
GGGGATGCGGTGGGCTCTATGGcggagtactgtcctccgttccacgtggcggagggactg  (2)
gggacccgggcacccgtcctgcccttcacctcgagtccgctcctccgcgcggacccg
ccccgtccgacccctcccgggtccccggccagcccccctccgggccctcccagcccctccc
cttcctttccgcggccccgccctctcctcgcgggcgcgagtttGGAAAGTCCCCAGGCTCCC  (3)
CAGCAGGCAGAAGTATCCAAAGCATCCATCTCAATTAGTCAGCAACCAGGTGTGGAAAGTCC
CCAGGCTCCCCAGCAGGCAGAAGTATCCAAAGCATCCATCTCAATTAGTCAGCAACCATAGT
CCCGCCCCTAACTCCGCCCATCCCGCCCCTAACTCCGCCCAGTTCCGCCCATTCTCCGCCCC
ATGGCTGACTAATTTTTTTTATTTATGCAGAGGCCGAGGCCGCCTCTGCCTCTGAGCTATTC
CAGAAGTAGTGAGGAGGCTTTTTTGGAGGCCTAGGCTTTTGCAAAAAGCTCgttacataac  (4)
ttacggtaaatggcccgcctggctgaccgcccaacgacccccgcccattgacgtcaataatg
acgtatgttcccatagtaacgccaatagggactttccattgacgtcaatgggtggagtatt
tacggtaaactgcccacttggcagtacatcaagtgtatcatatgccaagtacgccccctattg
acgtcaatgacggtaaatggcccgcctggcattatgcccagtacatgaccttatgggactt
tcctacttggcagtacatctacgtattagtcatcgctattaccatggtgatgcggttttggca
gtacatcaatgggcgtggatagcggtttgactcacggggatttccaagtctccaccccattg
acgtcaatgggagtttgttttggcaccaaaatcaacgggactttccaaaatgtcgtaacaac
tccgccccattgacgcaaatgggcggtaggcgtgTTGCCGCGG
```

Fig. 35-1

Full nucleotide sequence of construct No. 14 vector

GGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGAT T
AGCAGAGCGAGGTATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCTCGGAAAAAGAGT
TGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATTTTCTACCGAAGAAAG
GCCCACCCGTGAAGGTGAGCCAGTGAGTTGATTGCAGTCCAGTTACGCTGGAGTCTGAGGCT
CGTCCTGAATGTGTAAAACGACGGCCAGTTTATCTAGTCAGCTTGATTCTAGCTGATCGTGG
ACCGGAAGGTGAGCCAGTGAGTTGATTGCAGTCCAGTTACGCTGGAGTCTGAGGCTCGTCCT
GAATGATATACGCGTCGGAGGGTTGCGTTTGAGACGGGCGACAGATACGCGTCGACGTCCGC
CATAaattttttgcaaaagcctggcctccaaaaagcctcctcactacttctggaatagct (1)
gagaggccgaggcggcctcggcctctgcataaataaaaaaattagtcagccttgggcgga
gaaactatcgttgctgactaattgagatcggagtactgtcctccggttacataacttacgg (2)
taaatggcccgcctggctgaccgcccaacgacccccgcccattgacgtcaataatgacgtat
gttcccatagtaacgccaatagggactttccattgacgtcaatgggtggagtatttacggta
aactgcccacttggcagtacatcaagtgtatcatatgccaagtacgccccctattgacgtca
atgacggtaaatggcccgcctggcattatgcccagtacatgaccttatgggactttcctact
tggcagtacatctacgtattagtcatcgctattaccatggtgatgcggttttggcagtacat
caatgggcgtggatagcggtttgactcacggggatttccaagtctccaccccattgacgtca
atgggagtttgttttggcaccaaaatcaacgggactttccaaaatgtcgtaacaactccgcc
ccattgacgcaaatgggcggtaggcgtgtacggtgggaggtctatataagcagagctcgttt
agtgaaccgtcagatcgcctggagacgccatccacgctgttttgacctccatagaagacacc
gggaccgatccagcctccgcggccggaacggtgcattggaacgcggattcccccgtgccaag
agtgacgtaagtaccgcctatagactctataggcacacccctttggctcttatccatcaatt
aatacgactcactatagggagacagactgttcctttcctgggtctttcttgcttcgagggg (3)
ctcgcatctctccttcacgcgccccgcccgccctacctgaggccgccatccacgccggttgagt
cgcgttctgccgcctcccgcctgtggtgcctcctgaactgcgtccgccgtctaggtaagttt
aaagctcaggtcgagaccgggcctttgtccggcgctcccttggagcctacctagactcagcc
ggctctccacgctttgcctgaccctgcttgctcaactctacgtctttgttttctgttt
ctgcgccgttacagatccaagccaccCCGAATTCCGGGAGATCTCCCGGGTACCCG
AGGACTAGTtcgacgccggccaagacagcacagacagattgacctattgggtgttcgcga (4)
gtgtgagagggaagcgccgcggcctgtattactagacctgccttcgcctggttcgtggcgc
cttgtgacccgggccctgccgctgcaagtcgaaattgcgctgtgctcctgtgctacggc
ctgtggctggactgcctgctgctgccctactggctggcaagatcaagctctccctggtggcc
gcgatcctCCGGATCCGCCCCAAGCTTGGGTTACCTAGGcctaattccagcgagaggca (5)
gaggagcgagcgggcggccggctagggtggaagagccgggcgagcagagctgcgctgcgg
cgtcctgggaagggagatccggagcgaataggggcttcgcctctggccagcctcccgct
gatccccagccagcggtccgcaaccttgccgcatccacgaaactttgcccatagcagcgg
gcgggcactttgcactggaacttacaacacccgagcaaggacgcgactctccgacgcggg
aggctattctgccatttggggacacttccccgccgctgccaggaccgcttctctgaaagg
ctctccttgcagctgcttagacgctggatttttcgggtagtggaaaccagcagcctccc
gcgCCGCTCGAGCGGAAAGCCCTTTTGCTCTAGAGCtagatgactaacGTTTAAACCCGCT

Fig. 35-2

```
GATCAGCCTCGACTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGAGGAAATTGCATC
GCATTGTCTGAGTAGGTGTCATTCTATTCTGGGGGTGGGGTGGGGCAGGACAGCAAGGGGG
AGGATTGGAAGACAATAGCAGGCATGCTGGGGATGCCGTGGGCTCTATGGcggagtactgt
cctccggttcccacgtggcggaggactggggacccgggcacccgtcctgcccttcacctt  (6)
ccagctccgcctcctccgcgcggaccccgcccgtcccgacccctcccgggtcccccggccca
gccccctccgggccctcccagcccctcccttcctttccgcgggcccgccctctcctcgcgg
cgcgagtttTGGAAAGTCCCCAGGCTCCCCAGCAGGCAGAAGTATCCAAAGCATCCATCTCA (7)
ATTAGTCAGCAACCAGGTGTGGAAAGTCCCCAGGCTCCCCAGCAGGCAGAAGTATCCAAAGC
ATCCATCTCAATTAGTCAGCAACCATAGTCCCGCCCCTAACTCCGCCCATCCCGCCCCTAAC
TCCGCCCAGTTCCGCCCATTCTCCGCCCCATGGCTGACTAATTTTTTTATTTATGCAGAGG
CCGAGGCCCCTCTGCCTCTGAGCTATTCCAGAAGTAGTGAGGAGGCTTTTTGCAGGCCAA
GGCTTTGCAAAAGCTCcgttacataactacggtaaatggcccgcctggctgaccgccca
acgaccccgcccattgacgtcaataatgacgtatgttcccatagtaacgccaatagggact
ttccattgacgtcaatggggtggagtatttacggtaaactgcccacttggcagtacatcaagt
gtatcatatgccaagtacgccccctattgacgtcaatgacggtaaatggcccgcctggcatt
atgcccagtacatgaccttatgggactttcctacttggcagtacatctacgtattagtcatc
gctattaccatggtgatgcggttttggcagtacatcaatgggcgtggatagcggtttgactc
acggggatttccaagtctccaccccattgacgtcaatgggagtttgttttggcaccaaaatc
aacgggactttccaaaatgtcgtaacaactccgccccattgacgcaaatgggcggtaggcgt
gTTGGCGCCCAAATCAGTTCTGGACGAGCGAGCTGTCGTCCGGCGGCCGCGATCTTACGGC
ATTATACGTATGATCGGTCCACGATCAGCTAGATTATCTAGTCAGCTTGATGTCATAGCTGT
TTCCTGAGGCTCAATACTGACCATTTAAATCATACCTGACCTCCATAGCAGAAAGTCAAAAG
CCTCCGACCGGAGGCTTTTGACTTGATCGGCACGTAAGAGGTTCCAACTTTCACCATAATGA
AATAAGATCACTACCGGGCGTATTTTTTGAGTTATCGAGATTTTCAGGAGCTAAGGAAGCTA
AAATGAGCCATATTCAACGGGAAACGTCTTGCTTGAAGCCGCGATTAAATTCCAACATGGAT
GCTGATTTATATGGGTATAAATGGGCTCGCGATAATGTCGGGCAATCAGGTGCGACAATCTA
TCGATTGTATGGGAAGCCCGATGCGCCAGAGTTGTTTCTGAAACATGGCAAAGGTAGCGTTG
CCAATGATGTTACAGATGAGATGGTCAGGCTAAACTGGCTGACGGAATTTATGCCTCTTCCG
ACCATCAAGCATTTTATCCGTACTCCTGATGATGCATGGTTACTCACCACTGCGATCCCAGG
GAAAACAGCATTCCAGGTATTAGAAGAATATCCTGATTCAGGTGAAAATATTGTTGATGCGC
TGGCAGTGTTCCTGCGCCGGTTGCATTCGATTCCTGTTTGTAATTGTCCTTTTAACGGCGAT
CGCGTATTTCGTCTCGCTCAGGCGCAATCACGAATGAATAACGGTTTGGTTGGTGCGAGTGA
TTTTGATGACGAGCGTAATGGCTGGCCTGTTGAACAAGTCTGGAAAGAAATGCATAAACTCT
TGCCATTCTCACCGGATTCAGTCGTCACTCATGGTGATTTCTCACTTGATAACCTTATTTTT
GACGAGGGGAAATTAATAGGTTGTATTGATGTTGGACGAGTCGGAATCGCAGACCGATACCA
GGATCTTGCCATCCTATGGAACTGCCTCGGTGAGTTTTCTCCTTCATTACAGAAACGGCTTT
TTCAAAAATATGGTATTGATAATCCTGATATGAATAAATTGCAGTTTCACTTGATGCTCGAT
GAGTTTTCTAATGAGGACTAAATGTAATCACCTGGCTCACCTTCGGGTGGGCCTTTCTGC
GTTTCTGGCGTTTTTCCATAGGCTCCGCCCCCCTGACGAGCATCACAAAAATCGATGCTCAA
GTCAGAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTC
GCTCCAAGCT
```

Construct No.15

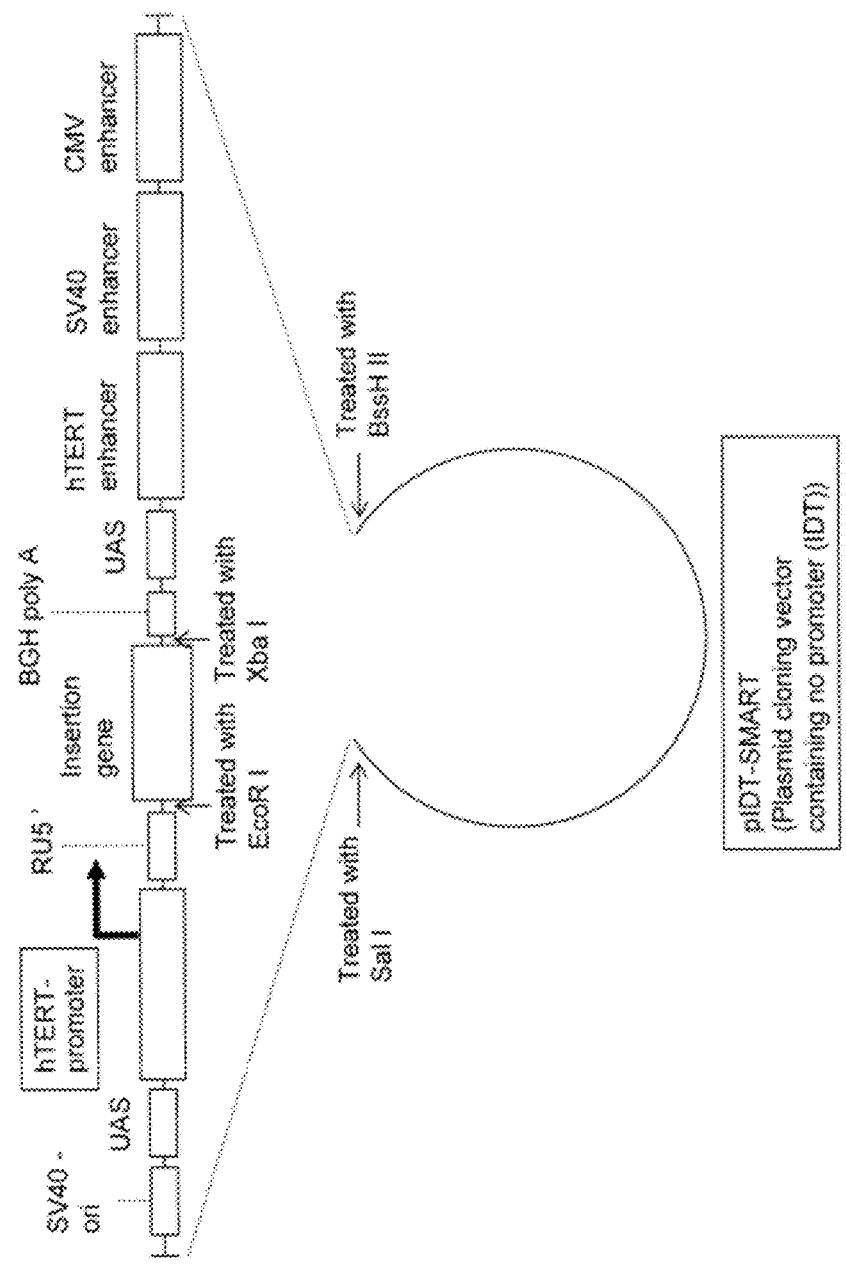
Fig. 37 Construct No. 16

Fig. 38

P-SV1RU: 1072 bp ---- pIDT SMART (Kan)

(1)      (2)      (3)      (4)
SalI-SV40 ori+UAS+SV40 enh+intron A+RU5'-EcoRI

```
ACGCG/TCGACGTCGGCCATA
aattttttgcaaaagccttggcctccaaaaaagcctcctcactacttctggaatagctcaga (1)
ggccgaggcggcctcggcctctgcataaataaaaaaaattagtcagccttggggcggagaaa
ctatcgttgctgactaattgagat cggagtactgtcctccg
TGGAAAGTCCCCAGGCTCCCCAGCAGGCAGAAGTATGCAAAGCATGCATCTCAATTAGTCAG (2)
CAACCAGGTGTGGAAAGTCCCCAGGCTCCCCAGCAGGCAGAAGTATGCAAAGCATGCATCTC
AATTAGTCAGCAACCATAGTCCCGCCCCTAACTCCGCCCATCCCGCCCCTAACTCCGCCCAG
TTCCGCCCATTCTCCGCCCCATGGCTGACTAATTTTTTTATTTATGCAGAGGCCGAGGCCG
CCTCTGCCTCTGAGCTATTCCAGAAGTAGTGAGGAGGCTTTTTGGAGGCCTAGGCTTTTGC
AAAAAGCTG
tacggtgggaggtctatataagcagagctcgtttagtgaaccgtcagatcgcctggagacgc (3)
catccacgctgttttgacctccatagaagacaccgggaccgatccagcctccgcggccggga
acggtgcattggaacgcggattccccgtgccaagagtgacgtaagtaccgcctatagactct
ataggcacacccctttggctcttatccatcaattaatacgactcactatagggagacagact
gttcctttcctgggtcttttctg
gcttcgaggggctcgcatctctccttcacgcgcccgccgccctacctgaggccgccatccac (4)
gccggttgagtgcgttctgccgcctccgcctgtggtgcctcctgaactggtccgccgtc
taggtaagtttaaagctcaggtcgagaccgggcctttgtccggcgctccttggagcctacc
tagactcagccggctctccagctttgcctgacctgcttgctcaactctacgtctttgttt
cgtttctgttctgcgccgttacagatccaagccacc CCGG/AATTCGG
```

Fig. 39

P-T1RU: 942 bp ---- pIDT SMART (Kan)
(1)      (2)      (3)      (4)
[SalI]-SV40 ori+UAS+hTERT enh+intron A+RU5'-[EcoRI]

ACGCG/TCGAGTCGGCCATA
aattttttgcaaaagccttggcctccaaaaagcctcctcactacttctggaatagctcaga (1)
ggccgaggcggcctcggcctctgcataaataaaaaaaattagtcagccttggggcggagaaa
ctatcgttgctgactaattgagat cggagtactgtcctccg
cttcccacgtggcggagggactggggaccggcaccgtcctgcccttcaccttccagct (2)
ccgctcctcggcgggacccgccgtccgacccctcccggtcccggccagccc
tccggcctccagccctccccttctttccgcggccccgccctctcctcgcgggcgcgag
ttt
tacggtgggaggtctatataagcagagctcgtttagtgaaccgtcagatcgcctggagacgc (3)
catccacgctgttttgacctccatagaagacaccgggaccgatccagcctccgcggccggga
acggtgcattggaacgcggattccccgtgccaagagtgacgtaagtaccgcctatagactct
ataggcacaccctttggctcttatcgataattaatacgactcactataggagacagact
gttcctttcctgggtcttttctg
gcttcgagggctgcatctctccttcacgcgcccgccgcctacctgaggccgccatccac (4)
gccggttgagtcgcgttctgccgcctcccgcctgtggtgcctcctgaactgcgtccgccgtc
taggtaagtttaaagctcaggtcgagaccgggcctttgtccggcgctccttggagcctacc
tagactcagccggctctccacgctttgcctgaccctgcttgctcaactctacgtctttgttt
cgttttctgttctgcgccgttacagatccaagccacc CCGG/AATTCCGG

Fig. 40

GFP (EcoR1-BamH1)
CCG/GAATTC/CGG acc atg gtg agc aag ggc gag gag ctg ttc acc ggg gtg
gtg ccc atc ctg gtc gag ctg gac ggc gac gta aac ggc cac aag ttc
agc gtg tcc ggc gag ggc gag ggc gat gcc acc tac ggc aag ctg acc
ctg aag ttc atc tgc acc acc ggc aag ctg ccc gtg ccc tgg ccc acc
ctc gtg acc acc ctg acc tac ggc gtg cag tgc ttc agc cgc tac ccc
gac cac atg aag cag cac gac ttc ttc aag tcc gcc atg ccc gaa ggc
tac gtc cag gag cgc acc atc ttc ttc aag gac gac ggc aac tac aag
acc cgc gcc gag gtg aag ttc gag ggc gac acc ctg gtg aac cgc atc
gag ctg aag ggc atc gac ttc aag gag gac ggc aac atc ctg ggg cac
aag ctg gag tac aac tac aac agc cac aac gtc tat atc atg gcc gac
aag cag aag aac ggc atc aag gtg aac ttc aag atc cgc cac aac atc
gag gac ggc agc gtg cag ctc gcc gac cac tac cag cag aac acc ccc
atc ggc gac ggc ccc gtg ctg ctg ccc gac aac cac tac ctg agc acc
cag tcc gcc ctg agc aaa gac ccc aac gag aag cgc gat cac atg gtc
ctg ctg gag ttc gtg acc gcc gcc ggg atc act ctc ggc atg gac gag
ctg tac aag tga CGC/GGATCC/GCG

Fig. 41-1

14-GFP

Sal1- P-CMViRU -EcoRI- GFP -BamHI-HindIII-XhoI-Myc IRES-XhoI-

Stul-XbaI- pA-3enh -BssHII

ACGCGTCGACGTCGCCATA aatttttttgcaaaagccttggcctccaaaaaagcctcctcactacttctggaatagctcaga (1)
ggccgaggcggcctcggcctctgcataaataaaaaaaattagtcagccttggggcggagaaa
ctatcgttgctgactaattgagatcggagtactgtcctccgcgttacataacttacggtaaa
tggcccgcctggctgaccgcccaacgaccccccgcccattgacgtcaataatgacgtatgttc
ccatagtaacgccaatagggactttccattgacgtcaatgggtggagtatttacggtaaact
gcccacttggcagtacatcaagtgtatcatatgccaagtacgccccctattgacgtcaatga
cggtaaatggcccgcctggcattatgcccagtacatgaccttatgggactttcctacttggc
agtacatctacgtattagtcatcgctattaccatggtgatgcggttttggcagtacatcaat
gggcgtggatagcggtttgactcacggggatttccaagtctccaccccattgacgtcaatgg
gagtttgttttggcaccaaaatcaacgggactttccaaaatgtcgtaacaactccgccccat
tgacgcaaatgggcggtaggcgtgtacggtgggaggtctatataagcagagctcgtttagtg
aaccgtcagatcgcctggagacgccatccacgctgttttgacctccatagaagacaccggga
ccgatccagcctccgcggccgggaacggtgcattggaacgcggattccccgtgccaagagtg
acgtaagtaccgcctatagactctataggcacaccctttggctcttatccatcaattaata
cgactcactatagggagacagactgttcctttcctgggtcttttctggcttcgaggggctcg
catctctccttcacgcgccgcgcgccctacctgaggccgccatccacgccggttgagtcgcg
ttctgccgcctcccgcctgtggtgcctctgaactgcgtccgccgtctaggtaagttaaag
ctcaggtcgagaccgggcctttgtccggcgctcccttggagcctacctagactcagccggct
ctccacgctttgcctgaccctgcttgctcaactctacgtctttgtttcgttttctgttctgc
gccgttacagatccaagccacc CGGAATTCGG acc atg gtg agc aag ggc gag (2)
gag ctg ttc acc ggg gtg gtg ccc atc ctg gtc gag ctg gac ggc gac
gta aac ggc cac aag ttc agc gtg tcc ggc gag ggc gag ggc gat gcc
acc tac ggc aag ctg acc ctg aag ttc atc tgc acc acc ggc aag ctg
ccc gtg ccc tgg ccc acc ctc gtg acc acc ctg acc tac ggc gtg cag
tgc ttc agc cgc tac ccc gac cac atg aag cag cac gac ttc ttc aag
tcc gcc atg ccc gaa ggc tac gtc cag gag cgc acc atc ttc ttc aag
gac gac ggc aac tac aag acc cgc gcc gag gtg aag ttc gag ggc gac
acc ctg gtg aac cgc atc gag ctg aag ggc atc gac ttc aag gag gac
ggc aac atc ctg ggg cac aag ctg gag tac aac tac aac agc cac aac
gtc tat atc atg gcc gac aag cag aag aac ggc atc aag gtg aac ttc
aag atc cgc cac aac atc gag gac ggc agc gtg cag ctc gcc gac cac
tac cag cag aac acc ccc atc ggc gac ggc ccc gtg ctg ctg ccc gac
aac cac tac ctg agc acc cag tcc gcc ctg agc aaa gac ccc aac gag
aag cgc gat cac atg gtc ctg ctg gag ttc gtg acc gcc gcc ggg atc
act ctc ggc atg gac gag ctg tac aag tga CGCGGATCCGG CCCAAGCTTGGG
TTAGCTAGC

Fig. 41-2

```
cctaattccagcgagaggcagagggagcgagcgggcggccggctagggtggaagagccggg  (3)
cgagcagagctgcgctgcgggcgtcctgggaaggagatccggagcgaatagggggcttcgc
ctctggcccagccctcccgctgatccccagccagcggtccgcaaccccttgccgcatccacg
aaactttgccatagcagcgggcgggcactttgcactggaacttacaacacccgagcaagga
cgcgactctccgacgcggggaggctattctgcccatttggggacacttcccgccgctgcc
aggacccgcttctctgaaaggctctccttgcagctgctagacgctggatttttttcggta
gtggaaaaccagcagcctcccgcg CCGTTCGAGCGG AAAAGGCCTTTT GCTCTAGAGC
tagatgactaacGTTTAAACCCGCTGATCAGCCTCGACTGTGCCTTCTAGTTGCCAGCCATC  (4)
TGTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGGATGC
GGTGGGCTCTATGGcggagtactgtcctccgcttccacgtggcggagggactggggacccg
ggcacccgtcctgcccttcaccttccagctccgcctcctccgcgcggacccccgcccgtcc
cgaccctccgggtccccggcccagcccctccgggccctcccagccctcccttcttt
ccgcggcccgccctctcctcgcggcgcgagtttTGGAAAGTCCCCAGGCTCCCCAGCAGGC
AGAAGTATCCAAAGCATCCATCTCAATTAGTCAGCAACCAGGTGTGGAAAGTCCCCAGGCTC
CCCAGCAGGCAGAAGTATCCAAAGCATCCATCTCAATTAGTCAGCAACCATAGTCCCGCCCC
TAACTCCGCCCATCCCGCCCCTAACTCCGCCCAGTTCCGCCCATTCTCCGCCCCATGGCTGA
CTAATTTTTTTATTTATGCAGAGGCCGAGGCCGCCTCTGCCTCTGAGCTATTCCAGAAGTA
GTGAGGAGGCTTTTTGGAGGCCAAGGCTTTTGCAAAAAGCTCcgttacataacttacggta
aatggcccgcctggctgaccgcccaacgaccccgcccattgacgtcaataatgacgtatgt
tcccatagtaacgccaatagggactttccattgacgtcaatggtggagtatttacggtaaa
ctgcccacttggcagtacatcaagtgtatcatatgccaagtacgccccctattgacgtcaat
gacggtaaatggcccgcctggcattatgcccagtacatgaccttatggactttcctacttg
gcagtacatctacgtattagtcatcgctattaccatggtgatgcggttttggcagtacatca
atgggcgtggatagcggtttgactcacggggatttccaagtctccaccccattgacgtcaat
gggagtttgttttggcaccaaaatcaacgggactttccaaaatgtcgtaacaactccgcccc
attgacgcaaatgggcggtaggcgtg TTCCGCGCCA
```

Fig. 42-1

15-GFP

Sall- P-SV1RU -EcoRl- GFP -BamHI-HindIII-NheI-Myc IRES-XhoI-
         (1)         (2)                      (3)
Stul-XbaI- pA-3enh -BssHII
           (4)

ACGCGTCGACGTCGGCATA aatttttgcaaaagccttggcctccaaaaaagcctcctcactacttctggaatagctcaga (1)
ggccgaggcggcctcggcctctgcataaataaaaaaaattagtcagccttggggcggagaaa
ctatcgttgctgactaattgagatcggagtactgtcctccgTGGAAAGTCCCCAGGCTCCCC
AGCAGGCAGAAGTATGCAAAGCATGCATCTCAATTAGTCAGCAACCAGGTGTGGAAAGTCCC
CAGGCTCCCCAGCAGGCAGAAGTATGCAAAGCATGCATCTCAATTAGTCAGCAACCATAGTC
CCGCCCCTAACTCCGCCCATCCCGCCCCTAACTCCGCCCAGTTCCGCCCATTCTCCGCCCCA
TGGCTGACTAATTTTTTTTATTTATGCAGAGGCCGAGGCCGCCTCTGCCTCTGAGCTATTCC
AGAAGTAGTGAGGAGGCTTTTTTGGAGGCCTAGGCTTTTGCAAAAAGCTCtacggtgggagg
tctatataagcagagctcgtttagtgaaccgtcagatcgcctggagacgccatccacgctgt
tttgacctccatagaagacaccgggaccgatccagcctccgcggccgggaacggtgcattgg
aacgcggattccccgtgccaagagtgacgtaagtaccgcctatagactctataggcacaccc
ctttggctcttatccatcaattaatacgactcactatagggagacagactgttcctttcctg
ggtcttttctggcttcgaggggctcgcatctctccttcacgcgcccgccgccctacctgagg
ccgccatccacgccggttgagtcgcgttctgccgcctcccgcctgtggtgcctcctgaactg
cgtccgccgtctaggtaagtttaaagctcaggtcgagaccggggcctttgtccggcgctccct
tggagcctacctagactcagccggctctccacgctttgcctgaccctgcttgctcaactcta
cgtctttgtttcgttttctgttctgcgccgttacagatccaagccacc CCGGAATTCCGG acc atg gtg agc aag ggc gag gag ctg ttc acc ggg gtg gtg ccc atc (2)
ctg gtc gag ctg gac ggc gac gta aac ggc cac aag ttc agc gtg tcc
ggc gag ggc gag ggc gat gcc acc tac ggc aag ctg acc ctg aag ttc
atc tgc acc acc ggc aag ctg ccc gtg ccc tgg ccc acc ctc gtg acc
acc ctg acc tac ggc gtg cag tgc ttc agc cgc tac ccc gac cac atg
aag cag cac gac ttc ttc aag tcc gcc atg ccc gaa ggc tac gtc cag
gag cgc acc atc ttc ttc aag gac gac ggc aac tac aag acc cgc gcc
gag gtg aag ttc gag ggc gac acc ctg gtg aac cgc atc gag ctg aag
ggc atc gac ttc aag gag gac ggc aac atc ctg ggg cac aag ctg gag
tac aac tac aac agc cac aac gtc tat atc atg gcc gac aag cag aag
aac ggc atc aag gtg aac ttc aag atc cgc cac aac atc gag gac ggc
agc gtg cag ctc gcc gac cac tac cag cag aac acc ccc atc ggc gac
ggc ccc gtg ctg ctg ccc gac aac cac tac ctg agc acc cag tcc gcc
ctg agc aaa gac ccc aac gag aag cgc gat cac atg gtc ctg ctg gag
ttc gtg acc gcc gcc ggg atc act ctc ggc atg gac gag ctg tac aag
tga CGGGATCCGG

Fig. 42-2

```
CCGAAGCTTGGG TTACCTAGC
ccctaattccagcgagaggcagaggagcgagcgggcggccggctagggtggaagagccggg (3)
cgagcagagctgcgctgcggcgtcctgggaaggagatccggagcgaataggggcttcgc
ctctggccagccctcccgctgatccccagccagcggtccgcaaccttgccgcatccacg
aaactttgcccatagcagcggcgggcactttgcactggaacttacaacaccgagcaagga
cgcgactctcccgacgcgggcaggctattctgcccatttgggacacttcccgcgctgcc
aggaccgcttctctgaaaggctctccttgcagctgcttagacgctggattttttctcggta
gtggaaaaccagcagcctcccgcg CCGCTCGAGGCGG AAAGGGCCTTT GGCCTAGAGC
tagatgactaacGTTTAAACCCGCTGATCAGCCTCGACTGTGCCTTCTAGTTGCCAGCCATC (4)
TGTTGTTTGCCCCTCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGT
GGGGTGGGGCAGGACAGCAAGGGGGAGGATTGGGAAGACAATAGCAGGCATGCTGGGGATGC
GGTGGGCTCTATGGcggagtactgtcctccgcttccacgtggcggagggactggggacccg
ggcacccgtcctgccccttcaccttccagctccgcctcctccgcgcggaccccgccccgtcc
cgaccccctcccgggtccccggcccagcccctcgggcc ctcccagcccctcccttcctttt
ccgcggccccgccctctcctcgcggcgcgagtttTGGAAAGTCCCCAGGCTCCCCAGCAGGC
AGAAGTATCCAAAGCATCCATCTCAATTAGTCAGCAACCAGGTGTGGAAAGTCCCCAGGCTC
CCCAGCAGGCAGAAGTATCCAAAGCATCCATCTCAATTAGTCAGCAACCATAGTCCCGCCCC
TAACTCCGCCCATCCCGCCCCTAACTCCGCCCAGTTCCGCCCATTCTCCGCCCCATGGCTGA
CTAATTTTTTTTATTTATGCAGAGGCCGAGGCCGCCTCTGCCTCTGAGCTATTCCAGAAGTA
GTGAGGAGGCTTTTTGGAGGCCAAGGCTTTTGCAAAAAGCTCcgttacataacttacggta
aatggcccgcctggctgaccgcccaacgaccccgcccattgacgtcaataatgacgtatgt
tcccatagtaacgccaataggactttccattgacgtcaatgggtggagtatttacggtaaa
ctgcccacttggcagtacatcaagtgtatcatatgccaagtacgccccctattgacgtcaat
gacggtaaatggcccgcctggcattatgcccagtacatgaccttatgggactttcctacttg
gcagtacatctacgtattagtcatcgctattaccatggtgatgcggttttggcagtacatca
atgggcgtggatagcggtttgactcacggggatttccaagtctccaccccattgacgtcaat
gggagtttgttttggcaccaaaatcaacgggactttccaaaatgtcgtaacaactccgcccc
attgacgcaaatgggcggtaggcgtg TTGGGCCGGCAA
```

Fig. 43-1

16-GFP

SalI- P-T1RU -EcoRI- GFP -BamHI-HindIII-NheI-Myc IRES-XhoI-
StuI-XbaI- pA-3enh -BssHII

ACGC GTCGAC GTCGGCCATA aatttttgcaaaagccttggcctccaaaaaagcctcctcactacttctggaatagctcaga (1)
ggccgaggcggcctcggcctctgcataaataaaaaaattagtcagccttggggcggagaaa
ctatcgttgctgactaattgagatcggagtactgtcctccgcttcccacgtggcggagggac
tggggacccggggcacccgtcctgccccttcaccttccagctccgcctcctccgcgcggaccc
cgccccgtcccgaccccctcccgggtccccggcccagccccctccgggccctccagccctc
ccttcctttccgcgggccccgccctctcctcgcggcgcgagtttacggtgggaggtctata
taagcagagctcgtttagtgaaccgtcagatcgcctggagacgccatccacgctgttttgac
ctccatagaagacaccgggaccgatccagcctccgcggccgggaacggtgcattggaacgcg
gattccccgtgccaagagtgacgtaagtaccgcctatagactctataggcacaccccctttgg
ctcttatccatcaattaatacgactcactataggggagacagactgttcctttcctgggtctt
ttctggcttcgaggggctcgcatctctccttcacgcgcccgccgccctacctgaggccgcca
tccacgccggttgagtcgcgttctgccgcctcccgcctgtggtgcctcctgaactgcgtccg
ccgtctaggtaagtttaaagctcaggtcgagaccgggcctttgtccggcgctcccttggagc
ctacctagactcagccggctctccacgctttgcctgaccctgcttgctcaactctacgtctt
tgtttcgttttctgttctgcgccgttacagatccaagccacc CCGGAATTCGC acc atg (2)
gtg agc aag ggc gag gag ctg ttc acc ggg gtg gtg ccc atc ctg gtc
gag ctg gac ggc gac gta aac ggc cac aag ttc agc gtg tcc ggc gag
ggc gag ggc gat gcc acc tac ggc aag ctg acc ctg aag ttc atc tgc
acc acc ggc aag ctg ccc gtg ccc tgg ccc acc ctc gtg acc acc ctg
acc tac ggc gtg cag tgc ttc agc cgc tac ccc gac cac atg aag cag
cac gac ttc ttc aag tcc gcc atg ccc gaa ggc tac gtc cag gag cgc
acc atc ttc ttc aag gac gac ggc aac tac aag acc cgc gcc gag gtg
aag ttc gag ggc gac acc ctg gtg aac cgc atc gag ctg aag ggc atc
gac ttc aag gag gac ggc aac atc ctg ggg cac aag ctg gag tac aac
tac aac agc cac aac gtc tat atc atg gcc gac aag cag aag aac ggc
atc aag gtg aac ttc aag atc cgc cac aac atc gag gac ggc agc gtg
cag ctc gcc gac cac tac cag cag aac acc ccc atc ggc gac ggc ccc
gtg ctg ctg ccc gac aac cac tac ctg agc acc cag tcc gcc ctg agc
aaa gac ccc aac gag aag cgc gat cac atg gtc ctg ctg gag ttc gtg
acc gcc gcc ggg atc act ctc ggc atg gac gag ctg tac aag tga

CCGGATCCCG

Fig. 43-2

```
CCCAAGCTTGGG TTAGCTAGC
ccctaattccagcgagaggcagaggagcgagcggcggccggctagggtggaagagccggg (3)
cgagcagagctgcgctgcgggcgtcctggaagggagatccggagcgaatagggggcttcgc
ctctggccagccctcccgctgatccccagccagcggtccgcaacccttgccgcatccacg
aaactttgcccatagcagcgggcgggcactttgcactggaacttacaacacccgagcaagga
cgcgactctcccgacgcggggaggctattctgcccatttgggqacacttcccogccgctgcc
aggacccgcttctctgaaaggctctccttgcagctgcttagacgctggattttttcgggta
gtggaaaaccagcagcctcccgcg CCCCTCCACCGG AAAAGGCCTTTT GCTCTAGAGC
tagatgactaacGTTTAAACCCGCTGATCAGCCTCGACTGTGCCTTCTAGTTGCCAGCCATC (4)
TGTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGGATGC
GGTGGGCTCTATGGcggagtactgtcctccgcttcccacgtggcggagggactggggacccg
ggcacccgtcctgcccttcaccttccagctccgcctcctccgcgcggaccccgccccgtcc
cgaccctcccgggtcccggcccagccccctccgggccctcccagcccctccccttcctt
ccgcggccccgccctctcctcgcgggcgcgagtttTGGAAAGTCCCCAGGCTCCCCAGCAGGC
AGAAGTATCCAAAGCATCCATCTCAATTAGTCAGCAACCAGGTGTGGAAAGTCCCCAGGCTC
CCCAGCAGGCAGAAGTATCCAAAGCATCCATCTCAATTAGTCAGCAACCATAGTCCCGCCCC
TAACTCCGCCCATCCCGCCCCTAACTCCGCCCAGTTCCGCCCATTCTCCGCCCCATGGCTGA
CTAATTTTTTTTATTTATGCAGAGGCCGAGGCCGCCTCTGCCTCTGAGCTATTCCAGAAGTA
GTGAGGAGGCTTTTTGGAGGCCAAGGCTTTTGCAAAAAGCTCcgttacataacttacggta
aatggcccgcctggctgaccgcccaacgaccccgcccattgacgtcaataatgacgtatgt
tcccatagtaacgccaatagggactttccattgacgtcaatgggtggagtatttacggtaaa
ctgcccacttggcagtacatcaagtgtatcatatgccaagtacgccccctattgacgtcaat
gacggtaaatggcccgcctggcattatgcccagtacatgaccttatgggactttcctacttg
gcagtacatctacgtattagtcatcgctattaccatggtgatgcggttttggcagtacatca
atgggcgtggatagcggtttgactcacggggatttccaagtctccaccccattgacgtcaat
gggagtttgttttggcaccaaaatcaacgggactttccaaaatgtcgtaacaactccgcccc
attgacgcaaatgggcggtaggcgtg TTGGCGCGCCAA
```

Fig. 45

EPO-6His gene sequence

CCGG/AATTCCGGaccatggggtgcacgaatgtcctgcctggctgtggcttctcctgtccc
tgctgtcgctccctctggcctcccagtcctgggcgccccaccacgcctcatctgtgacagc
cgagtcctggagaggtacctcttggaggccaaggaggccgagaatatcacgacgggctgtgc
tgaacactgcagcttgaatgagaatatcactgtcccagacaccaaagttaatttctatgcct
ggaagaggatggaggtcgggcagcaggccgtagaagtctggcagggcctggcctgctgtcg
gaagctgtcctgcggggccaggccctgttggtcaactcttcccagccgtgggagccctgca
gctgcatgtggataaagccgtcagtggccttcgcagcctcaccactctgcttcgggctctgg
gagcccagaaggaagccatctcccctccagatgcggcctcagctgctccactccgaacaatc
actgctgacactttccgcaaactcttccgagtctactccaatttcctccggggaaagctgaa
gctgtacacaggggaggcctgcaggacaggggacaga gga cca ggt **cat cac cac cat
cac cat tgaGCT/CTAGAGC**

Fig. 47A

Human IgG (light chain) gene sequence

```
           (1)                                    (2)
EcoRI - XhoI - Light chain (Myc ab/ clone 9E10)-6His - XbaI
```

```
G/AATTCCGG CCGCTCGAGCGG acc atg gag aaa gac aca ctc ctg cta tgg (1)
gtc ctg ctt ctc tgg gtt cca ggt tcc aca ggt gac att gtg ctg acc
caa tct cca gct tct ttg gct gta tct cta gga cag agg gcc acc atc
tcc tgc aga gcc agc gaa agt gtt gat aat tat ggc ttt agt ttt atg
aac tgg ttc cag cag aaa cca gga cag ccc ccc aaa ctc ctc atc tat
gct ata tcc aac cga ggg tcc ggg gtc cct gcc agg ttt agt ggc agt
ggg tct ggg aca gac ttc agc ctc aac atc cat cct gta gag gag gat
gat cct gca atg tat ttc tgt cag caa act aag gag gtt ccg tgg acg
ttc ggt gga ggc acc aag ctg gaa atc aaa cgg gct gat gct gca cca
act gta tcc atc ttc cca cca tcc agt gag cag tta aca tct gga ggt
gcc tca gtc gtg tgc ttc ttg aac aac ttc tac ccc aaa gac atc aat
gtc aag tgg aag att gat ggc agt gaa cga caa aat ggc gtc ctg aac
agt tgg act gat cag gac agc aaa gac agc acc tac agc atg agc agc
acc ctc acg ttg acc aag gac gag tat gaa cga cat aac agc tat acc
tgt gag gcc act cac aag aca tca act tca ccc att gtc aag agc ttc
aac agg aat gag tgt gga ccg ggc cat cac cac cat cac cat TGA GCT/CTAGAGC
                                                                   (2)
```

Fig. 47B

Human IgG (heavy chain) gene sequence

EcoRI – (1) Heavy chain (Myc ab/ clone 9E10)-6His – (2) Bam H1 – SpeI – XbaI

```
G/AATTCCGG acc atg ggg aac ttc ggg ctc agc ttg att ttc ctt gcc ctc  (1)
att tta aaa ggt gtc cag tgt gag gtg cac ctg gtg gag tct ggg gga
gac tta gtg aag cct gga ggg tcc ctg aaa ctc tcc tgt gca gcc tct
gga ttc act ttc agt cac tat ggc atg tct tgg gtt cgc cag act cca
gac aag agg ctg gag tgg gtc gca acc att ggt agt cgt ggt act tac
acc cac tat cca gac agt gtg aag gga cga ttc acc atc tcc aga gac
aat gac aag aac gcc ctg tac ctg caa atg aac agt ctg aag tct gaa
gac aca gcc atg tat tac tgt gca aga aga agt gaa ttt tat tac tac
ggt aat acc tac tat tac tct gct atg gac tac tgg ggt caa gga acc
tca gtc acc gtc tcc tca gcc aaa acg aca ccc cca tct gtc tat cca
ctg gcc cct gga tct gct gcc caa act aac tcc atg gtg acc ctg gga
tgc ctg gtc aag ggc tat ttc cct gag cca gtg aca gtg acc tgg aac
tct ggg tcc ctg tcc agc ggt gtg cac acc ttc cca gct gtc ctg cag
tct gac ctc tac act ctg agc agc tca gtg act gtc ccc tcc agc acc
tgg ccc agc gag acc gtc acc tgc aac gtt gcc cac ccg gcc agc agc
acc aag gtg gac aag aaa att gtg ccc agg gat tgt ggt tgt aag cct
tgc ata tgt aca gtc cca gaa gta tca tct gtc ttc atc ttc ccc cca
aag ccc aag gat gtg ctc acc att act ctg act cct aag gtc acg tgt
gtt gtg gta gac atc agc aag gat gat ccc gag gtc cag ttc agc tgg
ttt gta gat gat gtg gag gtg cac aca gct cag acg caa ccc cgg gag
gag cag ttc aac agc act ttc cgc tca gtc agt gaa ctt ccc atc atg
cac cag gac tgg ctc aat ggc aag gag ttc aaa tgc agg gtc aac agt
gca gct ttc cct gcc ccc atc gag aaa acc atc tcc aaa acc aaa ggc
aga ccg aag gct cca cag gtg tac acc att cca cct ccc aag gag cag
atg gcc aag gat aaa gtc agt ctg acc tgc atg ata aca gac ttc ttc
cct gaa gac att act gtg gag tgg cag tgg aat ggg cag cca gcg gag
aac tac aag aac act cag ccc atc atg aac acg aat ggc tct tac ttc
gtc tac agc aag ctc aat gtg cag aag agc aac tgg gag gca gga aat
act ttc acc tgc tct gtg tta cat gag ggc ctg cac aac cac cat act
gag aag agc ctc tcc cac tct cct ggt aaa gga ccg ggc cat cac cac  (2)
cat cac cat TGA CGCGGATCCGCG AGGACTAGTCCT GCT/CTAGAGC
```

Construct No. 17

Fig. 50 pshuttle- REIC-TSC

XbaI-REIC-KpnI-3xenh-EcoRI

```
T/CTAGAGCaccatgcagcggcttggggccaccctgctgtgcctgctgctggcggcggcggt (1)
ccccacggccccgcgcccgctccgacggcgacctcggctccagtcaagcccggccggctc
tcagctaccgcaggaggaggccaccctcaatgagatgttccgcgaggttgaggaactgatg
gaggacacgcagcacaaattgcgcagcgcggtggaagagatggaggcagaagaagctgctgc
taaagcatcatcagaagtgaacctggcaaacttaccctccagctatcacaatgagaccaaca
cagacacgaaggttggaaataataccatccatgtgcaccgagaaattcacaagataaccaac
aaccagactggacaaatggtctttcagagacagttatcacatctgtgggagacgaagaagg
cagaaggagccacgagtgcatcatcgacgaggactgtgggccagcatgtactgccagtttg
ccagttccagtacacctgccagccatgccggggccagaggatgctctgcaccgggacagt
gagtgctgtggagaccagctgtgtgtctgggtcactgaccaaaatggccaccaggggcag
caatgggaccatctgtgacaaccagagggactgcagccgggctgtgctgtgccttccaga
gaggcctgctgttccctgtgtgcacacccctgccgtggagggcgagctttgccatgacccc
gccagccggcttctggacctcatcacctgggagctagagcctgatggagccttggaccgatg
cccttgtgccagtggctcctctgcagccccacagccacagcctggtgtatgtgtgcaagc
cgaccttcgtggggagccgtgaccaagatggggagatcctgctgcccagagaggtccccgat
gagtatgaagttggcagcttcatggaggaggtgcgccaggagctggaggacctggagaggag
cctgactgaagagatggcgctgggggagcctgcgctgccgccgctgcactgctggagggg
aagagatttagGGGGTAC/CCCGGCtagatgactaacGTTTAAACCCGCTGATCAGCCTCGA
CTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATTGGGAAG
ACAATAGCAGGCATGCTGGGGATGCGGTGGGCTCTATGGcggagtactgtcctccg (2)
acgtggggagggactggggaccccggtaccctcctgccccttcacttccagctccgcct
cctccgcgcggacccgcccgtccgacccctcccgggtcccgcgccagccccctccggg
ccctcccagcccctccccttccttccgcggccccgccctctcctcgcggcgcgagtttTGG
AAAGTCCCCAGGCTCCCCAGCAGGCAGAAGTATCCAAAGCATCCATCTCAATTAGTCAGCAA
CCAGGTGTGGAAAGTCCCCAGGCTCCCCAGCAGGCAGAAGTATCCAAAGCATCCATCTCAAT
TAGTCAGCAACCATAGTCCCGCCCCTAACTCCGCCCATCCCGCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCAGGCTTTTGCAAA
AAGTTCgttacataacttacggtaaatggcccgcctggctgaccgcccaacgacccccgcc
cattgacgtcaataatgacgtatgttcccatagtaacgccaataggggactttccattgacgt
caatgggtggagtatttacggtaaactgcccacttggcagtacatcaagtgtatcatatgcc
aagtacgccccctattgacgtcaatgacggtaaatggcccgcctggcattatgccagtaca
tgaccttatgggactttcctacttggcagtacatctacgtattagtcatcgctattaccatg
gtgatgcggttttggcagtacatcaatgggcgtggatagcggtttgactcacggggatttcc
aagtctccaccccattgacgtcaatgggagtttgttttggcaccaaaatcaacgggactttc
caaaatgtcgtaacaactccgccccattgacgcaaatggcggtaggcgtTTGCCGG/AAT
TC
```

Fig. 52

```
atgttcatgccttcttctttttcctacagctcctgggcaacgtgctggttatgtgtgt
ctcatcatttttggcaaagaattcgccttcaccatgcccctcaacgtgaacttcaccaac
aggaactatgacctcgactacgactccgtacagccctatttcatctgcgacgaggaagag
aatttctatcaccagcaacagcagagcgagctgcagccgcccgcgcccagtgaggatatc
tggaagaaattcgagctgcttcccacccgcccctgtcccgagccgccgtccgggctc
tgctctccatcctatgttgcggtcgctacgtccttctccccaaggaagacgatgacggc
ggcggtggcaacttctccaccgccgatcagctggagatgatgaccgagttacttggagga
gacatggtgaaccagagcttcatctgcgatcctgacgacgagaccttcatcaagaacatc
atcatccaggactgtatgtggagcggtttctcagccgctgccaagctggtctcggagaag
ctggcctcctaccaggctgcgcgcaaagacagcaccagcctgagccccgcccgcgggcac
agcgtctgtccacctcagcctgtacctgcaggacctcaccgccgccgcgtccgagtgc
attgaccctcagtggtctttccctacccgtcaacgacagcagctcgccaaatcctgt
acctcgtccgattccacggccttctctccttcctcggactcgctgctgtcctccgagtcc
tccccacgggccagccctgagcccctagtgctgcatgaggagacaccgccaccaccagc
agcgactctgaagaagagcaagaagatgaggaagaaattgatgtggtgtctgtggagaag
aggcaaacccctgccaagaggtcggagtcgggtcatctccatccgaggccacagcaaa
cctccgcacagccactggtcctcaagaggtgccacgtctccactcaccagcacaactac
gccgcaccccctccacaaggaaggactatccagctgcaagagggccaagttggacagt
ggcagggtcctgaagcagatcagcaacaaccgaagtgctccagcccaggtcctcagac
acggagaaaacgacaagaggcggacacacaacgtcttggaacgtcagaggaggaacgag
ctgaagcgcagcttttttgccctgcgtgaccagatccctgaattggaaaacaacgaaaag
gcccccaaggtagtgatcctcaaaaaagccaccgcctacatcctgtccattcaagcagac
gagcacaagctcacctctgaaaaggacttattgaggaaacgacgagaacagttgaaacac
aaactcgaacagcttcgaaactctggtgcataa
```

Fig. 53

```
GTTTAAACCCGCTGATCAGCCTCGACTGTGCCTTCTAGTTGCCAGCCATCTGTTGTTTGCCC
CTCCCCCGTGCCTTCCTTGACCCTGGAAGGTGCCACTCCCACTGTCCTTTCCTAATAAAATG
AGGAAATTGCATCGCATTGTCTGAGTAGGTGTCATTCTATTCTGGGGGGTGGGGTGGGGCAG
GACAGCAAGGGGGAGGATTGGGAAGACAATAGCAGGCATGCTGGGGATGCGGTGGGCTCTAT
GGCGGAGTACTGTCCTCCGCTTCCCACGTGGCGGAGGGACTGGTCCTCCGCTTCCACGTGG
CGGAGGGACTGGGGACCCGGGCACCCGTCCTGCCCCTTCACCTTCCAGCTCCGCCTCCTCCG
CGCGGACCCCGCCCGTCCCGACCCTTCCCGGGTCCCGGCCCAGCCCCCTCCGGGCCCTCC
CAGCCCCTCCCCTTCCTTTCCGCGGCCCCGCCCTCTCCTCGCGGCGCGAGTTTTGGAAAGTC
CCCAGGCTCCCCAGCAGGCAGAAGTATCCAAAGCATCCATCTCAATTAGTCAGCAACCAGGT
GTGGAAAGTCCCCAGGCTCCCCAGCAGGCAGAAGTATCCAAAGCATCCATCTCAATTAGTCA
GCAACCATAGTCCCGCCCCTAACTCCGCCCATCCCGCCCCTAACTCCGCCCAGTTCCGCCCA
TTCTCCGCCCCATGGCTGACTAATTTTTTTTATTTATGCAGAGGCCGAGGCCGCCTCTGCCT
CTGAGCTATTCCAGAAGTAGTGAGGAGGCTTTTTTGGAGGCCAAGGCTTTTGCAAAAAGCTC
CGTTACATAACTTACGGTAAATGGCCCGCCTGGCTGACCGCCCAACGACCCCCGCCCATTGA
CGTCAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAGTAC
GCCCCCTATTGACGTCAATGACGGTAAATGGCCCGCCTGGCATTATGCCCAGTACATGACCT
TATGGGACTTTCCTACTTGGCAGTACATCTACGTATTAGTCATCGCTATTACCATGGTGATG
CGGTTTTGGCAGTACATCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAAAT
GTCGTAACAACTCCGCCCCATTGACGCAAATGGGCGGTAGGCGTG
```

Fig. 55 Construct No.18

Fig. 56 Construct No. 19

Fig. 57 Construct No.20

Construct No.21

Fig. 59-1

21-GFP
pDNR-1r (Sal-BssHII)

Sal1-EcoR1-hTERT core promoter-minimal CMV promoter-
          (1)                    (2)
HindIII-R5'-HindIII-BamH1-GFP-Xho1-Xba1-BGHpA-BstXI-
        (3)              (4)              (5)
hTERT core promoter-BssHII
        (6)

GTCGACGTCGGCCATA CCGGAATTCCGG
cttcccacgtggcggagggactggggaccccgggcaccccgtcctgcccttcaccttccagct  (1)
ccgcctcctccgcgcggaccccgccccgtcccgacccctcccgggtccccggcccagcccc
tccgggccctcccagcccctcccttcctttccgcggccccgccctatcctcgcggcgcgag
tttcAGGCAGCGCTGCGTCCTGCTGCGCACGTGG
GGTAGGCGTGTACCGTGGGAGGCCTATATAAGCAGAGCTCGTTTAGTGAACCGTCAGATCGC  (2)
CTGGAGACGCCATCCACGCTGTTTTGACCTCCATAGAAGACACCGGGACCGATCCAGCCTCC
GCGGCCCCGCATTCGAGCTCGGTACCCGG CCCAAGCTTGGG
agcttgagggctcgcatctctccttcacgcgcccgccgccctacctgaggccgccatcca  (3)
cgccggttgagtcgcgttctgccgcctcccgcctgtggtgcctcctgaactgcgtccgccgt
ctaggtaagtttaaagctcaggtcgagaccgggcctttgtccggcgctcccttggagccta
ctagactcagccggctctccacgctttgcctgaccctgcttgctcaactctacgtctttgtt
tcgttttctgttctgcgccgttacagatccaagccacc CCCAAGCTTGGG CGGATCCCG
acc atg gtg agc aag ggc gag gag ctg ttc acc ggg gtg gtg ccc atc  (4)
ctg gtc gag ctg gac ggc gac gta aac ggc cac aag ttc agc gtg tcc
ggc gag ggc gag ggc gat gcc acc tac ggc aag ctg acc ctg aag ttc
atc tgc acc acc ggc aag ctg ccc gtg ccc tgg ccc acc ctc gtg acc
acc ctg acc tac ggc gtg cag tgc ttc agc cgc tac ccc gac cac atg
aag cag cac gac ttc ttc aag tcc gcc atg ccc gaa ggc tac gtc cag
gag cgc acc atc ttc ttc aag gac gac ggc aac tac aag acc cgc gcc
gag gtg aag ttc gag ggc gac acc ctg gtg aac cgc atc gag ctg aag
ggc atc gac ttc aag gag gac ggc aac atc ctg ggg cac aag ctg gag
tac aac tac aac agc cac aac gtc tat atc atg gcc gac aag cag aag
aac ggc atc aag gtg aac ttc aag atc cgc cac aac atc gag gac ggc
agc gtg cag ctc gcc gac cac tac cag cag aac acc ccc atc ggc gac
ggc ccc gtg ctg ctg ccc gac aac cac tac ctg agc acc cag tcc gcc
ctg agc aaa gac ccc aac gag aag cgc gat cac atg gtc ctg ctg gag
ttc gtg acc gcc gcc ggg atc act ctc ggc atg gac gag ctg tac aag
tga CCGCTCGAGCGG GCTCTAGAG

Fig. 59-2

```
GTTTAAACCCGCTGATCAGCCTCGACTGTGCCTTCTAGTTGCCAGCCATCTGTTGTTTGCCC    (5)
CTCCCCCGTGCCTTCCTTGACCCTGGAAGGTGCCACTCCCACTGTCCTTTCCTAATAAAATG
AGGAAATTGCATCGCATTGTCTGAGTAGGTGTCATTCTATTCTGGGGGGTGGGGTGGGGCAG
GACAGCAAGGGGGAGGATTGGGAAGACAATAGCAGGCATGCTGGGGATGCGGTGGGCTCTAT
GG ATGCATCCAATGCATTGGATCAT
cttcccacgtggcggagggactgggggacccgggcacccgtcctgccccttcaccttccagct   (6)
ccgcctcctccgcgcggacccccgccccgtcccgaccccctcccgggtccccggcccagccccc
tccgggccctcccagccccctccccttcctttccgcggcccccgccctctcctcgcggcgcgag
tttcAGGCAGCGCTGCGTCCTGCTGCGCACGTGG TTCCCCGG
```

Amount of protein purified by histidine affinity column
chromatography from 25 mL of culture supernatant

| SGE vector | 3.83mg |
|---|---|
| pTracervector | 0.49mg |

B

Amount of protein collected in terms of 1 L of culture supernatant

| SGE vector | 153.2mg |
|---|---|
| pTracer vector | 19.6mg |

Fig. 67

Amount of protein purified from culture supernatant obtained
after transfection with REIC expression SGE vector

| Amount of protein purified from 520 mL of culture supernatant | 51mg |
|---|---|
| Amount of protein collected in terms of 1 L of culture supernatant | 98mg |

SYSTEM FOR INCREASING GENE EXPRESSION AND VECTOR COMPRISING THE SYSTEM

The instant application contains a Sequence Listing which has been submitted in ASCII format via EFS-WEB and is hereby incorporated by reference in its entirety. Said ASCII copy, created on Mar. 25, 2015, is named sequence.txt and is 64 KB.

TECHNICAL FIELD

The present invention relates to a method for increasing gene expression using promoters, enhancers, and the like, and an expression cassette for increasing gene expression, comprising promoters, enhancers, and the like.

BACKGROUND ART

Various gene expression promoters, such as CMV promoters and CAG promoters, have been developed to increase gene expression efficiency (patent documents 1 to 4). However, the use of these conventional techniques causes daily problems in the field of biotechnology, such as situations in which almost no gene expression takes place or the amount of the thus-expressed protein is extremely low, depending on cell type or gene type. Furthermore, these problems serve as significant barriers to the development of medical science in which gene expression is used for diagnosis or treatment.

Patent document 1 JP Patent Publication No. 2814433
Patent document 2 JP Patent Publication No. 2814434
Patent document 3 U.S. Pat. No. 5,168,062
Patent document 4 U.S. Pat. No. 5,385,839

DISCLOSURE OF THE INVENTION

An object of the present invention is to provide a method for increasing gene expression using promoters, enhancers, and the like, and an expression cassette capable of increasing gene expression, comprising promoters, enhancers, and the like.

The present inventors have attempted to develop a new gene expression system using promoters that allow genes to be expressed with higher efficiency. Specifically, they have compared and examined promoter activity resulting from combinations of promoters and enhancers for various genes. As a result, the present inventors have discovered that a gene can be expressed with high efficiency by causing such gene to be flanked by two promoters or a promoter and an enhancer with the use of a gene expression cassette. The gene expression cassette comprises a DNA construct containing a gene to be expressed and a poly A addition sequence that are located downstream of a $1^{st}$ promoter, as well as an enhancer or a $2^{nd}$ promoter ligated downstream of the DNA construct. The present inventors have further discovered that a gene can be expressed with even higher efficiency by causing the above expression cassette to further contain an element such as a poly A addition sequence, RU5', UAS, or SV40-ori.

Through the development of "a system for increasing gene expression and the vector comprising the system" of the present invention, protein expression can be strongly increased in almost all cells and genes.

The present invention is as follows.

[1] A gene expression cassette, comprising a DNA construct containing a gene to be expressed and a poly A addition sequence that are located downstream of a $1^{st}$ promoter, and further comprising an enhancer or a $2^{nd}$ promoter downstream of the DNA construct.

[2] The expression cassette according to [1], which does not have another mechanism for gene expression downstream of the ligated enhancer or the $2^{nd}$ promoter, but has a structure in which a gene to be expressed is flanked by one $1^{st}$ promoter and one enhancer, or one $1^{st}$ promoter and one $2^{nd}$ promoter.

[3] The expression cassette according to [1], wherein the promoter is selected from the group consisting of a CMV i promoter, an SV40 promoter, an hTERT promoter, a β actin promoter, and a CAG promoter.

[4] The expression cassette according to any one of [1] to [3], wherein the enhancer is at least one enhancer selected from the group consisting of a CMV enhancer, an SV40 enhancer, and an hTERT enhancer.

[5] The expression cassette according to any one of [1] to [4], wherein 1 to 4 CMV enhancers are ligated upstream of the DNA construct containing DNA encoding a protein to be expressed and the poly A addition sequence that are located downstream of the promoter.

[6] The expression cassette according to any one of [1] to [5], comprising at least any one of the following elements:
(i) RU5' ligated immediately upstream of DNA encoding a foreign protein;
(ii) UAS ligated immediately upstream of an enhancer and/or a promoter; and
(iii) SV40-ori ligated to the most upstream portion of the expression cassette.

[7] The expression cassette according to any one of [1] to [6], wherein the gene to be expressed is a therapeutic gene that can be used for the treatment of diseases, or the gene of a protein that can be used for a drug, a diagnostic agent, or a reagent.

[8] The expression cassette according to [7], wherein the therapeutic gene is a cancer suppressor gene that can be used for the treatment of tumors.

[9] The expression cassette according to [8], wherein the cancer suppressor gene is a REIC/Dkk-3 gene.

[10] The expression cassette according to [9], wherein the gene to be expressed is a DNA fragment of the REIC/Dkk-3 gene.

[11] The expression cassette according to [10], wherein the DNA fragment of the REIC/Dkk-3 gene is DNA encoding amino acids 1 to 78 of the amino acid sequence of SEQ ID NO: 18.

[12] The expression cassette for a foreign gene according to [1], having the structure of constructs No. 2 (FIG. 8), No. 4 (FIG. 10), No. 6 (FIG. 12), No. 8 (FIG. 14), No. 10 (FIG. 16), No. 12 (FIG. 18), and No. 14 (FIG. 20).

[13] The expression cassette for a foreign gene according to [1], having the structure of constructs No. 15 (FIG. 16), No. 16 (FIG. 37), No. 17 (FIG. 49), No. 20 (FIG. 57), and No. 21 (FIG. 58).

[14] A vector, comprising the expression cassette for a foreign gene according to any one of [1] to [13].

[15] The vector according to [14], which is an adenovirus vector or an adeno-associated virus vector.

[16] A host cell, containing the vector according to [14] or [15].

[17] A preparation for disease detection or treatment, comprising the vector according to [14] or [15].

[18] A method for expressing a gene to be expressed using the expression cassette according to any one of [1] to [13] or the vector according to [14] or [15].

[19] A method for gene expression, comprising:
ligating an enhancer or a $2^{nd}$ promoter to a site downstream of a DNA construct containing a gene to be expressed and a poly A addition sequence that are located downstream of a $1^{st}$ promoter;
introducing the resultant into a vector, and then expressing the gene using the vector.

[20] A method for producing a protein encoded by a gene to be expressed, comprising introducing the expression cassette according to any one of [1] to [13] or the vector according to [14] or [15] into a cell, and then culturing the cell.

This description includes part or all of the contents as disclosed in the specification and/or drawings of Japanese Patent Application No. 2009-264299, which is a priority document of the present application.

BRIEF DESCRIPTION OF THE DRAWINGS

FIG. 5-1 is a graph showing suppressed proliferation of and induction of cell death in a human prostate cancer PC3 cell line by construct No. 14 into which N78-REIC-coding DNA was inserted (graph).

FIG. 5-2 shows photographs showing suppressed proliferation of and induction of cell death in a human prostate cancer PC3 cell line by construct No. 14 into which N78-REIC-coding DNA was inserted.

FIG. 22-1 shows the full nucleotide sequence of a pDNR-1r Donor vector (SEQ ID NOs: 1 and 2).

FIG. 22-2 shows the full nucleotide sequence of the pDNR-1r Donor vector (SEQ ID NOs: 1 and 2) (a continuation from FIG. 22-1).

FIG. 23 shows the full nucleotide sequence of a pIDT-SMART vector (SEQ ID NOs: 3 and 4.

FIG. 24 shows the nucleotide sequence of a CMV i promoter (hCMV+intron promoter) region (SEQ ID NO: 5).

FIG. 25 shows the nucleotide sequence of a BGH polyA (3×stop+BGH polyA) region (SEQ ID NO: 6).

FIG. 26 shows the nucleotide sequence of a CMV enhancer region (SEQ ID NO: 7).

FIG. 27 shows the nucleotide sequence of a human β actin promoter region (SEQ ID NO:

FIG. 28 shows the nucleotide sequence of RU5' forward {R segment of HTLV Type 1 long terminal repeat and a portion (R-U5') of U5 sequence} region (SEQ ID NO: 9).

FIG. 29 shows the nucleotide sequence of RU5' reverse {R segment of HTLV Type 1 long terminal repeat and a portion (R-U5') of U5 sequence} region (SEQ ID NO: 10).

FIG. 30 shows the nucleotide sequence of a 4×CMV enhancer region (SEQ ID NO: 11).

FIG. 31 shows the nucleotide sequence of a CAG promoter region (SEQ ID NO: 12).

FIG. 32 shows the nucleotide sequence of a 2IRES insert region (SEQ ID NO: 13).

FIG. 33 shows the nucleotide sequence of a SV40ori-UAS-CMVi-RU5' region (SEQ ID NO: 14).

FIG. 34 shows the nucleotide sequence of a 3×stop-BGH-polyA-UAS-hTERT enhancer +SV40 enhancer+CMV enhancer region (SEQ ID NO: 15).

FIG. 35-1 shows the full nucleotide sequence of construct No. 14 vector (SEQ ID NO:

FIG. 35-2 shows the full nucleotide sequence of construct No. 14 vector (SEQ ID NO: 16) (a continuation from FIG. 35-1).

FIG. 37 shows construct No. 16.

FIG. 38 shows the nucleotide sequence of a SV40ori-UAS-SV40 enh-intron A-RU5' region (SEQ ID NO: 19).
FIG. 38 specifically shows the nucleotide sequence of an insertion portion on the left (upstream side) of the insertion gene (gene of interest) in construct No. 15.

FIG. 39 shows the nucleotide sequence of a SV40ori-UAS-hTERT enh-intron A-RU5' region (SEQ ID NO: 20).
FIG. 39 specifically shows the nucleotide sequence of an insertion portion on the left (upstream side) of the insertion gene (gene of interest) in construct No. 16.

FIG. 40 shows the nucleotide sequence of the GFP region in a plasmid (SEQ ID NO: 21).

FIG. 41-1 shows the nucleotide sequence of a plasmid in which the DNA of a GFP gene was inserted into the insertion gene (gene of interest) region in construct No. 14 (SEQ ID NO:

FIG. 41-2 shows the nucleotide sequence of the plasmid in which the DNA of the GFP gene was inserted into the insertion gene (gene of interest) region in construct No. 14 (SEQ ID NO: 22) (a continuation from FIG. 41-1).

FIG. 42-1 shows the nucleotide sequence of the plasmid in which the DNA of the GFP gene was inserted into the insertion gene (gene of interest) region in construct No. 15 (SEQ ID NO: 23).

FIG. 42-2 shows the nucleotide sequence of the plasmid in which the DNA of the GFP gene was inserted into the insertion gene (gene of interest) region in construct No. 15 (SEQ ID NO: 23) (a continuation from FIG. 42-1).

FIG. 43-1 shows the nucleotide sequence of the plasmid in which the DNA of the GFP gene was inserted into the insertion gene (gene of interest) region in construct No. 16 (SEQ ID NO: 24).

FIG. 43-2 shows the nucleotide sequence of the plasmid in which the DNA of the GFP gene was inserted into the insertion gene (gene of interest) region in construct No. 16 (SEQ ID NO: 24) (a continuation from FIG. 43-1).

FIG. 45 shows the nucleotide sequence of a human erythropoietin region in a plasmid (SEQ ID NO: 25).

FIG. 47A shows the nucleotide sequence of a human IgG light chain region (FIG. 44A) in a plasmid (SEQ ID NO: 26).

FIG. 47B shows the nucleotide sequence of a human IgG heavy chain region (FIG. 44B) in a plasmid (SEQ ID NO: 27).

FIG. 50 shows the nucleotide sequence of a plasmid in which the DNA of full-length human REIC was inserted into the insertion gene (gene of interest) region in construct No. 17 (SEQ ID NO: 28).

FIG. 52 shows the sequence of a c-myc gene (SEQ ID NO: 29).

FIG. 53 shows the nucleotide sequence prepared by linking BGH polyA existing downstream of an expression gene in expression plasmid construct No. 14 and 3 enhancers (SEQ ID NO: 30

FIG. 59-1 shows the nucleotide sequence of a plasmid in which the DNA of a GFP gene was inserted into the insertion gene (gene of interest) region of construct No. 21 (SEQ ID NO: M.

FIG. 59-2 shows the nucleotide sequence of the plasmid in which the DNA of the GFP gene was inserted into the insertion gene (gene of interest) region of construct No. 21 (SEQ ID NO: 31) (a continuation from FIG. 59-1).

FIG. 64 shows the amounts of human erythropoietin produced using the expression vectors of the present invention. FIG. 64A shows the amount of the same produced in 25 mL of each culture supernatant and FIG. 64B shows the amount of the same produced in terms of 1 L of the culture supernatant.

FIG. 67 shows the amounts of a human REIC protein produced using the expression vector of the present invention (the amount of the protein produced in 520 mL of the culture supernatant and the amount of the protein produced in terms of 1 L of the culture supernatant).

BEST MODE OF CARRYING OUT THE INVENTION

Figure 1:
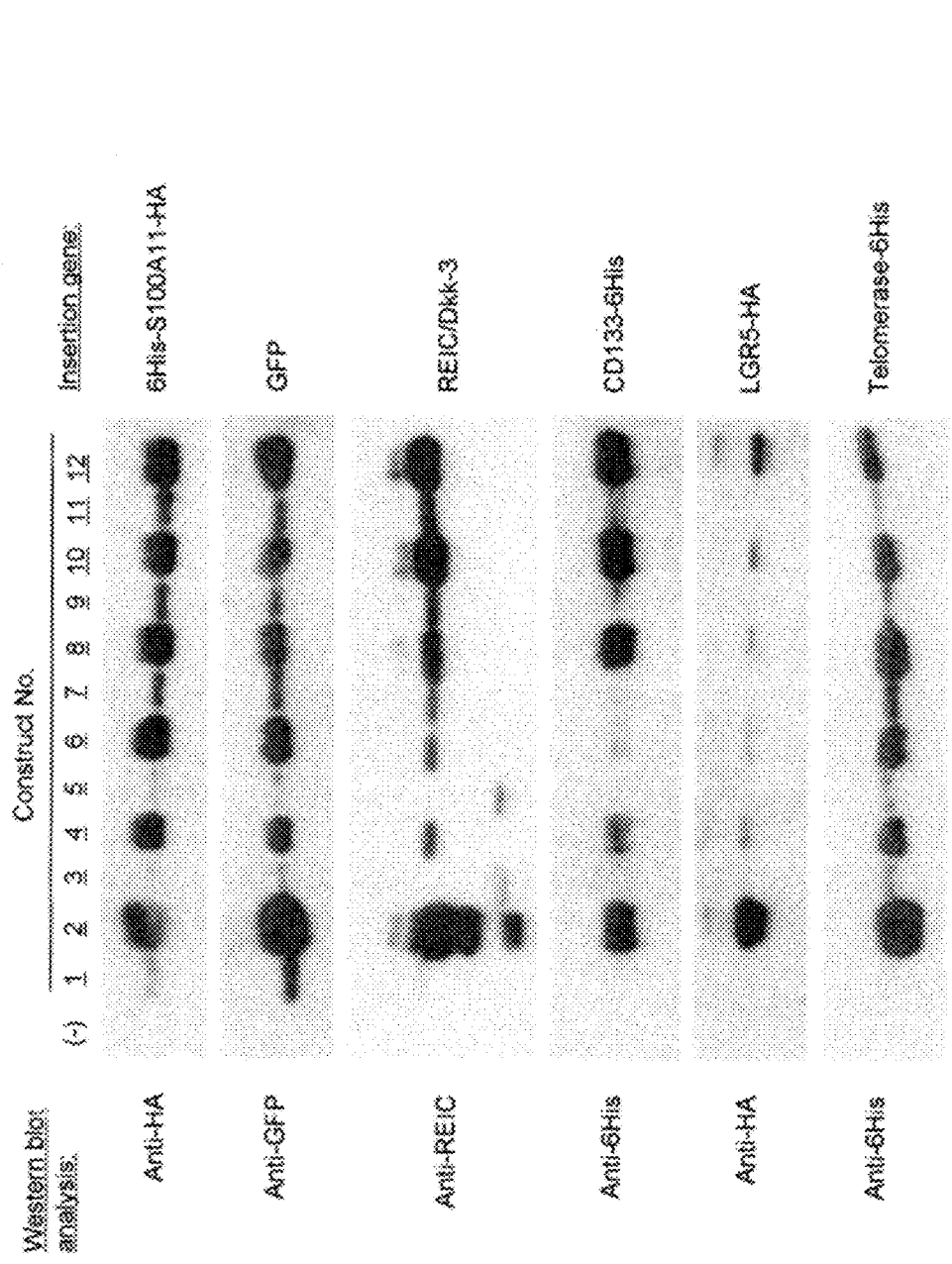
FIG. 1 shows the expression of various foreign genes transfected for 36 hours into a HEK293 cell line using FuGENE (trademark)-HD.

The present invention will be described in detail as follows.

In the present invention, the term "an expression cassette for a protein to be expressed" refers to a DNA set for enabling the expression of a protein to be expressed.

The expression cassette has a structure in which a DNA construct contains the gene of a protein to be expressed (gene to be expressed) and a poly A addition sequence that are located downstream of at least a $1^{st}$ promoter, and an enhancer or a $2^{nd}$ promoter is ligated downstream of the DNA construct. Also, any gene can be used as a gene to be expressed. In the expression cassette of the present invention, a site into which a gene to be expressed is inserted may exist as a multicloning site. In this case, a gene to be expressed may be inserted into such a multicloning site (insertion site) using a sequence that is recognized by a restriction enzyme. Such an expression cassette that does not comprise the gene (DNA) itself to be expressed but comprises a site into which the DNA is inserted as a multicloning site is included in examples of the expression cassette of the present invention. In addition, a gene to be expressed may be referred to as a target gene or a gene of interest and a protein to be expressed may also be referred to as a target protein or a protein of interest. Also, in view of the construction of the expression cassette, these genes are also referred to as insertion genes, since they are inserted into regions of target genes in the expression cassette. Alternatively, these genes may also be referred to as foreign genes.

Furthermore, the above enhancer or the $2^{nd}$ promoter is present at the most downstream site of the expression cassette of the present invention, and no mechanism for gene expression is present downstream thereof. Specifically, the expression cassette of the present invention has a structure in which at least a gene to be expressed is flanked by one $1^{st}$ promoter and at least one enhancer, or a gene to be expressed is flanked by the one $1^{st}$ promoter and the one $2^{nd}$ promoter. Here, the term "(another) mechanism for gene expression" refers to a mechanism for expression of a gene other than the above gene to be expressed, which comprises a promoter, an enhancer, and the like for expression of such a gene other than the gene to be expressed. In the expression cassette of the present invention, promoters can be present downstream and upstream of a gene to be expressed. These two promoters are used for enhancement of the expression efficiency of the gene to be expressed.

The expression cassette of the present invention is incorporated into an expression vector and then used. The present invention also encompasses such a vector containing the expression cassette of the present invention. As described above, the above enhancer or $2^{nd}$ promoter is present at the most downstream site of the expression cassette of the present invention, and a mechanism for gene expression does not exist downstream thereof. A vector containing the expression cassette of the present invention does not have any mechanism for gene expression at a site downstream of the expression cassette.

In the present invention, examples of a gene to be expressed include an artificially inserted gene (DNA) encoding a foreign protein. Examples of the same also include such a gene from an origin differing from that of a host cell and a gene from the same origin as that of a host cell. In this case, in the present invention, such a foreign gene is also referred to as an insertion gene. Types of gene to be expressed are not limited. DNAs encoding all proteins from which recombinants are produced and DNAs encoding proteins to be expressed in vivo so as to be used for the treatment of specific diseases can be used. Moreover, examples of therapeutic genes that can be used for the treatment of specific diseases include an REIC/Dkk-3 gene (the nucleotide sequence thereof is shown in SEQ ID NO: 17), tumor suppressor genes such as p53 and Rb, and genes encoding proteins that can be used as drugs such as biologically active substances (e.g., interleukin 1 (IL-1), IL-2, IL-3, IL-4, IL-5, IL-6, IL-7, IL-8, IL-9, IL-10, IL-11, IL-12, IL-13, IL-14, IL-15, α-interferon, β-interferon, γ-interferon, angiostatin, thrombospondin, endostatin, METH-1, METH-2, GM-CSF, G-CSF, M-CSF, a tumor necrosis factor, a hepatocyte growth factor, erythropoietin, thrombopoietin, insulin, growth hormone, antibody (IgG light chain or IgG heavy chain), protein G, and protein A), genes encoding proteins useful as diagnostic agents to be used for detection of diseases and the like or reagents to be used for experiments, studies, and the like at laboratories. A target protein to be expressed is preferably an extracellular secretory protein. Also, through artificial ligation of an enhancer or a promoter to a site downstream of an original gene of an organism, the expression of such an original gene of an organism can also be enhanced. Specifically, examples of a gene to be expressed in the present invention include original genes of organisms. The present invention further encompasses the insertion of an enhancer or a promoter to a site downstream of an original gene of an organism, so as to control the expression of the gene. The present invention further encompasses a cell into which an enhancer or a promoter is inserted downstream of an original gene (of the relevant organism). Further examples of a gene to be expressed include DNA and the like encoding siRNA, shRNA, miRNA, and the like having RNA interference action. When RNA having RNA interference action is used, such RNA is transcribed and produced using a transfer RNA promoter, so that the suppressed expression of a specific gene becomes possible.

For example, of these genes, a REIC/Dkk-3 gene and the like can be used for the treatment of tumors. Specifically, not only a full-length gene thereof, but also a fragment thereof can be used. An example thereof is DNA encoding a polypeptide that consists of the amino acid sequence starting from amino acid 1 and terminating at any one of amino acids 39 to 78 in the amino acid sequence of the REIC/Dkk-3 protein shown in SEQ ID NO: 18 or an amino acid sequence that has a substitution, a deletion, or an addition of 1 or several amino acids with respect to the amino acid sequence starting from amino acid 1 and terminating at any one of amino acids 39 to 78 in the amino acid sequence of the REIC/Dkk-3 protein shown in SEQ ID NO: 18, and has apoptotic activity. Among such DNAs, DNA (N78-REIC DNA) encoding a peptide consisting of amino acids 1 to 78 of the amino acid sequence of the REIC/Dkk-3 protein shown in SEQ ID NO: 18 is preferably used.

A reporter gene may also be contained for detection or diagnosis of disease.

A promoter is a specific nucleotide sequence on DNA for initiation of transcription with the DNA as a template, and generally has a common sequence. For example, prokaryotes such as *Escherichia coli* generally has a TATAATG sequence at a 10-base-pair site that is a transcription initiation site, and a TTGACA sequence at a 35-base-pair site. Furthermore, eukaryotes generally have a TATA box at a 20-base-pair site. The expression cassette of the present invention may always have a $1^{st}$ promoter at a site upstream of a gene to be expressed and may have a $2^{nd}$ promoter at a site downstream of the gene to be expressed. These promoters to be used as the $1^{st}$ promoter and the $2^{nd}$ promoter are not limited and the $1^{st}$ promoter and the $2^{nd}$ promoter may be the same or different from each other. Non specific promoters that can accelerate the expression of foreign genes in all cells or tissues, tissue- or organ-specific promoters, tumor-specific promoters, and specific or selective promoters such as development- or differentiation-specific promoters can also be used herein. For example, a specific promoter can be used as the $1^{st}$ promoter and a non specific promoter can be used as the $2^{nd}$ promoter. Promoters to be used in the present invention are as follows. Examples of a cancer- or tumor-specific promoter include hTERT (human telomerase reverse transcriptase), PSA (prostate-specific antigen), c-myc, and a GLUT promoter. Examples of an ES cell- or cancer stem cell-specific promoter include OCT3/4 and NANOG promoters. An example of a neural stem cell-specific promoter is a Nestin promoter. Examples of a cell stress sensitive promoter include HSP70, HSP90, and p53 promoters. An example of a hepatocyte-specific promoter is an albumin promoter. An example of a radiosensitive promoter is a TNF-alpha promoter. An example of a promoter for increasing the number of copies of an infection plasmid is a SV40 promoter and the like. An example of a proliferative cell-specific promoter is an EF1-alpha promoter. Further specifically, for example, as the $1^{st}$ promoter, a CMV-i promoter (hCMV+intron promoter) (SEQ ID NO: 5), a β actin promoter, a CAG promoter (SEQ ID NO: 12), a CMV promoter, or the like is used and as the $2^{nd}$ promoter, a CMV promoter or the like is used. Animal species from which a β actin promoter is derived is not limited. Mammalian β actin promoters such as a human β actin promoter (SEQ ID NO: 8) and a chicken actin promoter are used. Furthermore, an artificial hybrid promoter such as the above CMV-i promoter can also be used. The CMV-i promoter can be synthesized based on the disclosure in the specification of U.S. Pat. No. 5,168,062 or the specification of U.S. Pat. No. 5,385,839. As such a promoter, a core promoter portion consisting of a minimum sequence having promoter activity may be used. The term "core promoter" refers to a promoter region capable of functioning to result in precise transcription initiation, which may contain a TATA box. Among the above promoters, a cancer- and/or tumor-specific promoter such as an hTERT promoter can be preferably used for cancer-targeting gene therapy or diagnosis of cancer with the use of gene expression. Construct No. 21 comprising the hTERT promoter can be used for such purposes.

The origin of a poly A addition sequence (polyadenylation sequence, polyA) is not limited. Examples of such a poly A addition sequence include a growth hormone gene-derived poly A addition sequence such as a bovine growth hormone gene-derived poly A addition sequence (contained in the nucleotide sequence shown in SEQ ID NO: 6 (a sequence following the $13^{th}$ base)) and a human growth hormone gene-derived poly A addition sequence, an SV40 virus-derived poly A addition sequence, and a human or rabbit β globin gene-derived poly A addition sequence. Containment of such a poly A addition sequence in the expression cassette results in increased transcription efficiency.

Examples of an enhancer are not limited, as long as it results in an increased amount of messenger RNA (mRNA) generated by transcription. An enhancer is a nucleotide sequence having an effect of accelerating the action of a promoter and generally has a length of around 100 bp in most cases. An enhancer can accelerate transcription regardless of the direction of the relevant sequence. One type of enhancer can be used in the present invention. Specifically, two or more (a plurality of) same enhancers may be used or a plurality of different enhancers may be used in combination. Also, when a plurality of different enhancers are used, the order thereof is not limited. For example, a CMV enhancer (SEQ ID NO: 7), an SV40 enhancer, an hTERT (Telomerase Reverse Transcriptase) enhancer, and the like can be used. An example thereof is a product resulting from linking of the hTERT enhancer, the SV40 enhancer, and the CMV enhancer in such order.

Moreover, a plurality of enhancers (e.g., 1 to 4 enhancers) may be ligated upstream of a DNA construct comprising DNA encoding a protein to be expressed and a poly A addition sequence. Enhancers to be ligated upstream thereof are not limited, and a CMV enhancer is preferable. An example thereof is 4×CMV enhancer (SEQ ID NO: 11) prepared by linking four CMV enhancers.

When an enhancer is inserted immediately downstream of a DNA construct consisting of "promoter—gene to be expressed—poly A addition sequence," the protein of the gene (to be expressed more strongly) can be expressed than that in the case of a general conventional gene expression system.

In particular, through the use of a combination of a CMV i promoter and a CMV enhancer, in almost all cells (host cells), strong protein expression of a gene to be expressed becomes possible regardless of the type of transfection reagent used herein, although any gene is inserted.

Insertion of one or more CMV enhancers into sites upstream of a promoter results in further enhanced expression of a specific gene (e.g., a REIC/Dkk-3 gene or a CD133 gene in Examples below) in specific cells (e.g., a HEK293 cell line or a MCF7 cell line in Examples below). Also, four CMV enhancers are inserted upstream of a promoter, so that the expression is further enhanced depending on specific cells (e.g., a HepG2 cell line or a HeLa cell line in Examples below).

Figure 2:
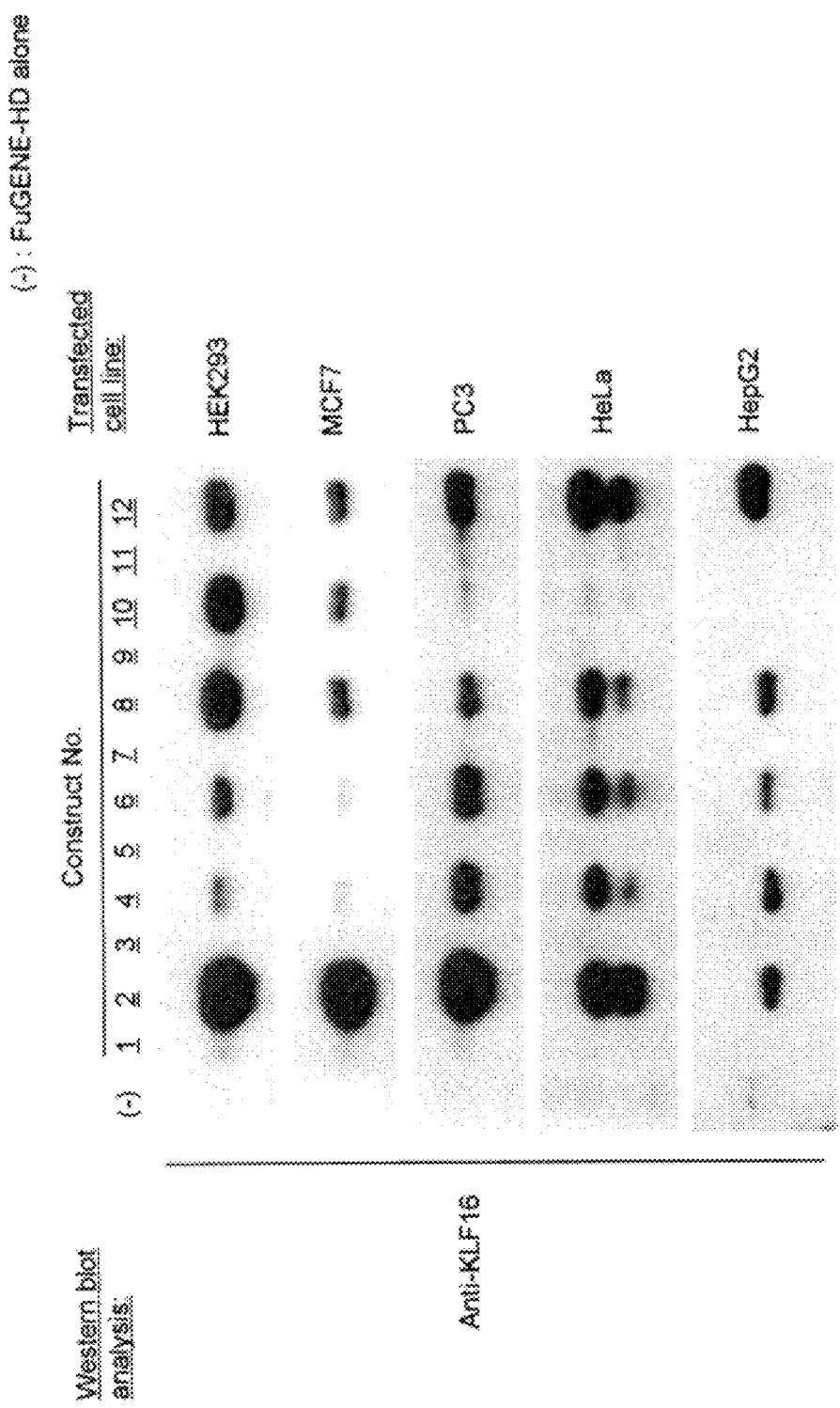
FIG. 2 shows the expression of a KLF gene transfected for 36 hours into various cell lines using FuGENE (trademark)-HD.

In addition, insertion alone of a CMV enhancer to a site upstream of a promoter results in only slightly increased gene expression or a slight change therein (FIG. 1 and FIG. 2). It is important for the expression cassette of the present invention that a CMV enhancer is inserted and ligated immediately downstream of a poly A addition sequence.

Furthermore, RU5' (SEQ ID NO: 9) may be ligated immediately upstream of DNA encoding a protein to be expressed. The expression " . . . (to a site) immediately upstream of" means that the relevant sequence is directly ligated via no other elements having specific functions. However, a short sequence may be contained between them, as a linker. RU5' is HTLV-derived LTR and is an element that increases protein expression through insertion thereof (Mol. Cell. Biol., Vol. 8 (1), p. 466-472, 1988). Insertion of RU5' in a direction opposite to that reported previously may cancel the promoter's effect of enhancing expression due to enhancer insertion.

Furthermore, UAS may be ligated to a site immediately upstream of an enhancer and/or a promoter. UAS is a binding region for a GAL4 gene. Insertion of a GAL4 gene into a site downstream of UAS can result in increased protein expression.

Moreover, SV40-ori may be ligated to the most upstream portion of the expression cassette. SV40-ori is a binding region for an SV40 gene. Insertion of an SV40 gene into a site downstream of SV40-ori results in increased protein expression.

Each of the above elements should be functionally ligated. Here, the term "functionally ligated" means that each element is ligated so that it can exhibit its functions and thus the expression of a gene to be expressed is enhanced.

Figure 36:
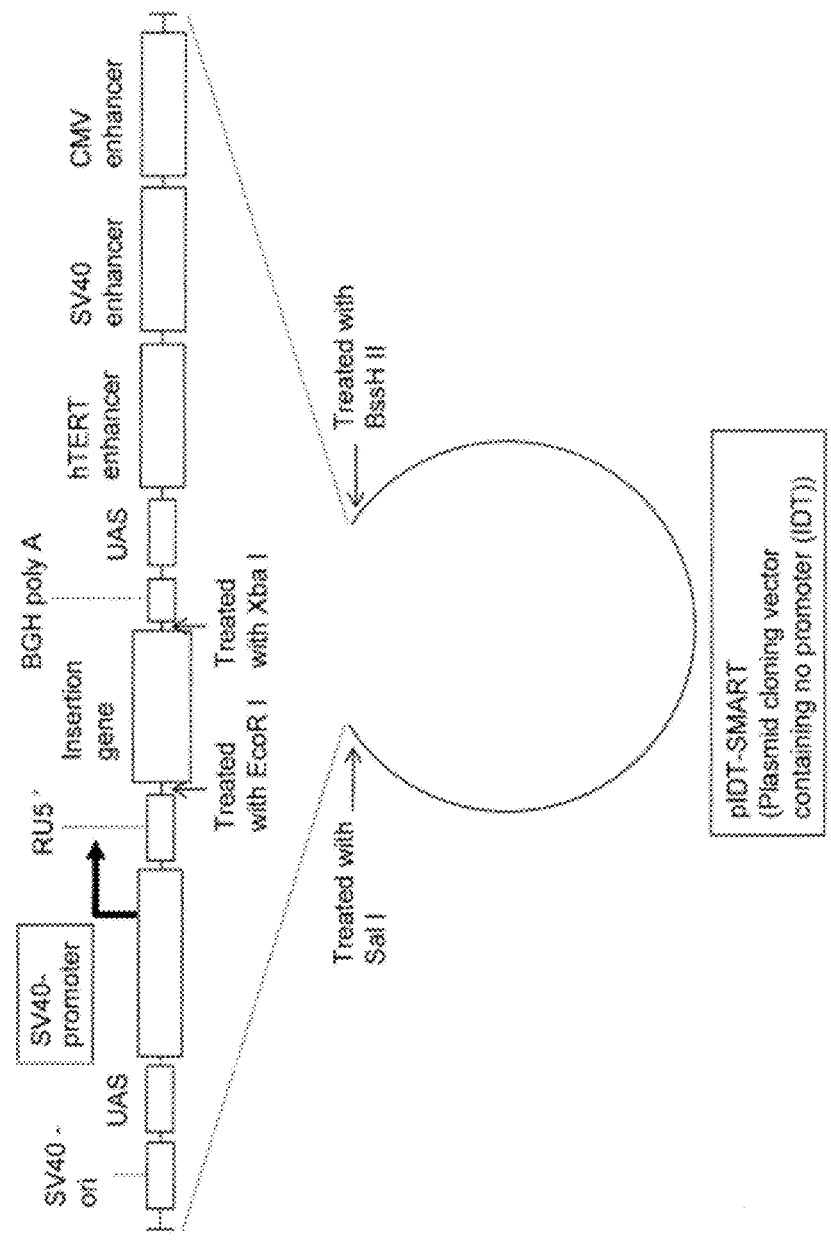
FIG. 36 shows construct No. 15.
Figure 57:
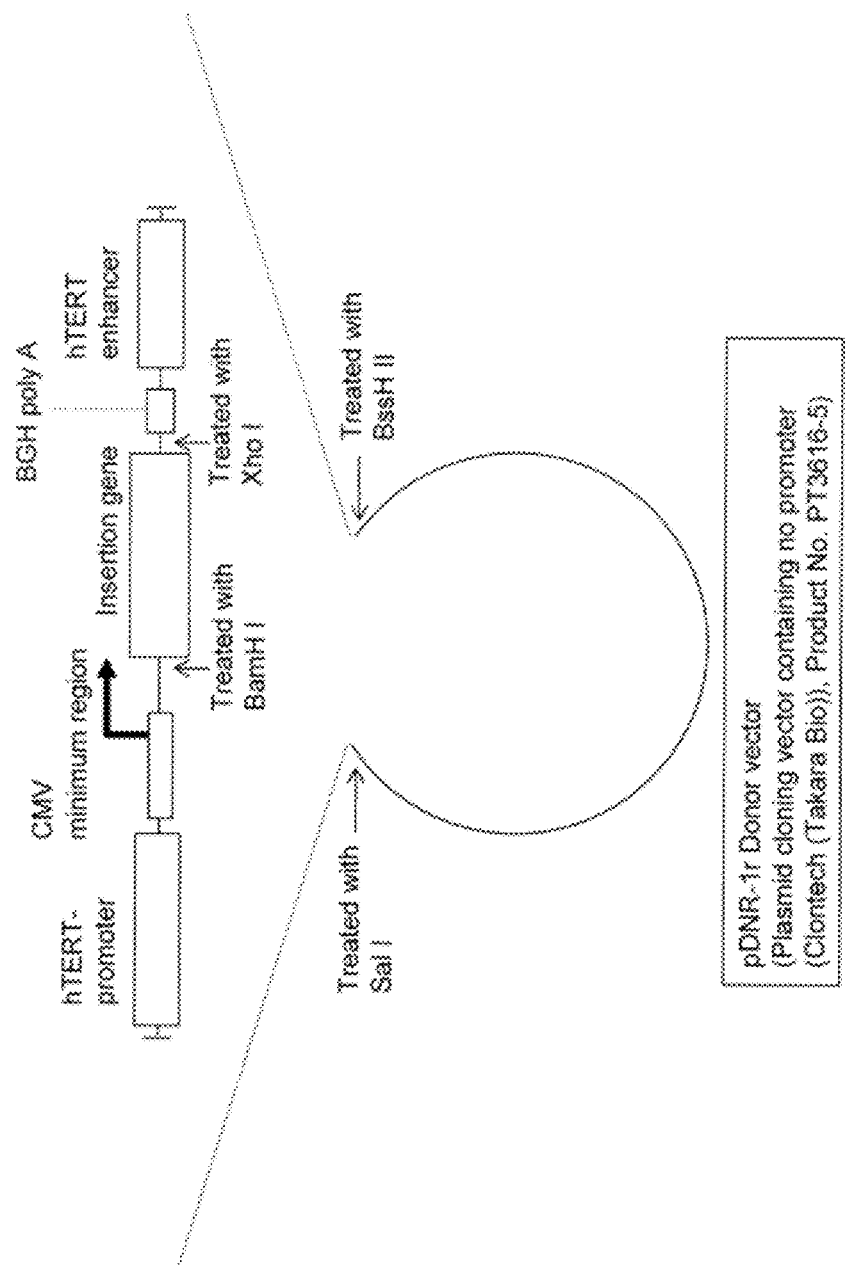
FIG. 57 shows the structure of construct No. 20.
Figure 58:
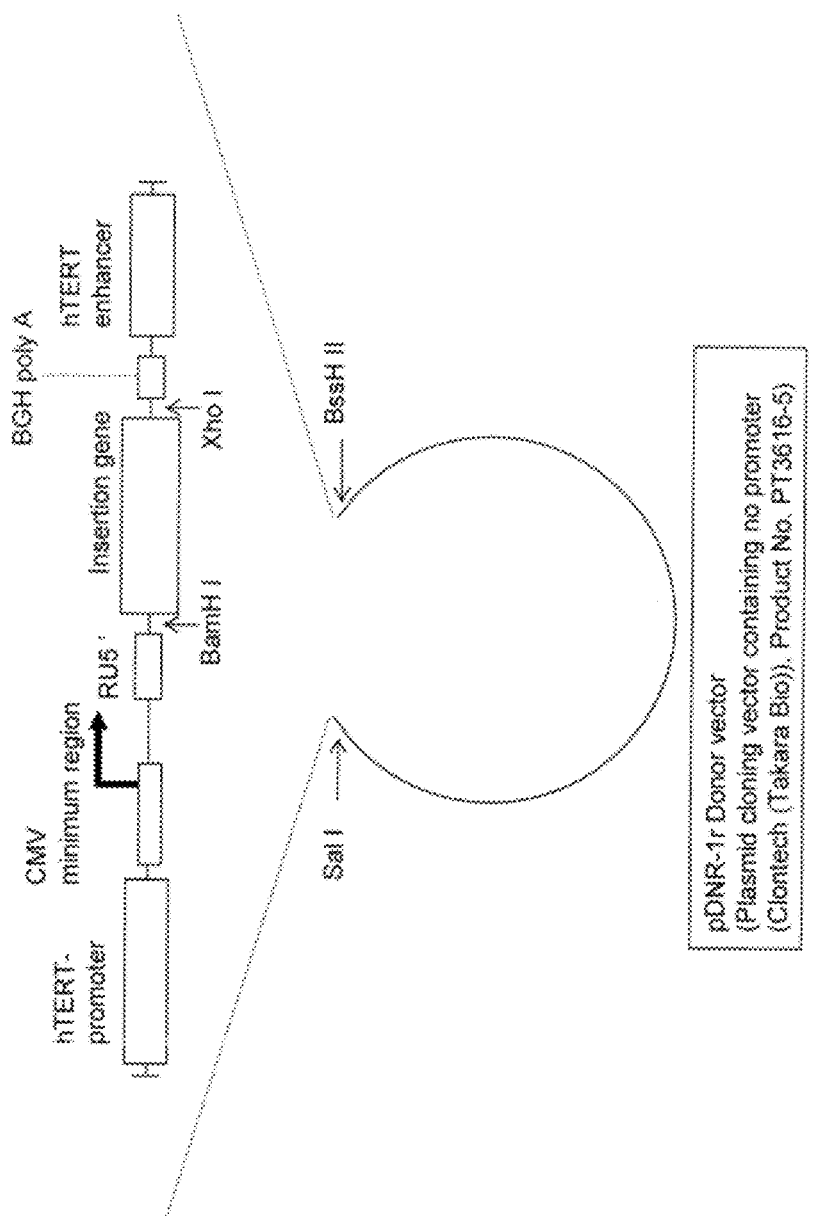
FIG. 58 shows the structure of construct No. 21.

FIG. 7 to FIG. 21, FIG. 36, FIG. 37, FIG. 49, and FIG. 55 to FIG. 58 show various expression cassette constructs. In the present invention, such a construct may also be referred to as the backbone of a plasmid. Examples of the constructs of the present invention for enhancing the expression of genes to be expressed include construct No. 2 (FIG. 8), construct No. 4 (FIG. 10), construct No. 6 (FIG. 12), construct No. 8 (FIG. 14), construct No. 10 (FIG. 16), construct No. 12 (FIG. 18), construct No. 14 (FIG. 20), construct No. 15 (FIG. 36), construct No. 16 (FIG. 37), construct No. 17 (FIG. 49), construct No. 20 (FIG. 57), and construct No. 21 (FIG. 58). Another example thereof is a construct shown in FIG. 21.

Among these constructs, with the object of increasing gene expression, construct No. 14, construct No. 15, and construct No. 16 are the best, in which 3 enhancers are ligated downstream of each gene of interest. For example, as a result of the use of a full-length REIC gene as a gene of interest in construct No. 14, the protein expression level is equivalent to that in the case of an adenovirus vector (100 MOI, encoding the full-length REIC/Dkk-3 gene). Also, the plasmid backbone of construct No. 14 exhibits an effect of increasing gene expression even in the case of a gene fragment such as DNA encoding N78-REIC.

For example, through transfection of human prostate cancer cells (PC3) with a preparation in which construct No. 14 contains a DNA fragment encoding N78-REIC, significant effects of suppressing the proliferation of cancer cells and significant effects of inducing cancer cell death are observed. Through transfection of human prostate cancer cells (PC3) with a preparation in which a full-length REIC gene is encoded in construct No. 14, effects of suppressing the proliferation of cancer cells are observed.

Furthermore, DNA encoding a protein such as human erythropoietin is inserted into construct No. 14, an expression vector is constructed, and then cells are transfected with the expression vector, and thus the protein can be produced in a large amount using the cells.

In the present invention, DNAs represented by the nucleotide sequences shown in the above SEQ ID NOs may have a mutation(s) in the nucleotide sequences, as long as they retain the activity of each DNA or the activity of the protein or the polypeptide encoded by each DNA. Examples of such a DNA that can be used for construction of the DNA construct of the present invention include DNA hybridizing under stringent conditions to DNA having a nucleotide sequence complementary to the nucleotide sequence shown in each SEQ ID NO, DNA having at least 85%, preferably at least 90%, further preferably at least 95%, and particularly preferably at least 97% homology with the nucleotide sequence shown in each SEQ ID NO as calculated using BLAST (Basic Local Alignment Search Tool at the National Center for Biological Information (NCBI)) or the like (for example, using default; that is, initially set parameters), and DNA encoding a protein or a polypeptide comprising an amino acid sequence having a substitution, a deletion and/or an addition of one or a plurality of or several (1 to 10, preferably 1 to 5, further preferably 1 or 2 amino acids) amino acids with respect to the amino acid sequence of the protein or the polypeptide encoded by the DNA. The term "stringent conditions" used herein refers to, for example, stringent conditions of about 1×SSC, 0.1% SDS, and 37° C., more stringent conditions of about 0.5×SSC, 0.1% SDS, and 42° C., or even more stringent conditions of about 0.2×SSC, 0.1% SDS, and 65° C. Under more stringent hybridization conditions, accordingly, isolation of DNA having higher homology to a probe sequence can be expected. It should be noted that the above combinations of SSC, SDS, and temperature conditions are examples, and necessary stringency can be realized by adequately combining a DNA concentration, a DNA length, a hybridization reaction time, and other conditions.

Examples of a vector for insertion of the expression cassette of the present invention include viral vectors such as a plasmid, an adenovirus vector, an adeno-associated virus vector, a lentivirus vector, a retrovirus vector, a herpes virus vector, and Sendai virus vector and non-viral vectors such as a biodegradable polymer. A vector into which the above expression cassette has been introduced may be introduced into cells by a known technique such as infection or electroporation.

At this time, the vector may also be introduced using a known transfection reagent.

A vector constructed by insertion of the expression cassette of the present invention is introduced into cells for transfection, so that a gene of interest can be expressed in the cells and the protein of interest can be produced. For introduction of the expression cassette of the present invention and production of a target protein, eukaryotic cell lines or prokaryotic cell lines can be used. Examples of eukaryotic cells include cells of established mammalian cell lines, cells of insect cell lines, fungal cells or filamentous bacterial cells, and yeast cells. Examples of prokaryotic cells include cells of bacteria such as *Escherichia coli, Bacillus subtilis*, and *Brevibacillus brevis*. Preferably, mammalian cells such as Hela cells, HEK193 cells, CHO cells, COS cells, BHK cells, or Vero cells are used. The above transformed host cells are cultured in vitro or in vivo, so that a protein of interest can be produced. Host cells are cultured by a known technique. For example, a known culture medium such as DMEM, MEM, RPMI1640, or IMDM can be used as a culture solution. The thus expressed protein can be purified by a known technique from a culture solution when it is a secretory protein or from a cell extract when it is a non-secretory protein. When a protein of interest is expressed and produced, the protein can also be produced by simultaneous transfection of cells with a plurality of vectors containing different genes of interest. With the use of such a technique, a plurality of proteins can be produced simultaneously.

Furthermore, a commercial vector may be modified to contain the expression cassette of the present invention. For example, an enhancer is incorporated into a region downstream of the expression gene cassette in a commercial vector such as pShuttle vector and then the vector can be used. Examples of the vector of the present invention include commercial cassettes that have been modified.

The present invention further encompasses an adenovirus (Ad) vector and an adeno-associated virus (AAV) vector containing the above expression cassettes for genes to be expressed. The vectors enable specific diagnosis or treatment of disease such as cancer. The vectors can be constructed by insertion of the above expression cassette for genes to be expressed into an adenovirus or an adeno-associated virus.

Adenovirus vectors are characterized in that: (1) transfection can be performed in a variety of cells; (2) transfection can be efficiently performed even for cells at the stationary phase; (3) they can be concentrated by centrifugation such that a virus with a high titer (10 to 11 PFU/ml or more) can be obtained; and (4) they are appropriate for use in direct transfection into in vivo tissue cells.

As an adenovirus vector to be used for gene therapy, the following vectors have been developed: a second generation adenovirus vector (Lieber, A., et al., J. Virol., 70, 8944, 1996; Mizuguchi, H. & Kay, M. A., Hum. Gene Ther., 10, 2013, 1999) obtained by deleting the E2 or E4 domain in addition to the E1/E3 domain from a first generation adenovirus vector (Miyake, S., et al., Proc. Natl. Acad. Sci. U.S.A., 93, 1320, 1996) lacking the E1/E3 domain; and a third generation adenovirus vector (Steinwaerder, D. S. et al., J. Virol., 73, 9303, 1999) almost completely lacking the adenovirus genome (GUTLESS). However, for transfection of the gene according to the present invention, any adenovirus vector may be used without particular limitation.

Adeno-associated virus is a single-stranded DNA virus of the genus *Parvovirus*, which is characterized in that: (1) it undergoes long-term gene expression; (2) it exhibits low toxicity; and (3) it enables transfection of dividing and non-dividing cells. Concatamer (complex prepared by ligation of single-stranded DNAs) formation is thought to allow long-term gene expression.

An adenovirus (Ad) vector and an adeno-associated virus (AAV) vector containing the expression cassette of the present invention for a gene to be expressed and enables expression of the target gene to be expressed can be used for detection or treatment of disease. An example of disease is cancer. With the use of a peptide (inserted into the outer shell of an adenovirus vector or an adeno-associated virus vector) such as RGD selectively binding to a protein expressed in specific cells, the vector is directed to the cells. The cells are infected and the gene to be expressed is expressed. When a gene to be expressed is a reporter gene such as a luciferase gene, specific cells can be detected with light emission or the like. When specific cells are cancer cells, through administration of the vector to a subject, cancer cells in the subject can be detected and then the subject can be diagnosed as having or not having cancer. A single cell can be detected by the adenovirus vector and the adeno-associated virus vector of the present invention, and thus they can be used for detection of micro cancer, for example.

Furthermore, when a gene to be expressed is a therapeutic gene, such a target gene to be expressed is expressed in specific cells, so that it can exhibit therapeutic effects. For example, when specific cells are cancer cells and a cancer suppressor gene such as a REIC/Dkk-3 gene is used, through administration thereof to a subject, such a cancer therapeutic gene is delivered to cancer cells of the subject, the gene is expressed in cancer cells, and thus it exhibits therapeutic effects. The present invention encompasses a diagnostic or therapeutic viral preparation containing such an adenovirus vector or adeno-associated virus vector. Examples of cancer to be treated in the present invention when a cancer suppressor gene such as a human REIC/Dkk-3 gene is used as a therapeutic gene include cranial nerve tumor, skin cancer, gastric cancer, lung cancer, hepatic cancer, lymphoma/leukemia, colon cancer, pancreatic cancer, anal/rectal cancer, esophageal cancer, uterine cancer, breast cancer, adrenal cancer, kidney cancer, renal pelvic and ureteral cancer, bladder cancer, prostate cancer, urethral cancer, penile cancer, testicular cancer, osteoma/osteosarcoma, leiomyoma, rhabdomyoma, and mesothelioma. The adenovirus vector and the adeno-associated virus vector of the present invention can also be used for treatment of primary cancer and metastatic cancer.

The adenovirus vector and the adeno-associated virus vector of the present invention can be administered by methods that can be employed in the field of gene therapy, such as intravascular administration (e.g., intravenous administration and intraarterial administration), peroral administration, intraperitoneal administration, intratracheal administration, intrabronchial administration, subcutaneous administration, or transdermal administration. In particular, the adenovirus vector and the adeno-associated virus vector of the present invention have strong directivity to specific tissues or cells, which allows them to efficiently deliver a target gene to specific tissues or cells. Hence, efficient diagnosis and treatment are possible by intravenous administration of the adenovirus vector and the adeno-associated virus vector.

The adenovirus vector or the adeno-associated virus vector may be administered in a therapeutically effective dose. The therapeutically effective dose thereof can be easily determined by persons skilled in the field of gene therapy. Furthermore, dosage can be adequately varied depending on the severity of the pathological conditions, gender, age, body weight, common practice, and the like of a subject. For example, the adenovirus vector or the adeno-associated virus vector may be administered at $0.5 \times 10^{11}$ to $2.0 \times 10^{12}$ viral genome/kg body weight, preferably at $1.0 \times 10^{11}$ to $1.0 \times 10^{12}$ viral genome/kg body weight, and further preferably at $1.0 \times 10^{11}$ to $5.0 \times 10^{11}$ viral genome/kg body weight. A viral genome is represented by the molecularity (number of viral particles) of the adenovirus or the adeno-associated virus genome, and may also be referred to as "particle(s)." The vector contains a carrier, a diluent, and an excipient that are generally used in the field of pharmaceutical preparation. For example, as carriers for tablets and as excipients, lactose, magnesium stearate, and the like are used. As an aqueous liquid for injection, saline or an isotonic solution containing dextrose and other adjuvants is used, for example. Such a solution may be used in combination with an appropriate solubilizing agent, such as alcohol, polyalcohol (e.g., propylene glycol), or a nonionic surfactant. As an oily fluid, sesame oil, soybean oil, or the like is used. As a solubilizing agent, such as benzyl benzoate or benzyl alcohol may be used in combination.

Moreover, an expression vector that contains the expression cassette of the present invention comprising a gene of interest can also be used as a vaccine or a DNA vaccine for cancer and the like (Kaufman, H. L. et al., J. Clin. Oncol. 22, 2122-2132 (2004); McNeel, D. G. et al., J. Clin. Oncol. 27, 425-430 (2009)). For example, an expression vector that contains the expression cassette of the present invention in which a gene encoding a target cancer-specific antigen protein has been incorporated is administered in vivo via subcutaneous injection or the like, the antigen is expressed in vivo, and thus the activation of a host's cellular immunity or antibody immunity against the antigen can be induced. The expression cassette of the present invention can be used for prevention or treatment of disease such as cancer through the use thereof as a vaccine as described above.

The present invention is hereafter described in detail with reference to the following examples, although the present invention is not limited thereto.

Example 1

Expression Cassette Comprising CMV Promoter

Figure 7:
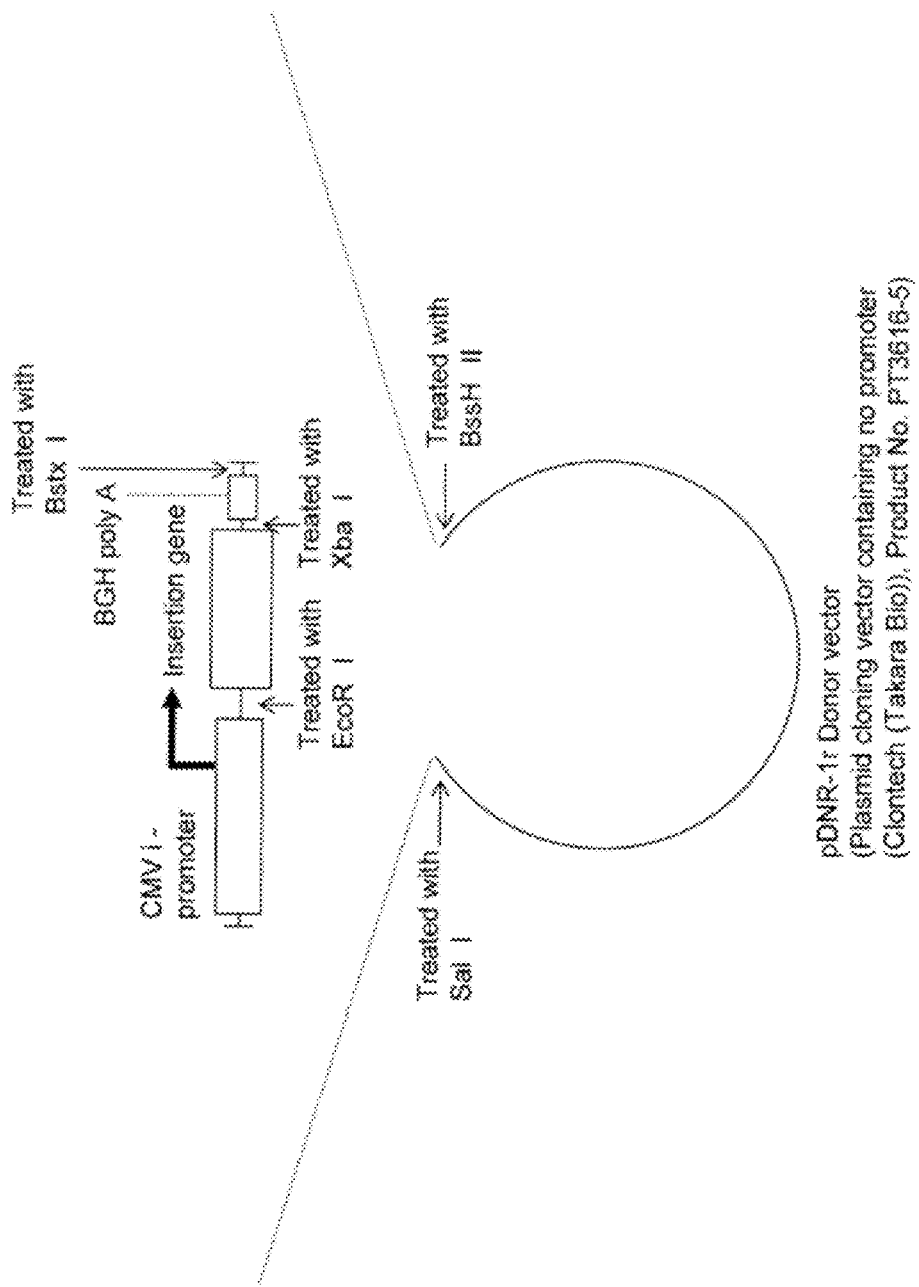
FIG. 7 shows the structure of construct No. 1.

The expression cassettes of the present invention were prepared and then transfected. The thus expressed proteins were analyzed by Western blotting.
(1) Expression Cassette Constructs
Construct No. 1 (FIG. 7)

Figure 8:
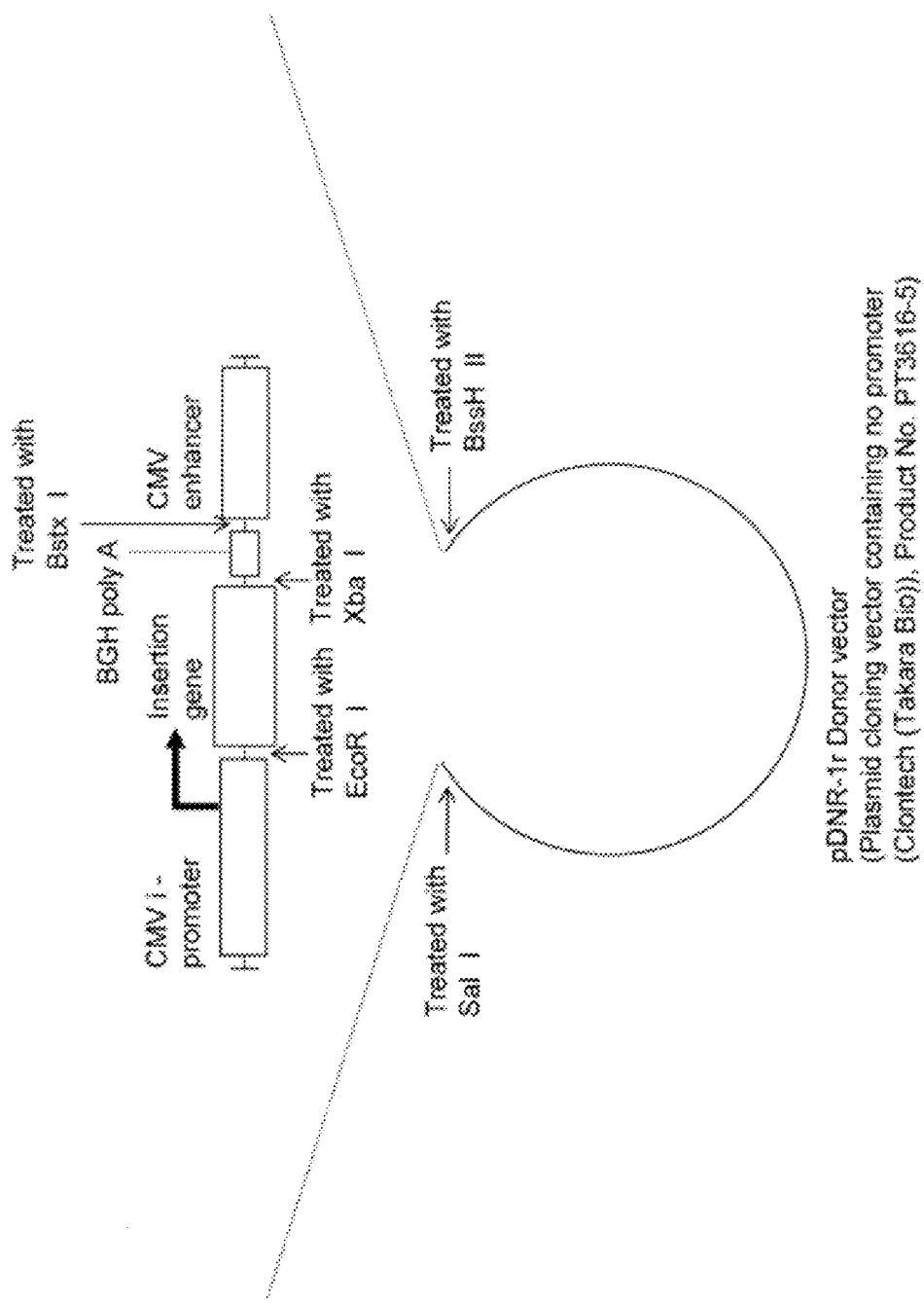
FIG. 8 shows the structure of construct No. 2.

Construct No. 1 is a gene expression plasmid loaded with a CMV i promoter upstream of a gene to be expressed. Furthermore, BGH polyA (bovine growth hormone poly A addition sequence) was ligated downstream of the gene. Specifically, construct No. 1 was thought to have protein expression capacity equivalent to that of a generally employed expression plasmid containing a CMV i promoter.
Construct No. 2 (FIG. 8)

Figure 9:
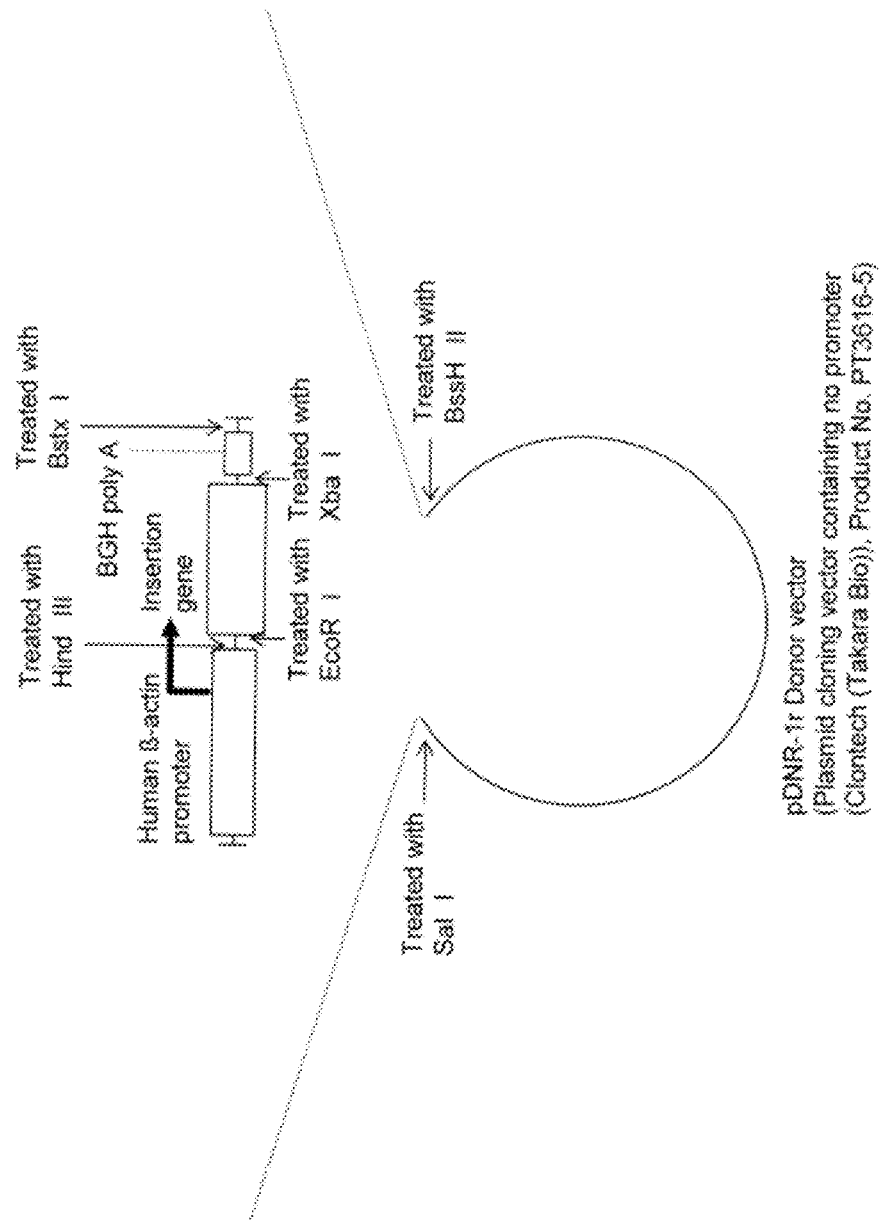
FIG. 9 shows the structure of construct No. 3.

Construct No. 2 was constructed by inserting a CMV enhancer into a site immediately downstream of BGH poly A of construct No. 1.
Construct No. 3 (FIG. 9)

Figure 10:
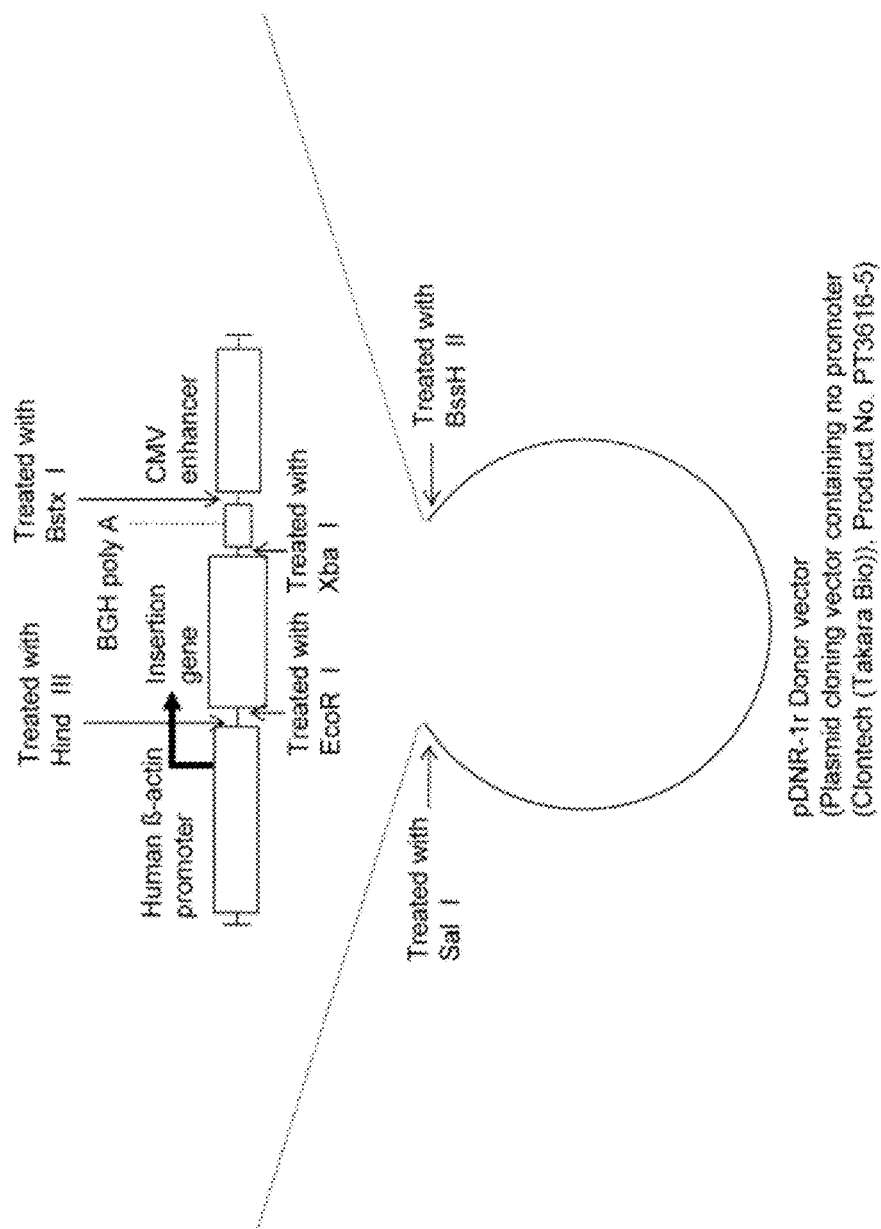
FIG. 10 shows the structure of construct No. 4.

Construct No. 3 was constructed by substituting the CMV i promoter of construct No. 1 with a human β actin promoter.
Construct No. 4 (FIG. 10)

Figure 11:
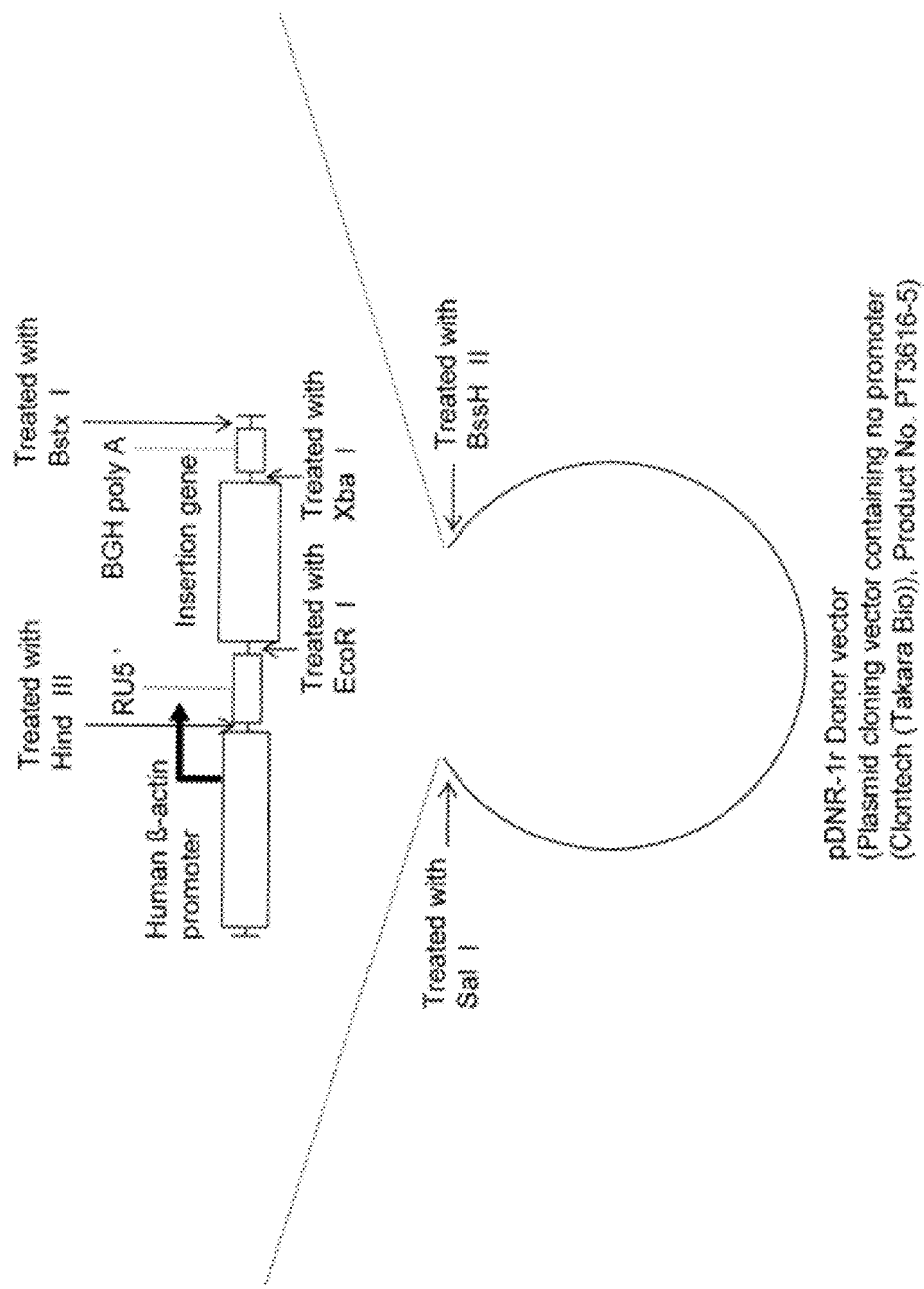
FIG. 11 shows the structure of construct No. 5.

Construct No. 4 was constructed by inserting a CMV enhancer into a site immediately downstream of BGH poly A of construct No. 3.
Construct No. 5 (FIG. 11)

Figure 12:
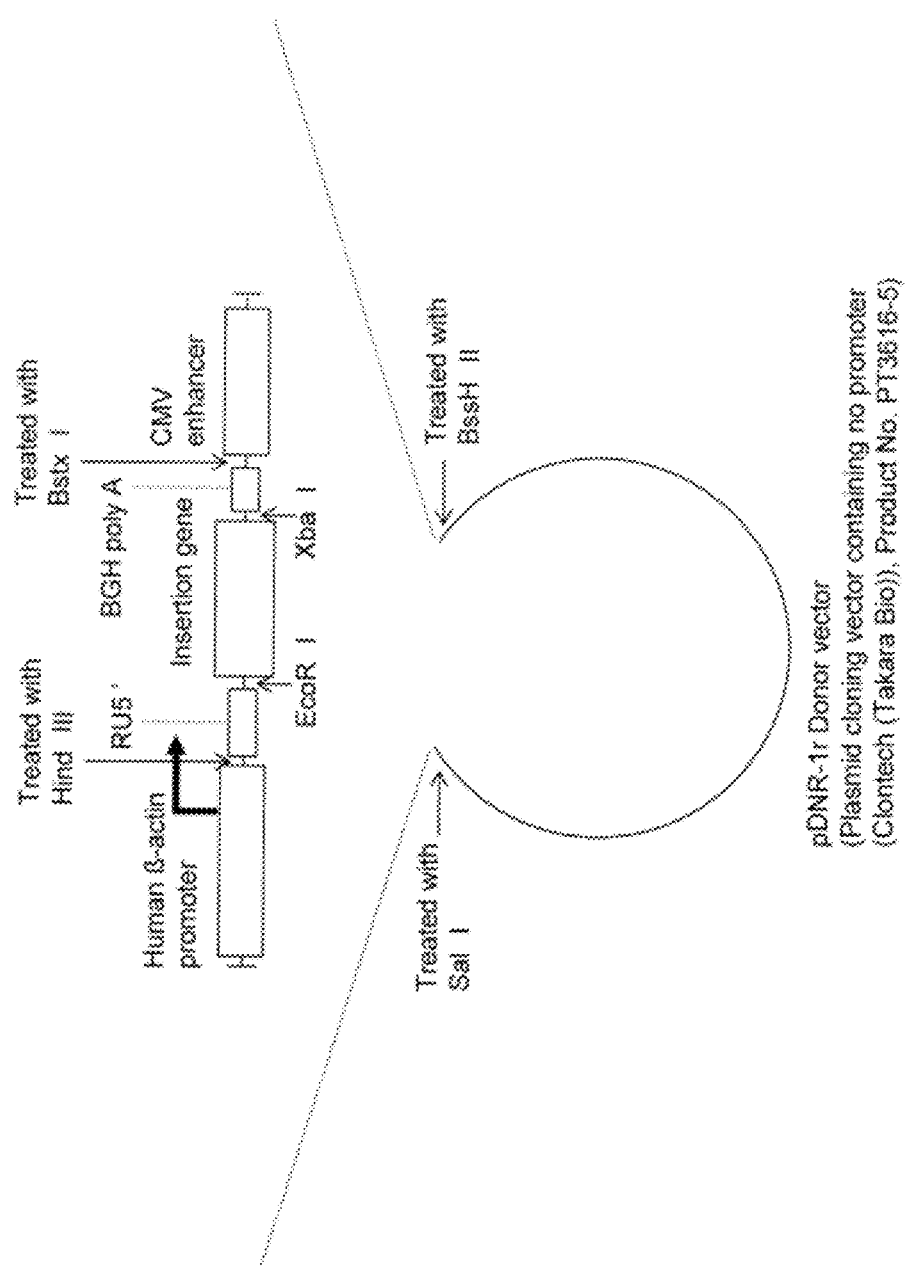
FIG. 12 shows the structure of construct No. 6.

Construct No. 5 was constructed by inserting an RU5' region into a site immediately downstream of the human β actin promoter of construct No. 3.
Construct No. 6 (FIG. 12)

Figure 13:
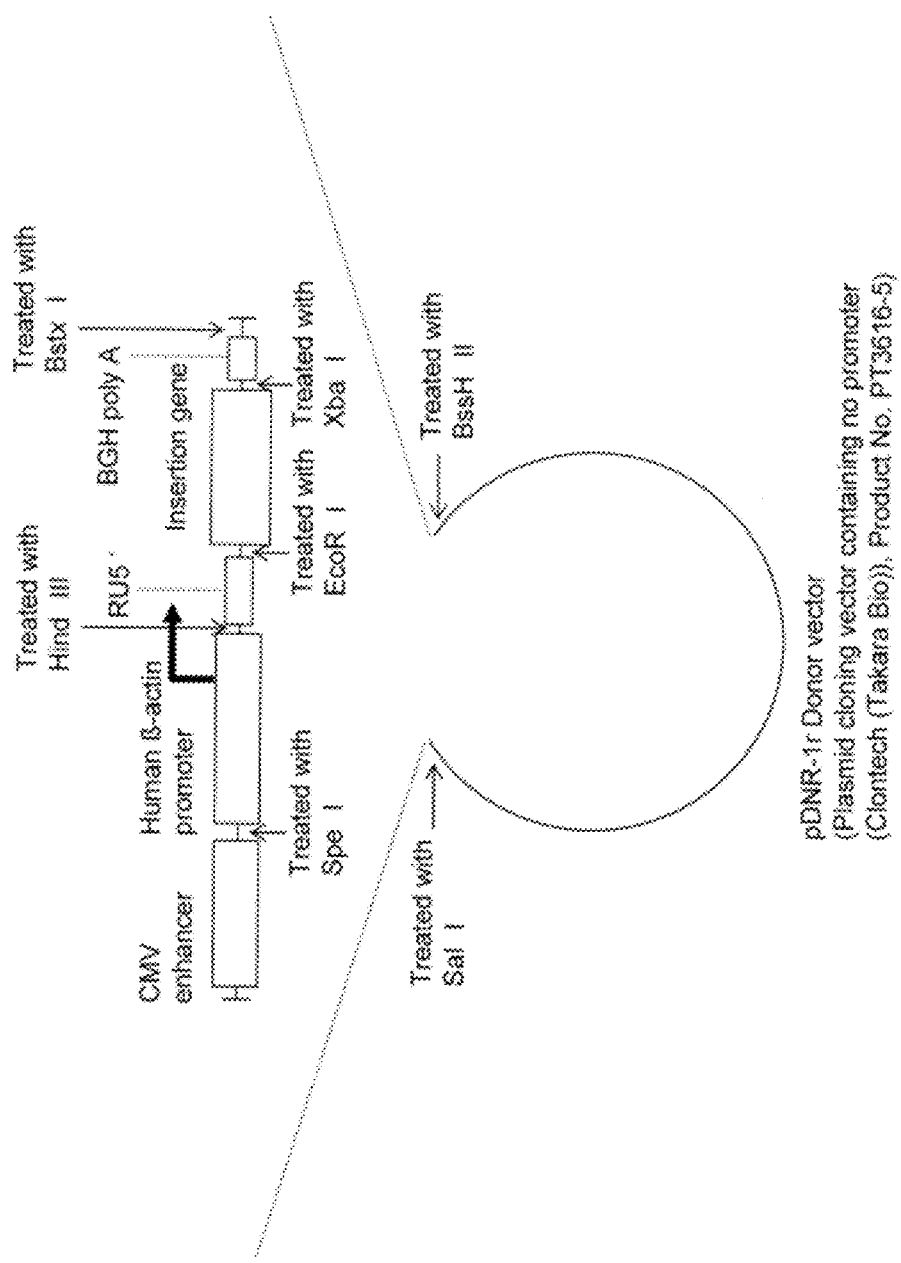
FIG. 13 shows the structure of construct No. 7.

Construct No. 6 was constructed by inserting a CMV enhancer into a site immediately downstream of BGH poly A of construct No. 5.
Construct No. 7 (FIG. 13)

Figure 14:
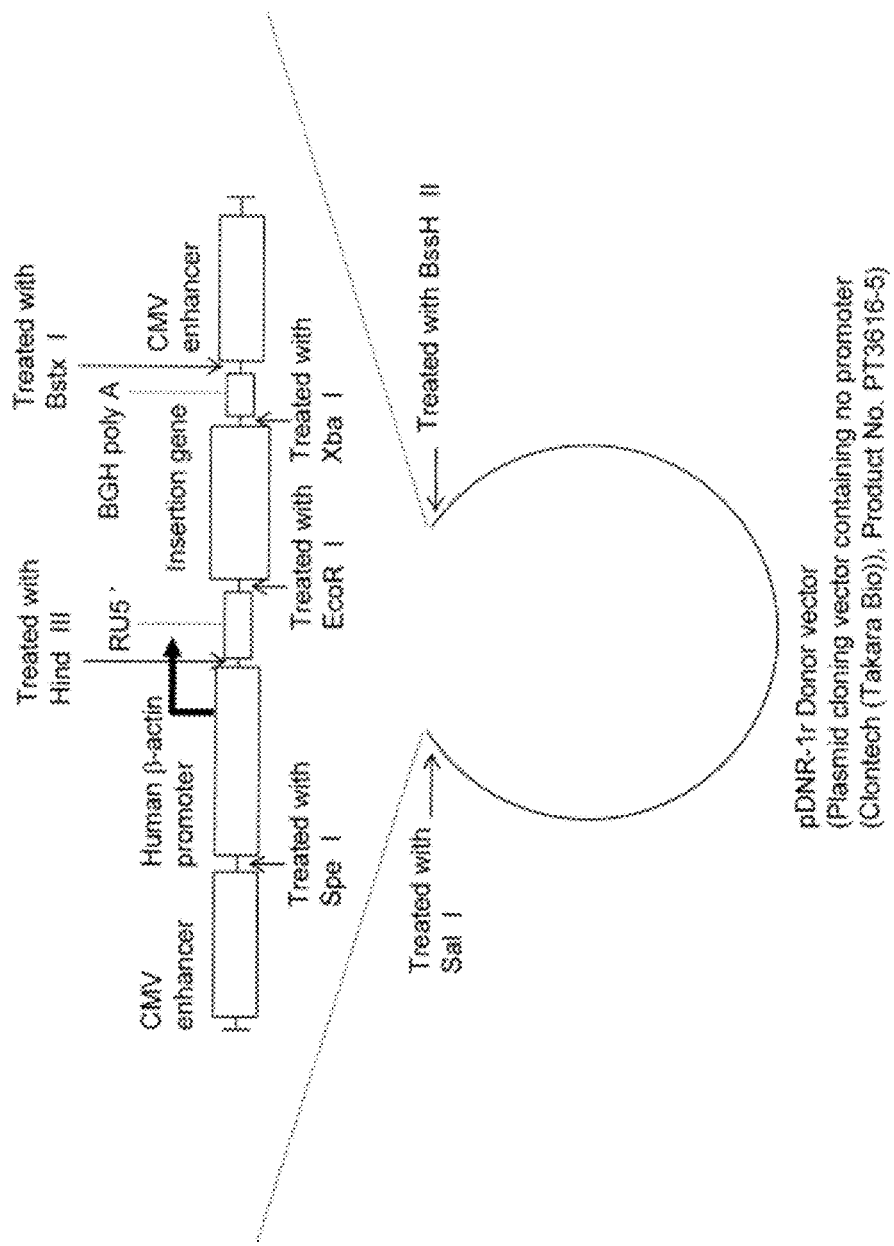
FIG. 14 shows the structure of construct No. 8.

Construct No. 7 was constructed by inserting a CMV enhancer into a site immediately upstream of the human β actin promoter of construct No. 5.
Construct No. 8 (FIG. 14)

Figure 15:
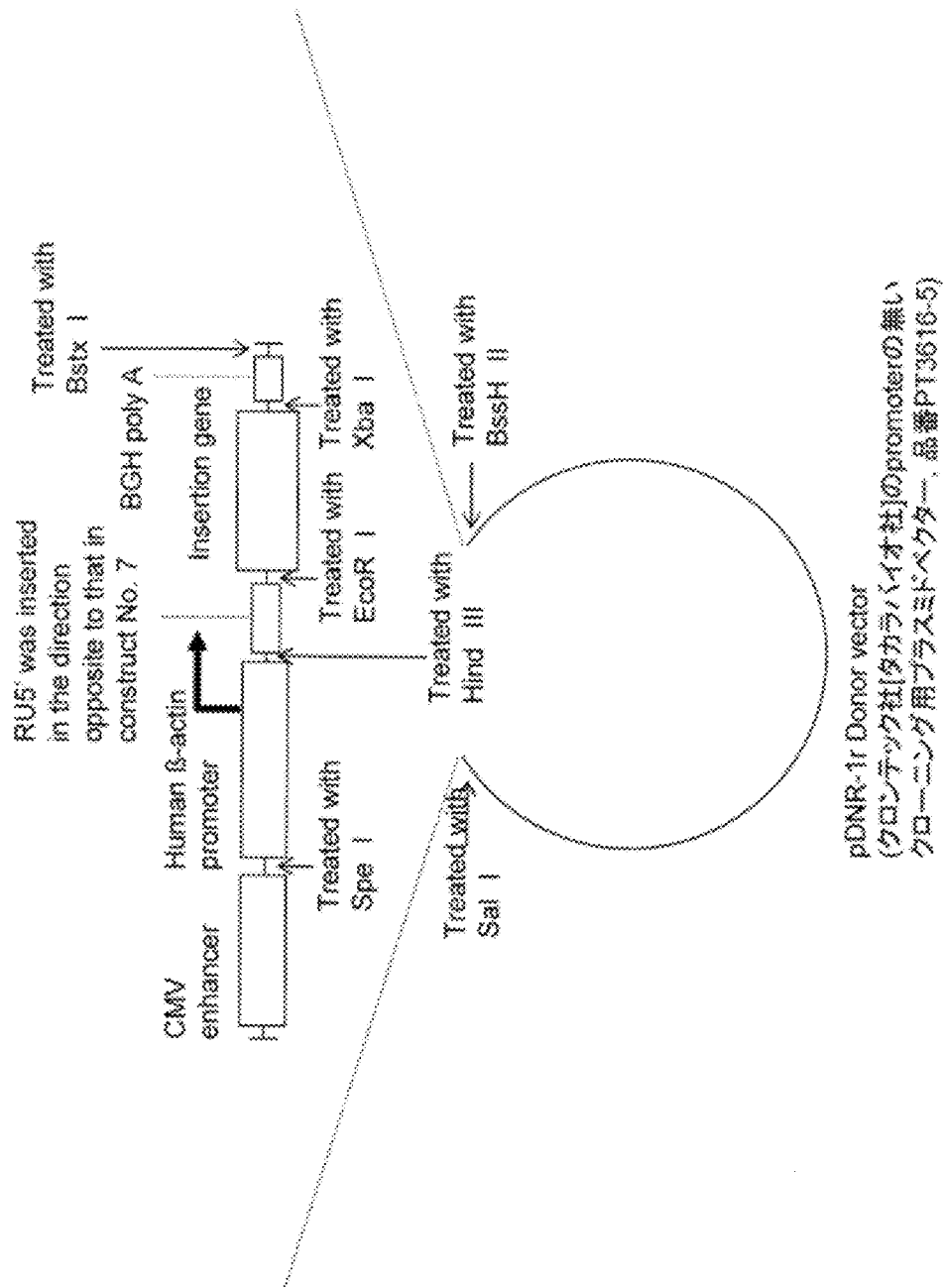
FIG. 15 shows the structure of construct No. 9.

Construct No. 8 was constructed by inserting a CMV enhancer into a site immediately downstream of BGH poly A of construct No. 7.
Construct No. 9 (FIG. 15)

Figure 16:
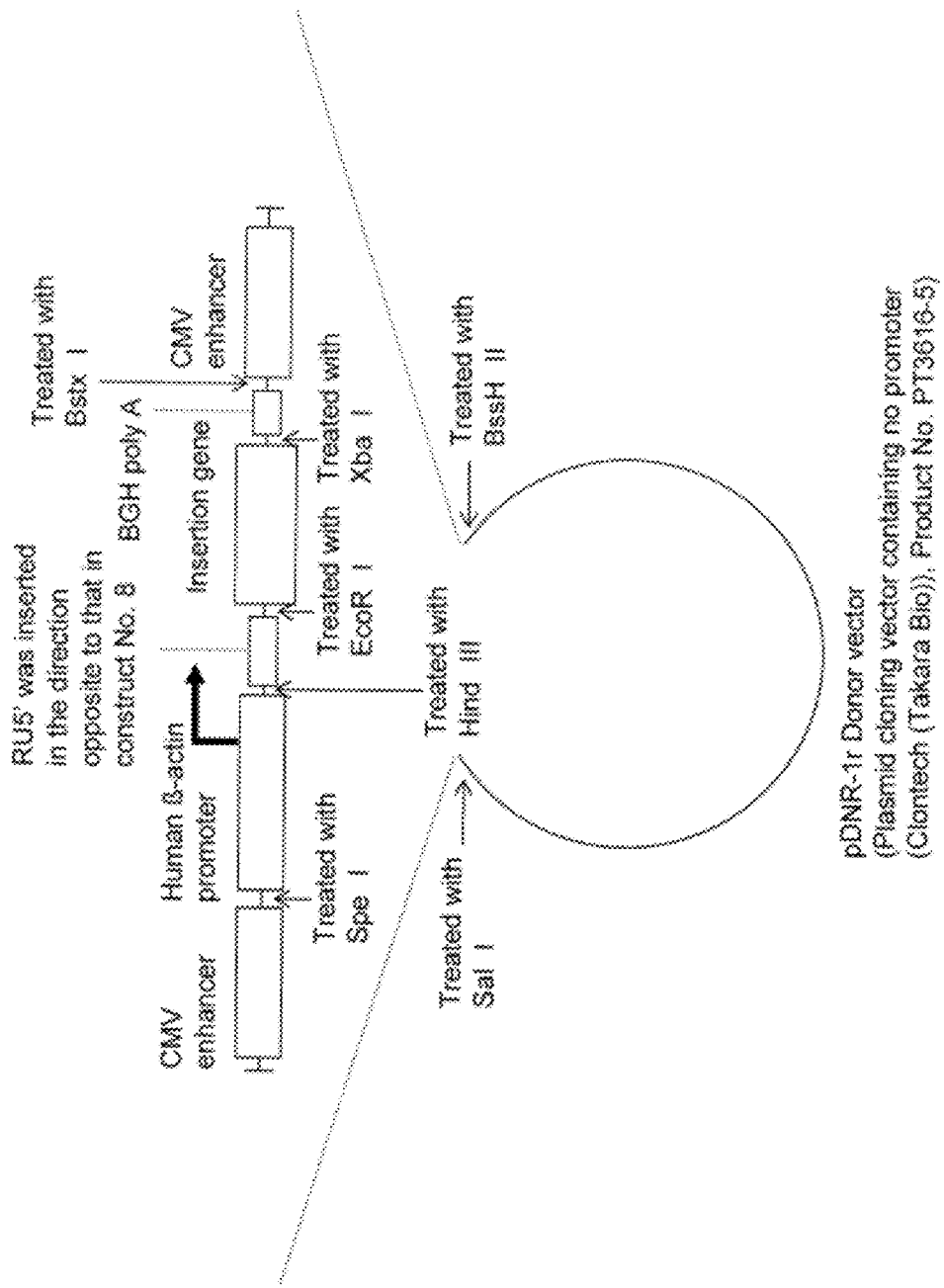
FIG. 16 shows the structure of construct No. 10.

Construct No. 9 was constructed by reversing the direction of the nucleotide sequence of the RU5' region of construct No. 7.
Construct No. 10 (FIG. 16)

Figure 17:
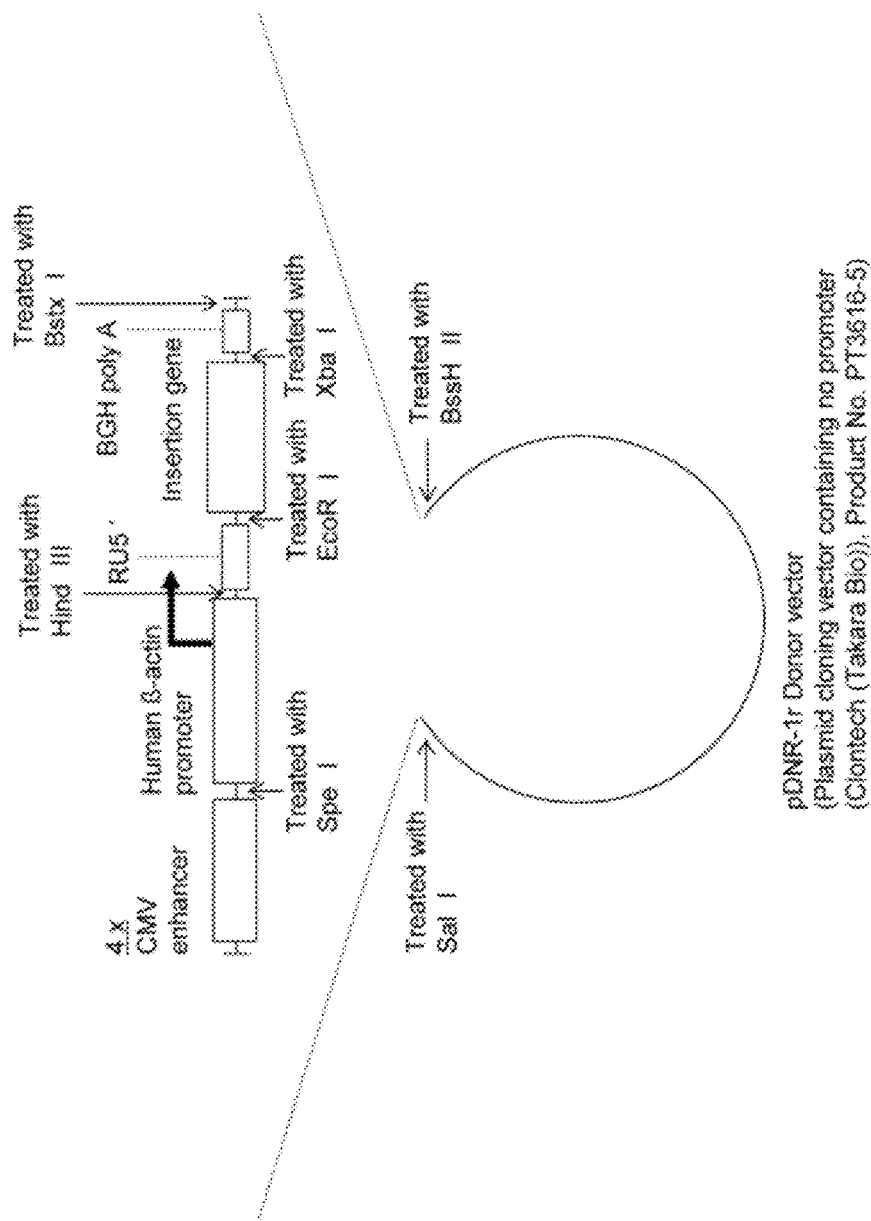
FIG. 17 shows the structure of construct No. 11.

Construct No. 10 was constructed by inserting a CMV enhancer into a site immediately downstream of BGH poly A of construct No. 9.
Construct No. 11 (FIG. 17)

Figure 18:
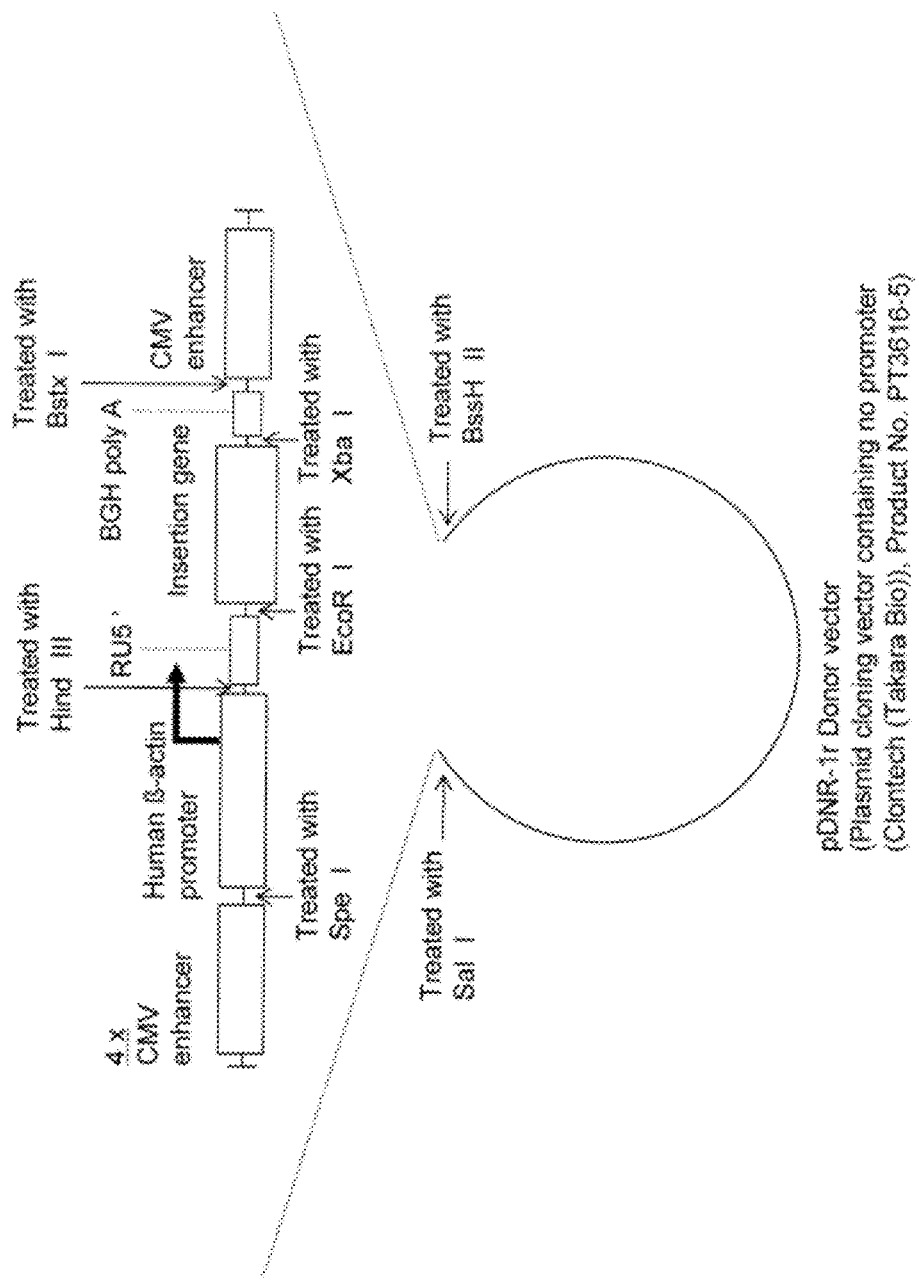
FIG. 18 shows the structure of construct No. 12.

Construct No. 11 was constructed by inserting 4×CMV enhancer (four CMV enhancers) into a site immediately upstream of the human β actin promoter of construct No. 5.
Construct No. 12 (FIG. 18)

Figure 19:
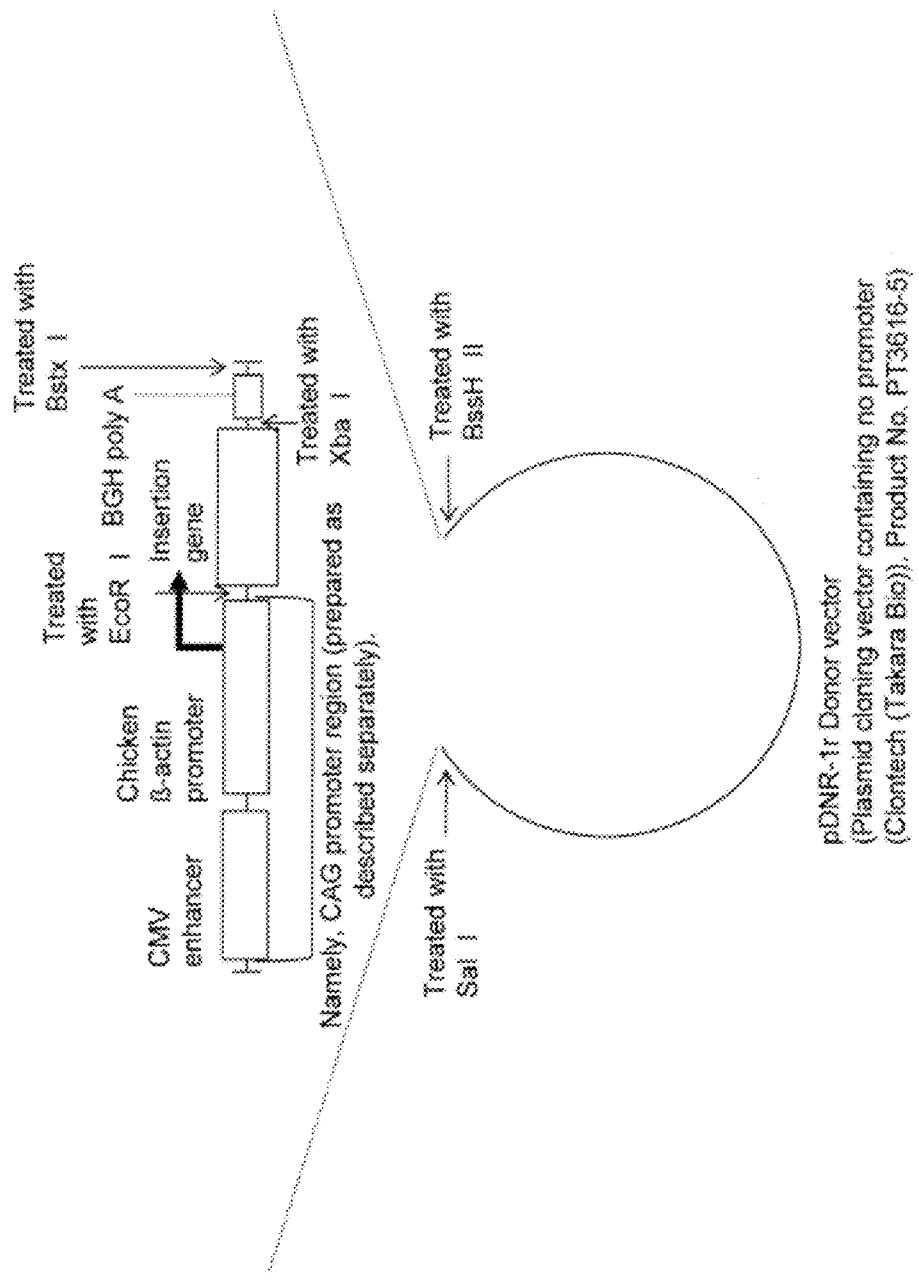
FIG. 19 shows the structure of construct No. 13.

Construct No. 12 was constructed by inserting a CMV enhancer into a site immediately downstream of BGH poly A of construct No. 11.
Construct No. 13 (FIG. 19)

Construct No. 13 is a gene expression plasmid loaded with a CAG promoter. Specifically, construct No. 13 was thought to have protein expression capacity equivalent to that of a generally employed expression plasmid containing a CAG promoter.

Figure 20:
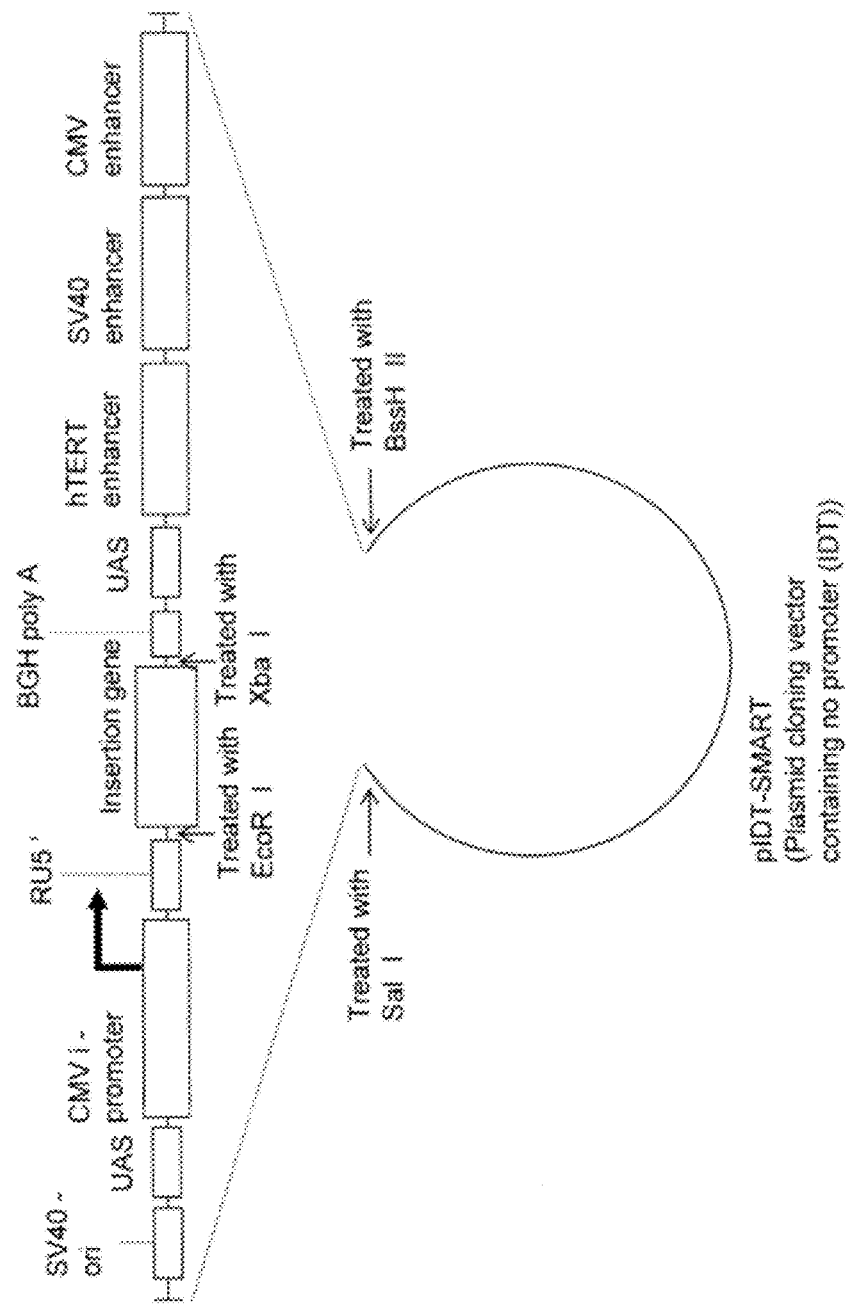
FIG. 20 shows the structure of construct No. 14.

Construct No. 14 (FIG. 20)

The results of examining the above various constructs revealed that gene expression was significantly enhanced via insertion of a CMV enhancer into a site immediately downstream of BGH poly A. Construct No. 14 was constructed by further ligating other enhancers (an hTERT enhancer and a SV40 enhancer). As a result, construct No. 14 was thought to be better than construct No. 2.

Figure 21:
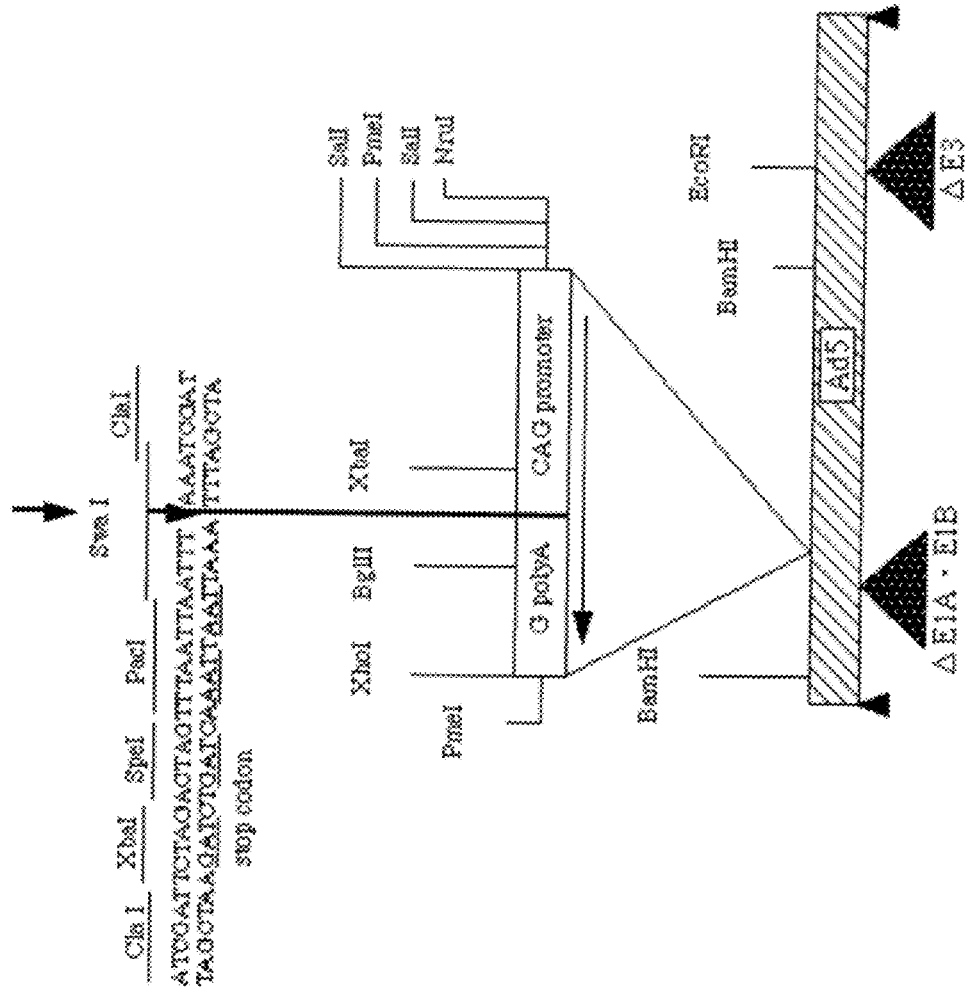
FIG. 21 shows an adenovirus construct encoding a full-length REIC/Dkk-3 gene (the nucleotide sequence flanking the REIC/Dkk-3 gene insertion site is shown, SEQ ID NO.

Adenovirus Construct Encoding Full-Length REIC/Dkk-3 Gene (FIG. 21)

The full-length cDNA of REIC/Dkk-3 (Ad-REIC) was incorporated into a pAxCAwt cosmid vector and then transferred to an adenovirus vector by a COS-TPC method (TAKARA Bio). At this time, an adenovirus vector (Ad-LacZ) retaining a LacZ gene was used as a control vector. Adenovirus vectors used herein were the same as those described in JP Patent No. 3813872.

FIG. 22 to FIG. 35 show the nucleotide sequences of the following elements or constructs.

FIG. 22-1 and FIG. 22-2 (a continuation from FIG. 22-1) show the full nucleotide sequence of a pDNR-1r Donor vector (Plasmid cloning vector having no promoter (Clontech, Product No. PT3616-5)).

FIG. 23 shows the full nucleotide sequence of a pIDT-SMART vector (Plasmid cloning vector having no promoter (IDT)).

FIG. 24 shows the nucleotide sequence of a CMV i promoter (hCMV+intron promoter) region. The region was artificially synthesized based on the known information of the nucleotide sequence of the CMV i promoter region.

FIG. 25 shows the nucleotide sequence of a BGH polyA (3×stop+BGH polyA) region.

The "TAATAAA" portion in the nucleotide sequence is a very important portion in the BGH polyA sequence. This sequence was artificially synthesized based on the known information of the nucleotide sequence of the BGH polyA region.

FIG. 26 shows the nucleotide sequence of a CMV enhancer region. This sequence was artificially synthesized based on the known information of the nucleotide sequence of the CMV enhancer region.

FIG. 27 shows the nucleotide sequence of a human β actin promoter region. This sequence was prepared by obtaining a pDRIVE-h β Actin-RU5' plasmid (InvivoGen) and then amplifying the nucleotide sequence of the relevant portion by PCR.

FIG. 28 shows the nucleotide sequence of a RU5' forward {R segment of HTLV Type 1 long terminal repeat and a portion (R-U5') of U5 sequence} region. This sequence was artificially synthesized based on the known information of the nucleotide sequence of the {R segment of HTLV Type 1 long terminal repeat and a portion (R-U5') of U5 sequence} region.

FIG. 29 shows the nucleotide sequence of a RU5' reverse {R segment of HTLV Type 1 long terminal repeat and a portion (R-U5') of U5 sequence} region. This sequence was artificially synthesized based on the known information of the nucleotide sequence of the {R segment of HTLV Type 1 long terminal repeat and a portion (R-U5') of U5 sequence} region.

FIG. 30 shows the nucleotide sequence of a 4×CMV enhancer region. In the nucleotide sequence shown in FIG. 30, each underlined portion is referred to as namely a "short CMV enhancer." Because of the presence of the four underlined portions, the region is designated as "4×CMV enhancer region." In addition, the term "CMV enhancer" above is meant to include a "short CMV enhancer." The term "CMV enhancer" generally indicates a long CMV enhancer. The sequence was artificially synthesized based on the known information of the nucleotide sequence of a CMV enhancer region.

FIG. 31 shows the nucleotide sequence of a CAG promoter region, which is the nucleotide sequence of a known CAG promoter region. This sequence was prepared by obtaining a pCAGGS plasmid that was a gene expression vector loaded with a CAG promoter provided by Oriental Yeast Co., ltd., and then amplifying by PCR the nucleotide sequence of the relevant portion based on the thus obtained plasmid.

FIG. 32 shows the nucleotide sequence of a 2IRES insert region, which is the nucleotide sequence of an IRES control gene in FIG. 5 and FIG. 6 (described later). The sequence was prepared by linking the two nucleotide sequences of normal human DNA, a BiP-IRES region (the lower-case letters surrounded by frame (1) in the nucleotide sequence in FIG. 32) and a Myc-IRES region (the lower-case letters surrounded by frame (2) in the nucleotide sequence in FIG. 32) in such order. This is a gene to be used as a control gene for an insertion gene. This sequence was artificially synthesized based on the known information of the nucleotide sequences of the BiP-IRES region and the Myc-IRES region.

FIG. 33 shows the nucleotide sequence of a SV40ori-UAS-CMVi-RU5' region, which is the nucleotide sequence of an insertion portion on the left of an insertion gene (foreign gene) in construct No. 14 (best construct). This sequence was artificially synthesized based on the known information of the nucleotide sequence of each region contained in the relevant portion. The portion surrounded by frame (1) in the nucleotide sequence in FIG. 33 indicates the SV40 on region, the portion surrounded by frame (2) in the same indicates the CMV i promoter region, and the portion surrounded by frame (3) in the same indicates the RU5' region.

FIG. 34 shows the nucleotide sequence of a 3×stop-BGH-polyA-UAS-hTERT enhancer+SV40 enhancer+CMV enhancer region, which is the nucleotide sequence of an insertion portion on the right (downstream side) of an insertion gene (foreign gene) in construct No. 14 (best construct). This sequence was artificially synthesized based on the known information of the nucleotide sequence of each region contained in the relevant portion. In the nucleotide sequence in FIG. 34, the uppercase letters surrounded by frame (1) indicate the BGH polyA region, the lowercase letters surrounded by frame (2) indicate the hTERT enhancer region, and the uppercase letters surrounded by frame (3) indicate the SV40 enhancer region, and the lowercase letters surrounded by frame (4) indicate the CMV enhancer region.

FIG. 35-1 and FIG. 35-2 show the full nucleotide sequence of construct No. 14 vector and specifically show the nucleotide sequence of construct No. 14 (best construct) shown in FIG. 20. The full nucleotide sequence also contains a pIDT-SMART vector portion (the region terminates at the bold portion on line 10 of the nucleotide sequence in FIG. 35-1 and the region following GCGCGC surrounded by the frame on line 24 from the bottom in the nucleotide sequence of FIG. 35-2). This sequence was prepared by incorporating the insertion portion on the left and the same on the right of the insertion gene (foreign gene in construct No. 14) shown in former two figures into the above-mentioned pIDT-SMART vector. In FIG. 35-1 and FIG. 35-2, (1) indicates the SV-40 on region, (2) indicates the CMV i promoter region, (3) indicates the RU5' region, (4) indicates the BiP IRES region, (5) indicates the Myc IRES region, (6) indicates the hTERT enhancer region, and (7) indicates the SV40 enhancer region.

(2) Foreign Genes (Insertion Genes)

6His-S100A11-HA

6His-S100A11-HA was prepared by PCR using the cDNA of a normal human fibroblast as a template, a primer with a 6-His linker added to the 5' side, and a primer with an HA linker added to the 3' side.

GFP (Green Fluorescent Protein)

GFP was prepared by PCR using pEGFP-N2 (GFP expression vector (the product of Clontech)) as a template and primers designed on the basis of the template.

REIC/Dkk-3 (Full-Length)

REIC/Dkk-3 was prepared by PCR using the cDNA of a normal human fibroblast as a template and primers designed on the basis of the template.

N78-REIC-6His

N78-REIC-6His was prepared by PCR using primers designed so that 6His was added to the 3' side of the above-obtained full-length REIC/Dkk-3 gene.

Control Gene (IRES)

The term "IRES control gene" used herein refers to a gene prepared by linking the known nucleotide sequences of two normal human DNAs, the BiP-IRES gene and the Myc-IRES gene, in such order. This gene was artificially synthesized. This gene was inserted into the insertion gene (foreign gene) portion of construct No. 14, thereby preparing a control gene for the REIC/Dkk-3 (full-length) gene and N78-REIC-6His-coding DNA in FIG. 5 and FIG. 6 described later.

CD133-6His

CD133-6His was prepared by PCR using the cDNA of a normal human fibroblast as a template and primers designed on the basis of the template.

LGR5-HA

LGR5-HA was prepared by PCR using the cDNA of a normal human fibroblast as a template and primers designed on the basis of the template.

Telomerase-6His

Telomerase-6His was prepared by PCR using the cDNA of a normal human fibroblast as a template and primers designed on the basis of the template.

KLF16

KLF16 was prepared by PCR using the cDNA of a normal human fibroblast as a template and primers designed on the basis of the template.

(3) Transfection and Western Blot Analysis (WB Method)

Various cells (cultured in 6-well plates to 70% to 80% confluency) were transfected with various genes using transfection reagents, FuGENE (trademark)-HD (Roche)), Lipofectamine (trademark) 2000 (Invitrogen), and Trans-IT-Keratinocyte (TAKARA Bio). Procedures therefor were carried out as described in manuals for these products.

Western blot analysis of the thus expressed foreign genes (insertion genes) was conducted by the following methods.

Cells were washed twice using PBS (phosphate buffered saline) and then lysed with lysis buffer (50 mM HEPES, pH 7. 4, 250 mM NaCl, 1 mM EDTA, 1% NP-40, 1 mM DTT, 1 mM PMSF, 5 µg/ml leupeptin, 5 µg/ml aprotinin, 2 mM $Na_3VO_4$, 1 mM NaF, 10 mM (3-GP), so that protein extraction was carried out. After centrifugation, the protein amounts in supernatants to be used for each experiment were adjusted to the same concentration, diluted with the same amount of 2×SDS sample buffer, and then subjected to 5 minutes of heat treatment at 95° C. Each sample (10 µg protein) was separated by 7.5% or gradient SDS-PAGE gel (Bio Rad) and then transferred to a polyvinylidene difluoride (PVDF) membrane. The blot was subjected to 1 hour of blocking at room temperature with TBS (Tris buffered saline) containing 10% fat-free milk powder, 6% glycine, and 0.1% Tween-20. Subsequently, the proteins were identified using the following primary antibodies (1:1000 dilution).

Anti-HA antibody (Cell Signaling Technology)
Anti-GFP antibody (Clontech)
Anti-REIC antibody (rabbit anti-human REIC/Dkk-3 polyclonal antibody)
Anti-6His antibody (MBL)
Anti-KLF16 antibody (Abcam)

The resultants were each sufficiently washed with 0.1% Tween-20-containing TBS (T-TBS), the blot was caused to react with a horseradish peroxidase conjugate secondary antibody. After sufficient washing with T-TBS, detection was carried out by an enhanced chemiluminescence detection method (ECL kit, Amersham Pharmacia Biotech).

Cells were cultured by the following method.

HEK293 (derived from normal human kidney), MCF7 (derived from human breast cancer), PC3 (derived from human prostate cancer), HeLa (derived from human uterine cancer), HepG2 (derived from human hepatic cancer) cell lines were obtained from ATCC (the American Type Culture Collection (Rockville, Md.)). Media used herein are as follows.

HEK293: DMEM high glucose medium (Invitrogen)
MCF7: DMEM high glucose medium (Invitrogen)
PC3: F12 medium (Invitrogen)
HeLa: DMEM high glucose medium (Invitrogen)
HepG2: DMEM high glucose medium (Invitrogen)

The above cell lines were each grown in the above medium supplemented with 10% (v/v) fetal bovine serum, penicillin (100 IU/ml), and streptomycin (100 µg/ml) and then incubated under 5% $CO_2$ conditions.

FIG. 1 to FIG. 6 show the results.

FIG. 1 shows the expression of various foreign genes that were transfected to the HEK293 cell line for 36 hours using FuGENE (trademark)-HD. The protein expression capacity of construct No. 1 was equivalent to that of a generally used (marketed) expression plasmid containing a CMV i promoter. Specifically, it can be said that the protein expression capacity of construct No. 2 was significantly stronger than that of such expression plasmids. Also, similar results were obtained for the following genes. It can be said that construct No. 2 was superior to gene expression systems that are currently broadly employed, in terms of the expression of all types of gene.

S100A11: possible involvement in cancer growth; cytoplasmic-nuclear import protein GFP: fluorescent protein; cytoplasmic protein REIC/Dkk-3 (full length): cancer suppressor protein; secretory protein N78-REIC: protein fragment prepared based on the above gene fragment (peptide fragment consisting of amino acids 1 to 78 of the amino acid sequence of the REIC/Dkk-3 protein shown in SEQ ID NO: 2)

CD133: cancer stem cell marker; expressed also on cell surface

LGR5: stem cell marker for normal cells and cancer cells; transmembrane protein

Telomerase: involvement in aging or anti-aging of cells; cytoplasmic protein

KLF16: involvement in protein transcription; nuclear protein

FIG. 2 shows the expression of a KLF gene after 36 hours of transfection of various cell lines using FuGENE (trademark)-HD. It is said that in all cells (HEK293 cells, MCF7 cells, PC3 cells, HeLa cells, and HepG2 cells) shown in FIG. 2, the protein expression capacity of construct No. 2 (KLF16 gene expression) was significantly stronger than that of construct No. 1. Specifically, it can be said that construct No. 2 is superior to gene expression systems that are currently broadly employed, in terms of gene expression in all types of cell.

Figure 3:
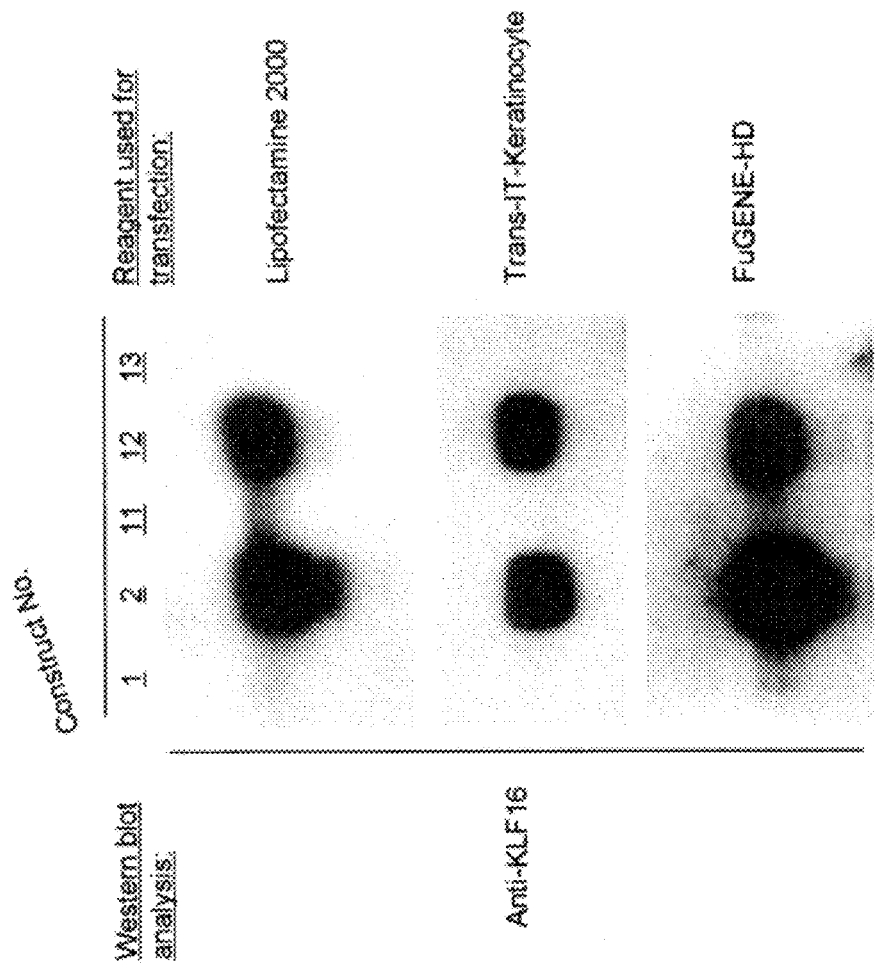
FIG. 3 shows the expression of a KLF gene transfected for 36 hours into a HEK293 cell line using various reagents for transfection.

FIG. 3 shows the expression of a KLF gene transfected to the HEK293 cell line for 36 hours using various transfection reagents. With the use of any transfection reagent, in the case of construct No. 2, the KLF16 protein was expressed at the highest level with the WB method. Construct No. 1 is a construct containing a CMV i promoter that is generally available and often used. Construct No. 13 is a construct similarly containing a CAG promoter that is generally available and often used. Specifically, the use of the construct No. 2 of the present invention realized a protein expression level significantly higher (significantly improved efficiency throughout the gene expression processes) than that obtained with the use of plasmid constructs that are currently in widespread use throughout the world for gene expression.

Figure 4:
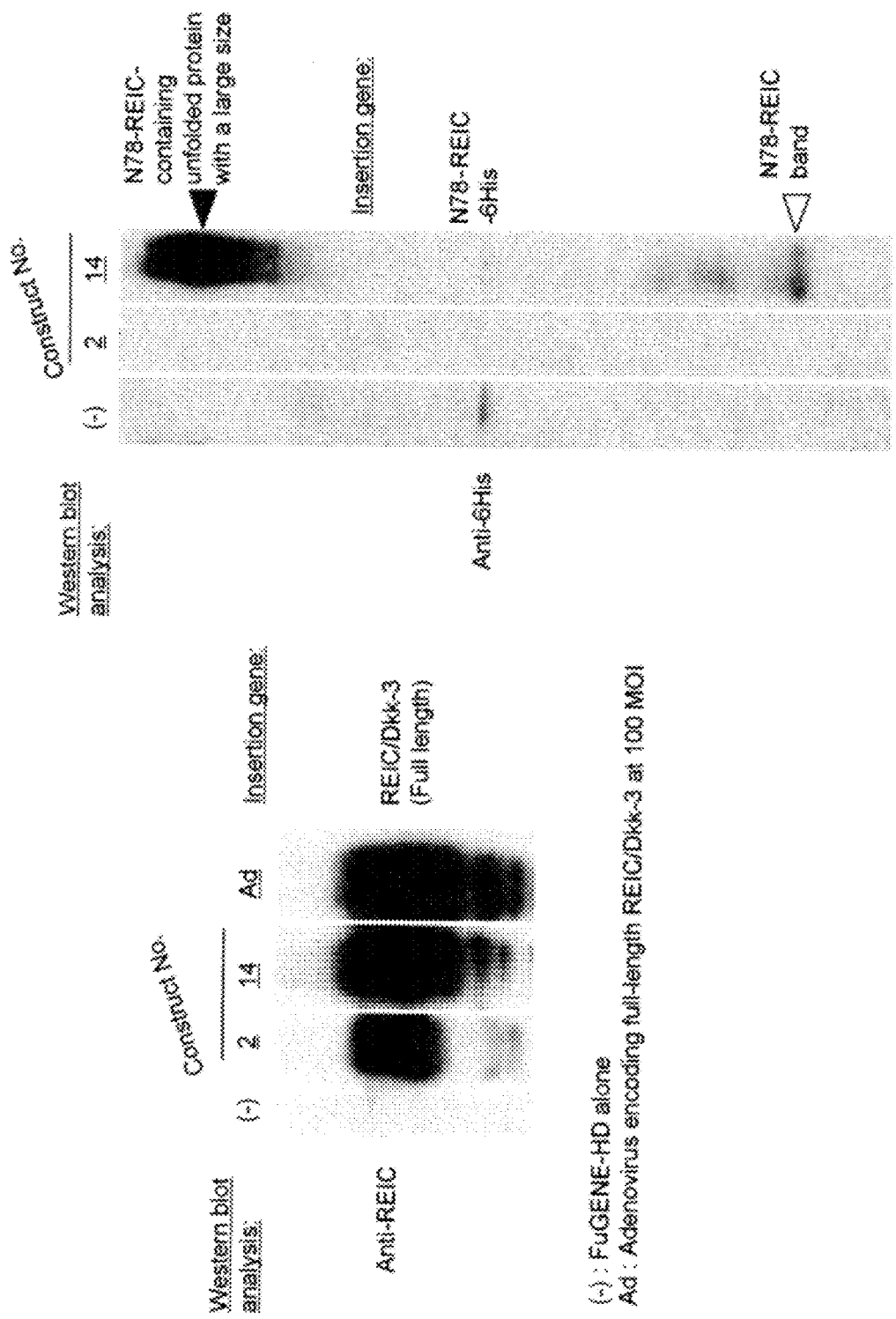
FIG. 4 shows the expression of a full-length REIC gene and an N78-REIC-coding gene transfected for 36 hours into a HEK293 cell line using FuGENE (trademark)-HD.

FIG. 4 shows expression after 36 hours of transfection of the HEK293 cell line with a full-length REIC gene and a N78-REIC-coding gene FuGENE (trademark)-HD. The left panel shows that the REIC/Dkk-3 protein (full-length) was expressed to a significantly higher extent in the case of construct No. 14 than that in the case of construct-No. 2, as revealed by the WB method. Specifically, based on the results for the WB method in FIG. 1 (construct No. 2 exhibited the highest protein expression level among constructs No. 1 to No. 12) and the results for the WB method in FIG. 3 (construct No. 2 exhibited the highest protein expression level among constructs No. 1, No. 2, No. 11, No. 12, and No. 13), among the plasmid constructs examined herein, the useful construct capable of exhibiting the highest protein expression level was construct No. 14. The protein expression capacity of construct No. 14 was strong and equivalent to that possible with the administration of Ad-REIC (full-length REIC/Dkk-3 gene-coding adenovirus) at 100 MOI. The right panel shows that results similar to those in the left panel were obtained when a gene fragment, N78-REIC-6His, was inserted into construct No. 14. Specifically, the useful construct capable of exhibiting the highest protein expression level among the plasmid constructs presented herein was construct No. 14.

Figures 1, 5:
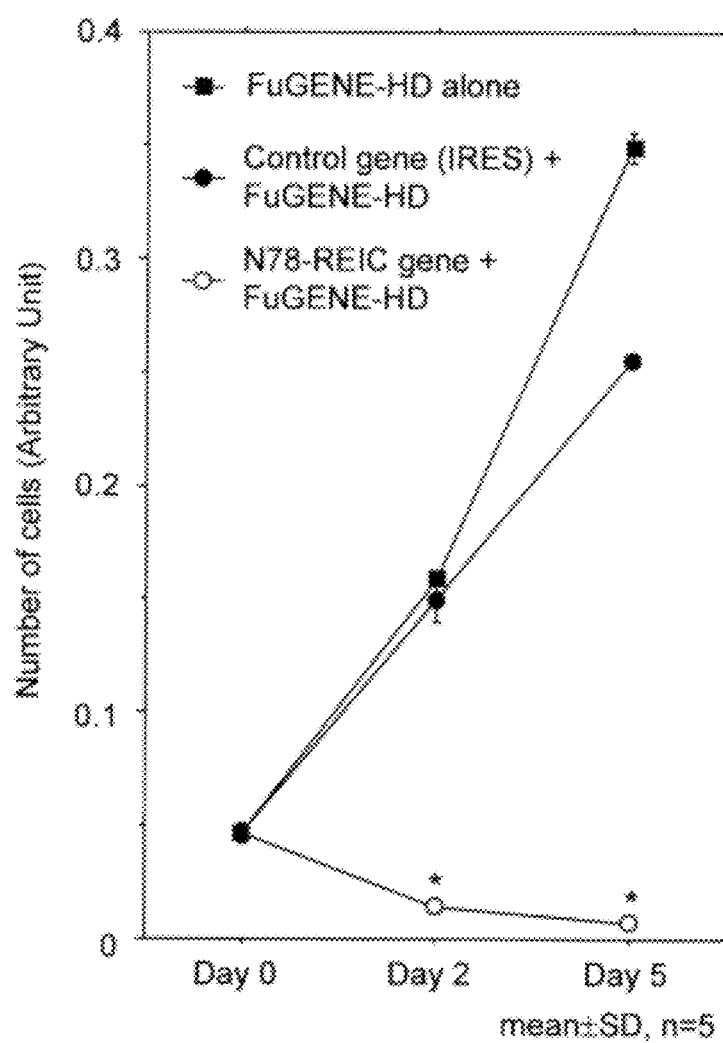

FIG. 5 shows suppressed proliferation of and induction of cell death in a human prostate cancer PC3 cell line by construct No. 14 into which N78-REIC-coding DNA was inserted.

Cell Survival Assay

The PC3 cell line was seeded in complete medium at density of 50,000 cells per well of 6-well plates. After 24 hours of incubation, cells were transfected with a predetermined plasmid in complete medium using a FuGENE (trademark)-HD reagent and then incubated for predetermined days. After incubation, cell survival rate was measured using CellTiter 96 (registered trademark) Aqueous One Solution Cell Proliferation Assay (Promega).

Statistical Analysis

Mann-Whitney U test was conducted between two groups. Significant difference was determined to be present when the result was $p<0.05$.

As shown in FIG. 5, the proliferation of the PC3 cell line was significantly suppressed on days 2 and 5 after administration of construct No. 14 into which N78-REIC-coding DNA had been inserted, compared with a group to which construct No. 14 containing a control gene (IRES) inserted therein had been administered (it can be said that significantly many cell deaths were induced since the number of PC3 cells had decreased because of administration of N78-REIC-coding DNA-construct No. 14).

Figure 6:
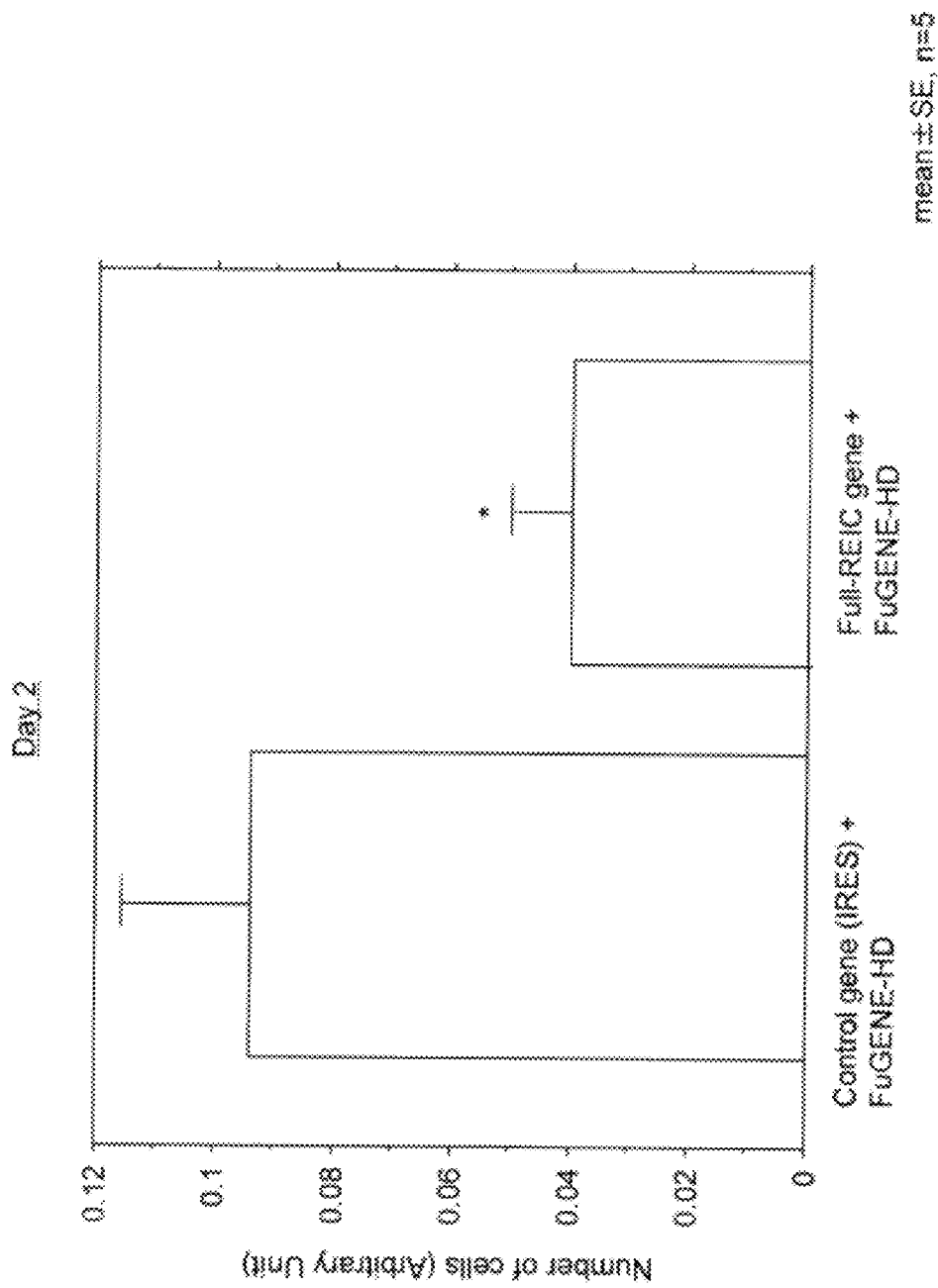
FIG. 6 shows the suppressed proliferation of a human prostate cancer PC3 cell line by construct No. 14 into which a full-length REIC gene was inserted.

FIG. 6 shows suppressed proliferation of the human prostate cancer PC3 cell line by construct No. 14 into which a full-length REIC gene was inserted.

Cell Survival Assay

The PC3 cell line was seeded in complete medium at density of 50,000 per well of 6-well plates. After 24 hours of incubation, cells were transfected with predetermined plasmids in Hank's Balanced Salt Solutions using a FuGENE (trademark)-HD reagent and then incubated for predetermined days. After incubation, cell survival rate was measured using CellTiter 96 (registered trademark) Aqueous One Solution Cell Proliferation Assay (Promega).

Statistical Analysis

Mann-Whitney U test was conducted between two groups. A significant difference was determined to be present when the result was $p<0.05$.

As shown in FIG. 6, on day 2 after administration of construct No. 14 into which the full-length REIC gene had been inserted, the proliferation of PC3 cells was significantly suppressed compared with a group to which construct No. 14 containing a control gene (IRES) inserted therein had been administered.

Example 2

Expression Cassette Containing SV40 Promoter or hTERT Promoter

The expression cassettes of the present invention containing GFP (Green fluorescent protein) as a target gene (insertion gene) were prepared. Hela cells were transfected with the expression cassettes and then GFP expression was observed, so that the expression intensity was analyzed. Transfection was carried out using Lipofectamine 2000. After 48 hours, GFP expression was observed under a fluorescence microscope.

The constructs of the expression cassettes used herein were: construct No. 14 (FIG. 20) used in Example 1; construct No. 15 (FIG. 36) wherein the CMV i promoter of construct No. 14 had been substituted with an SV40 promoter; and construct No. 16 (FIG. 37) wherein the CMV i promoter of construct No. 14 had been substituted with an hTERT promoter. A GFP gene was prepared by PCR using primers designed with the use of a GFP expression vector (a product of Clontech), pEGFP-N2, as a template. The GFP gene was inserted into the target gene insertion part of each construct and then used. A commercial pEGFP-N1 GFP expression plasmid (Clontech) was used as a control.

FIG. 38 shows the nucleotide structure of a partial fragment comprising the SV40 ori+UAS+SV40 enh+intron A+RU5' region of expression vector construct No. 15. The nucleotide sequence thereof is shown in SEQ ID NO: 19. Furthermore, FIG. 39 shows the structure of a partial fragment comprising the SV40 ori+UAS+hTERT enh+intron A+RU5' region of expression vector construct No. 16. The nucleotide sequence thereof is shown in SEQ ID NO: 20. Furthermore, FIG. 40 shows the nucleotide sequence (SEQ ID NO: 21) of GFP-coding DNA to which a restriction enzyme site was ligated. Portions surrounded by frames (1), (2), (3), and (4) shown in the nucleotide sequence in FIG. 38 indicate SV40 ori, SV40 promoter, intron A, and RU5', respectively. Portions surrounded by frames (1), (2), (3), and (4) shown in the nucleotide sequence in FIG. 39 indicate SV40 ori, hTERT promoter, intron A, and RU5', respectively. The full-length nucleotide sequence of expression vector construct No. 14 into which a GFP gene was inserted is shown in FIG. 41-1 and FIG. 41-2 (a continuation from FIG. 41-1) (SEQ ID NO: 22). Also, the full-length nucleotide sequence of expression vector construct No. 15 into which a GFP gene was inserted is shown in FIG. 42-1 and FIG. 42-2 (a continuation from FIG. 41-1) (SEQ ID NO: 23). Furthermore, the full-length nucleotide sequence of expression vector construct No. 16 into which a GFP gene was inserted is shown in FIG. 43-1 and FIG. 43-2 (a continuation from FIG. 43-1) (SEQ ID NO: 24). Portions surrounded by frames (1), (2), (3), and (4) in the nucleotide sequence in FIG. 41-1 and FIG. 41-2 indicate CMV i promoter (P-CMViRU), GFP gene, Myc IRES, and 3 enhancers (pA-3enh), respectively. Portions surrounded by frames (1), (2), (3), and (4) in the nucleotide sequence in FIG. 42 indicate SV40 promoter (P-SViRU), GFP gene, Myc IRES, and 3 enhancers (pA-3enh), respectively. Portions surrounded by frames (1), (2), (3), and (4) in the nucleotide sequence in FIG. 43 indicate hTERT promoter (P-TiRU), GFP gene, Myc IRES, and 3 enhancers (pA-3enh), respectively.

Construct No. 15 is a plasmid vector that is advantageous in strong gene expression in an environment where the SV40 protein is expressed at a high level. Construct No. 16 is a plasmid vector that is advantageous in strong gene expression in an environment where the hTERT protein is expressed at a high level in cancer cells or the like.

Figure 44:
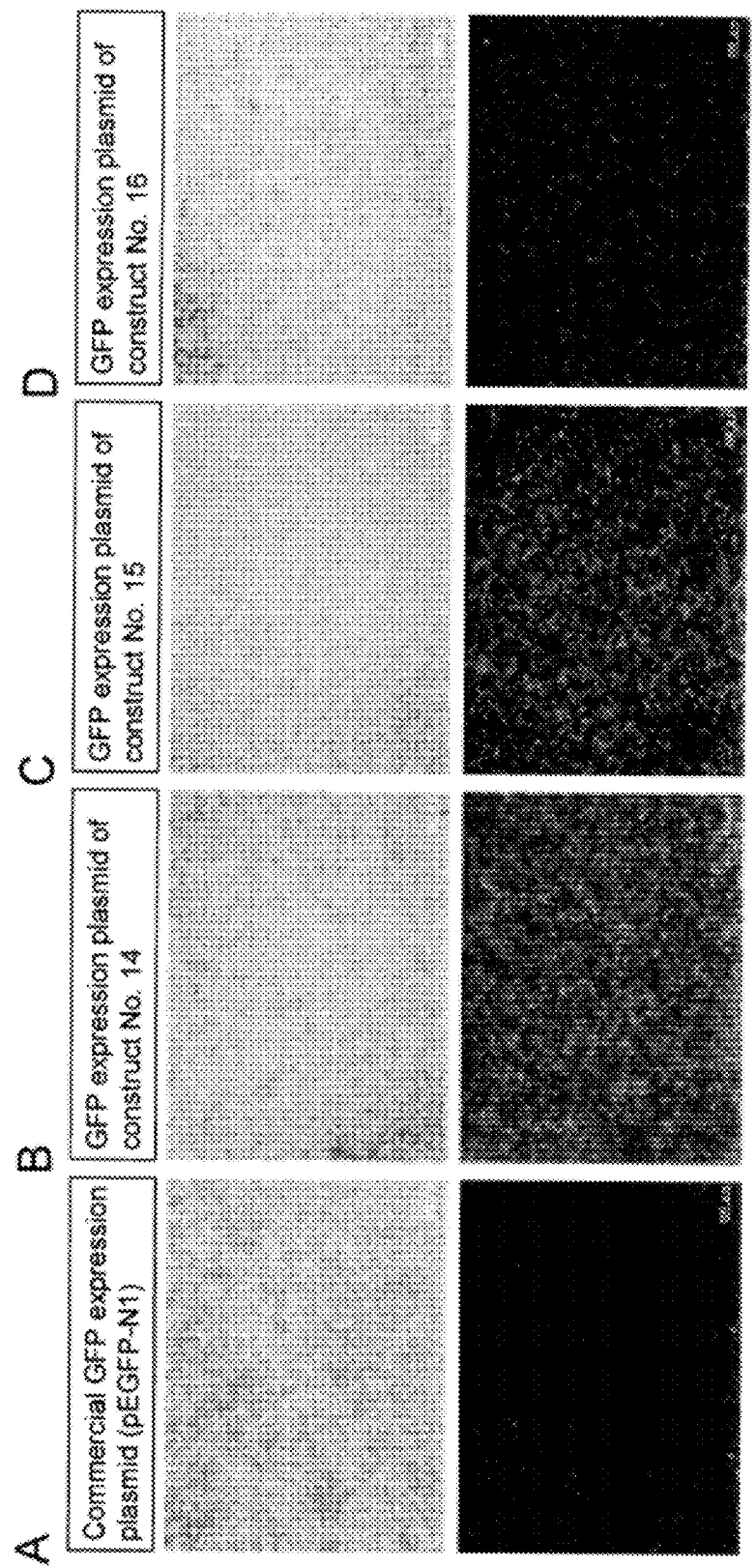
FIG. 44 shows the intensity of GFP gene expression when a plasmid containing an SV40 promoter (construct No. 15) and an hTERT promoter (construct No. 16) was used.

FIG. 44 shows the results. FIGS. 44 A, B, C and D show the results of a commercial GFP expression plasmid (pEGFP-N1), a GFP expression plasmid construct No. 14, GFP expression plasmid construct No. 15, and GFP expression plasmid construct No. 16, respectively. Panels in the upper row in FIG. 44 indicate the bright field. As shown in FIG. 44, the CMV promoter, the SV40 promoter, and the hTERT promoter were all observed to exhibit strong GFP gene expression compared with the commercial plasmid. This example demonstrates that this system (the backbone of construct No. 14) can be used for gene enhancement even when promoters were varied in this manner.

Example 3

Expression of Human Erythropoietin

The expression cassette of the present invention containing human erythropoietin as a foreign gene (insertion gene) was prepared. HEK293 cells were transfected with the expression cassette and then the thus expressed protein was analyzed by Western blot. Transfection was carried out using FuGENE (trademark)-HD. After 24 hours, human erythropoietin in a cell culture solution was detected by Western blotting.

The construct of the expression cassette used herein was construct No. 14 (FIG. 20) used in Example 1, to which DNA encoding human erythropoietin was inserted as a target gene (insertion gene). FIG. 45 shows the nucleotide sequence (SEQ ID NO: 25) of DNA encoding human erythropoietin to which a restriction enzyme site had been ligated. As controls, with the use of commercial pTracer (registered trademark)-EF/V5-His-A (Invitrogen) and pEF6/Myc-His-A expression plasmids (Invitrogen), human erythropoietin-coding DNA was inserted into the EcoR 1-Xba 1 restriction enzyme site of each plasmid.

Western blotting was carried out using an anti-6His antibody (MBL). At 24 hours after transfection, 1 mL of a culture solution was subjected to trapping with 6His amino acid residues. The total amount of the thus collected protein was used for Western blotting.

Figure 46:
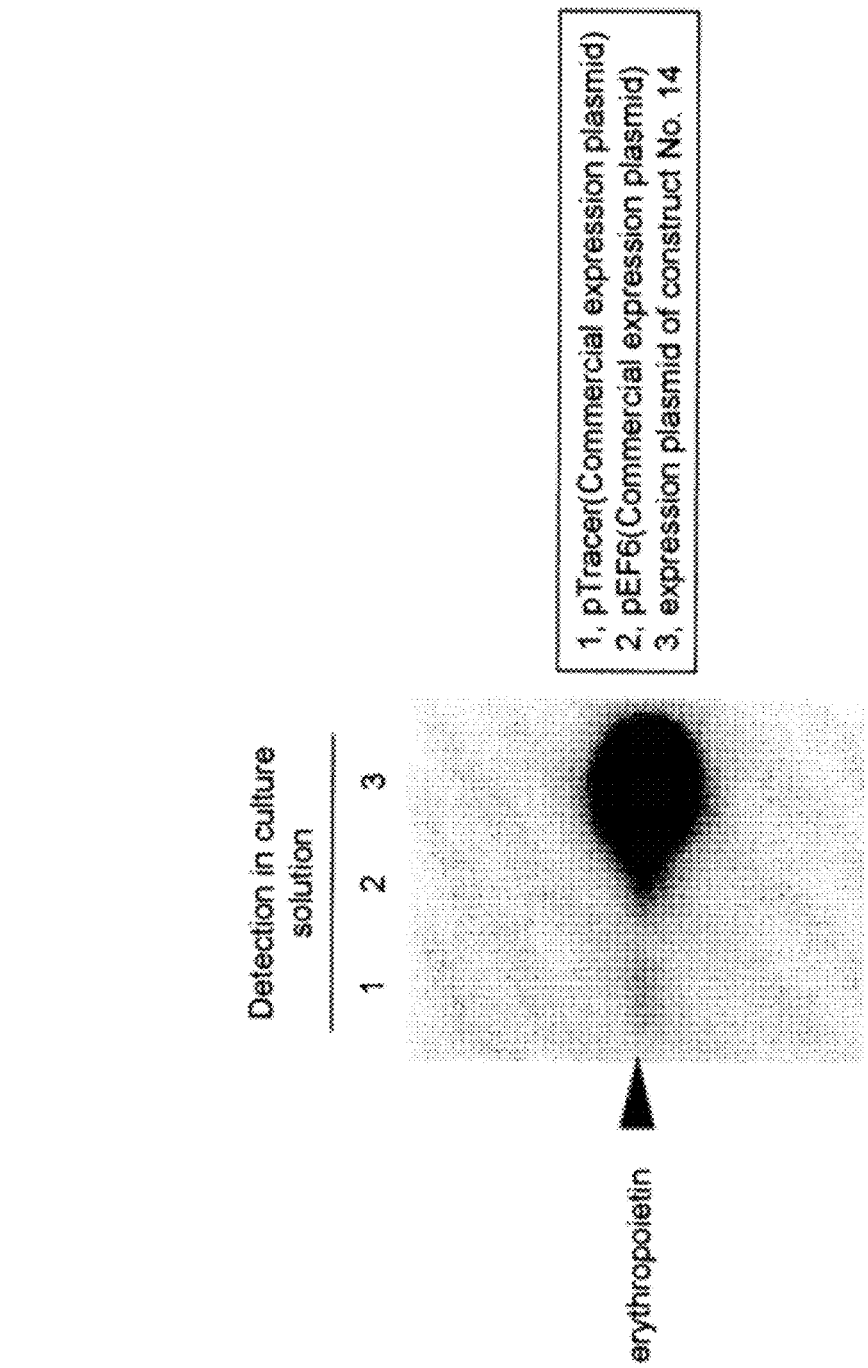
FIG. 46 shows the result of the expression of human erythropoietin using plasmid construct No. 14.

FIG. 46 shows the results. Lane 1 shows the results of expression using pTracer (registered trademark)-EF/V5-His-A, lane 2 shows the results of expression using pEF6/Myc-His-A, and lane 3 shows the results of expression using expression plasmid construct No. 14. As shown in FIG. 46, the strongest expression was observed with the use of expression plasmid construct No. 14. This result demonstrates that this system (the backbone of construct No. 14) is useful for production of proteins to be used as pharmaceutical products such as erythropoietin, diagnostic agents, or reagents, in view of mass production based on gene enhancement.

Example 4

Expression of Human IgG

The expression cassette of the present invention containing a human IgG light chain and a human IgG heavy chain as target genes (insertion genes) was prepared. HEK293 cells were transfected with the expression cassette, and then the thus expressed protein was analyzed by Western blot. Transfection was carried out using FuGENE (trademark)-HD. After 24 hours, the human IgG light chain and the human IgG heavy chain in a cell extract and a cell culture solution were detected by Western blotting.

The construct of the expression cassette used herein was construct No. 14 (FIG. 20) used in Example 1, to which a human IgG light chain- or a human IgG heavy chain-coding DNA was inserted as a target gene (insertion gene). FIG. 47 shows the nucleotide sequence (SEQ ID NO: 26 or SEQ ID NO: 27) of DNA encoding a human IgG light chain (FIG. 47A) or a human IgG heavy chain (FIG. 47B), to which a restriction enzyme site was ligated. As a control, with the use of commercial pTracer (registered trademark)-EF/V5-His-A (Invitrogen) and pEF6/Myc-His-A (Invitrogen) expression plasmids, the human IgG light chain- or the human IgG heavy chain-coding DNA was inserted into the EcoR 1-Xba 1 restriction enzyme site of each plasmid.

Western blotting was carried out using an anti-6His antibody (MBL). At 24 hours after transfection, a cell extract (total protein amount: 10 μg) and 1 mL of a culture solution were subjected to trapping with 6His amino acids. The total amount of the thus collected protein was used.

Figure 48:
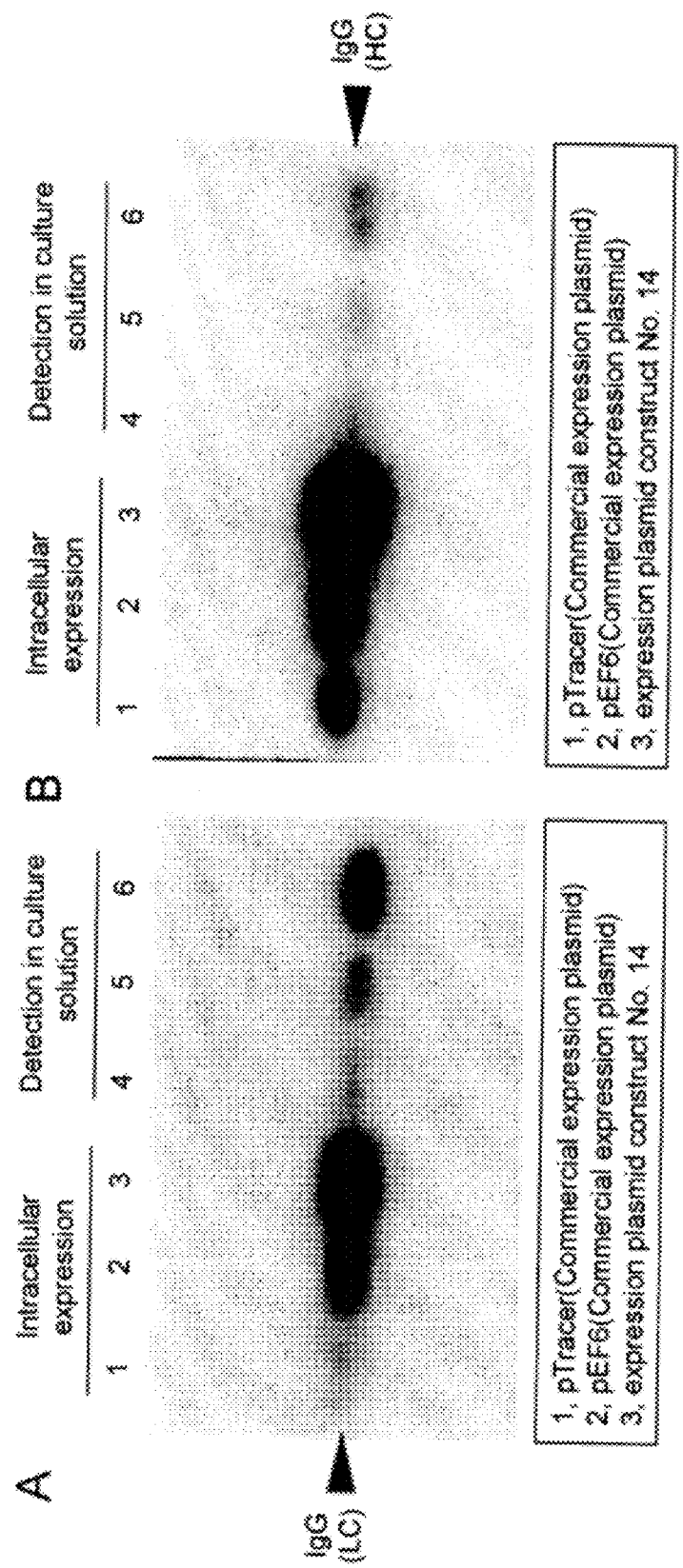
FIG. 48 shows the result of the expression of a human IgG light chain (FIG. 48A) and a human IgG heavy chain (FIG. 48B) using plasmid construct No. 14.

FIG. 48 shows the results. FIG. 48A shows the result for the human IgG light chain and FIG. 48B shows the result for the human IgG heavy chain. In both FIG. 48A and FIG. 48B, lane 1 indicates the result of expression using pTracer (registered trademark)-EF/V5-His-A, lane 2 shows the result of expression using pEF6/Myc-His-A, and lane 3 shows the result of expression using construct No. 14. Also, FIG. 48 shows the results of intracellular expression using the cell extract and the results thereof using the culture solution. As shown in FIG. 48, the strongest expression was observed in the case of using construct No. 14. The results demonstrate that this system (the backbone of construct No. 14) is useful for production of proteins to be used for pharmaceutical products such as antibodies, diagnostic agents, or reagents in view of mass production based on gene enhancement.

Example 5

Expression of REIC Protein Using Expression Vector Constructed by Modification of Commercial Plasmid Vector The expression cassette of the present invention containing a human REIC gene as a foreign gene (insertion gene) was prepared. HEK293 cells were transfected with the expression cassette and then the thus expressed protein was analyzed by Western blot. Transfection was carried out using FuGENE (trademark) HD. After 24 hours, the REIC protein in a cell extract was detected by Western blotting.

Figure 49:
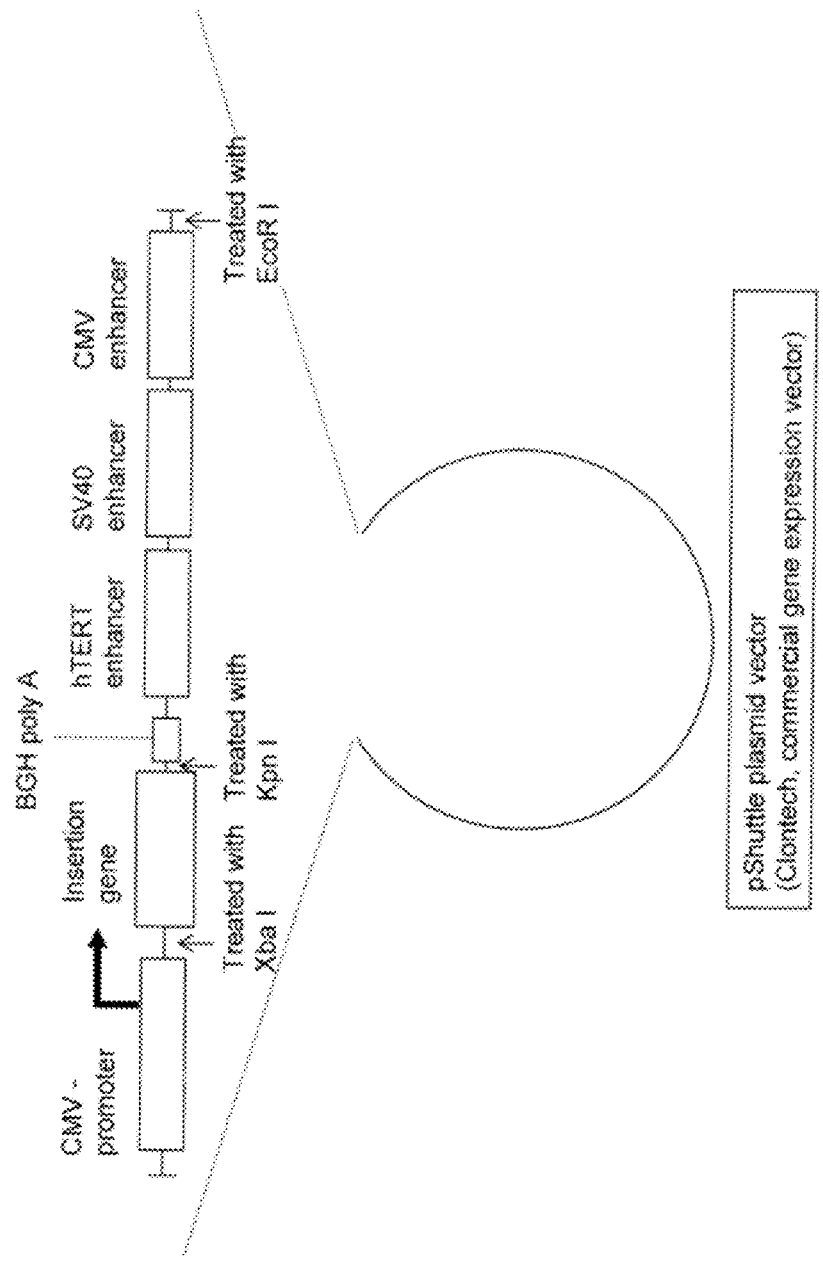
FIG. 49 shows the structure of construct No. 17.

The construct of the expression cassette used herein was construct No. 17 (FIG. 49). Construct No. 17 was constructed by inserting REIC-coding DNA into the Xba 1-Kpn 1 insertion site of a commercial pShuttle plasmid vector (Clontech), and then inserting 3 enhancers (an hTERT enhancer, an SV40 enhancer, and a CMV enhancer) located downstream of an expression gene of expression plasmid construct No. 14 (FIG. 20) used in Example 1 into the Kpn 1-EcoR 1 insertion site downstream of the REIC-coding DNA in the form of BGH poly A+3 enhancers. As a control, a vector constructed by inserting REIC-coding DNA into the Xba 1-Kpn 1 insertion site of a commercial pShuttle plasmid vector (Clontech) was used. FIG. 50 shows the full nucleotide sequence (SEQ ID NO: 28) of expression vector construct No. 17 into which REIC-coding DNA was inserted. Portions surrounded by frames (1) and (2) in the nucleotide sequence in FIG. 50 indicate REIC-coding DNA and 3 enhancers (3xenh), respectively.

Western blotting was carried out using an anti-REIC antibody and a cell extract (total protein amount: 10 µg) obtained at 24 hours after transfection.

Figure 51:
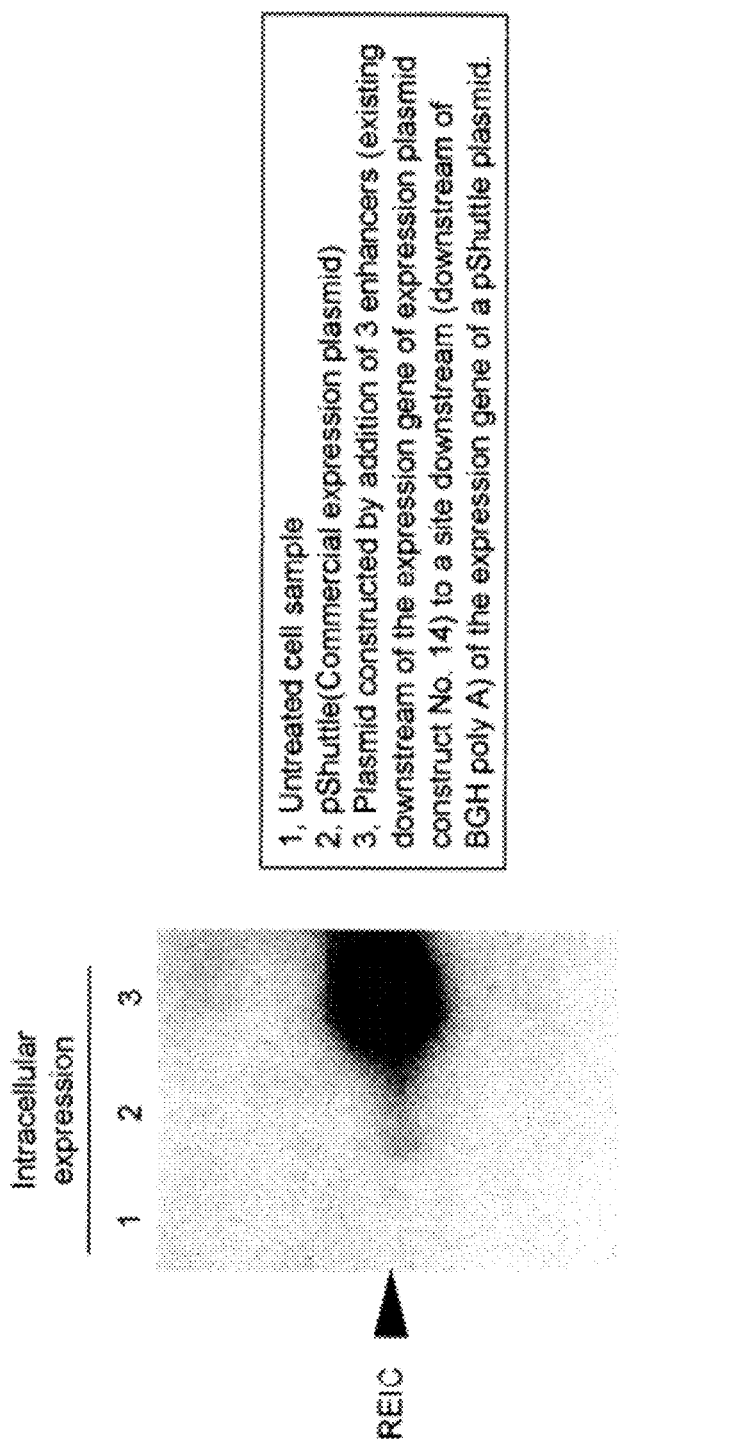
FIG. 51 shows the result of the expression of full-length human REIC using plasmid construct No. 17.

FIG. 51 shows the results. Lane 1 shows the result of a cell extract of cells not caused to express any foreign protein, lane 2 shows the result of a cell extract of cells transfected with a commercial p Shuttle vector to which REIC-coding DNA had been inserted, lane 3 shows the result of a cell extract of cells transfected with an expression vector that had been constructed by inserting REIC-coding DNA into a commercial pShuttle vector, and then inserting 3 enhancers into a site downstream of the REIC-coding DNA (downstream of BGH poly A). As shown in FIG. 51, the strongest expression was observed in the case of using construct No. 17. The results demonstrate that incorporation of the portion of 3 enhancers of this system (the backbone of construct No. 14) into a site downstream of the expression gene cassette of a commercial plasmid such as a pShuttle vector enables to enhance the gene expression. Specifically, the results demonstrate that target gene expression can be enhanced by insertion of the region of 3 enhancers into various gene constructs.

Example 6

Expression of c-myc Gene with the Use of Expression Vector Constructed by Modification of Commercial Plasmid Vector The expression cassette of the present invention containing a human c-mycC gene as a target gene (insertion gene) was prepared. HEK293 cells were transfected with the expression cassette. The thus expressed protein was analyzed by Western blot. Transfection was carried out using FuGENE (trademark)-HD. After 24 hours, the REIC protein in a cell extract was detected by Western blotting.

The construct of the expression cassette used herein was constructed by inserting REIC-coding DNA into the Xba 1-Kpn 1 insertion site of a commercial pShuttle plasmid vector (Clontech), and then inserting 3 enhancers (hTERT enhancer, SV40 enhancer, and CMV enhancer) located downstream of the expression gene of expression plasmid construct No. 14 (FIG. 20) used in Example 1 into the Kpn 1-EcoR 1 insertion site downstream of the REIC-coding DNA in the form of BGH poly A+3 enhancers. As a control, a vector constructed by inserting human c-myc-coding DNA into the Xba 1-Kpn 1 insertion site of a commercial pShuttle plasmid vector (Clontech) was used. FIG. 52 shows the nucleotide sequence (SEQ ID NO: 29) of the inserted c-myc gene. FIG. 53 shows the nucleotide sequence (SEQ ID NO: 30) of a region containing BGH poly A and 3 enhancers contained in construct No. 14.

Western blotting was carried out using an anti-c-mycC antibody (Santa Cruz Biotechnology, Inc., Cat No.: sc-70469) and a cell extract (total protein amount: 10 µg) obtained at 24 hours after transfection.

Figure 54:
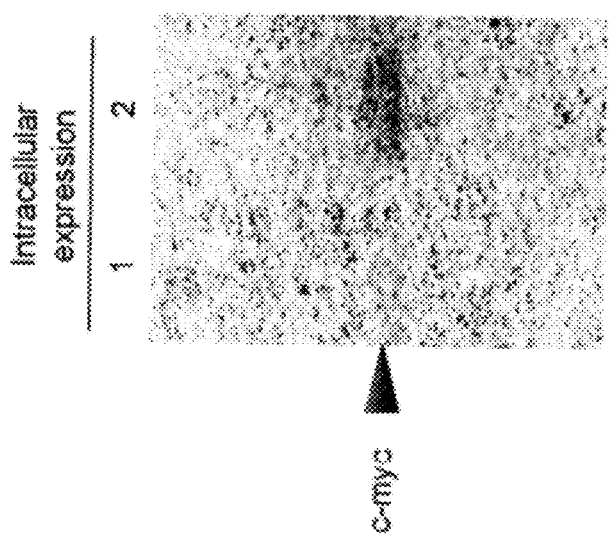
FIG. 54 shows the result of the expression of a c-myc gene after incorporation of the nucleotide sequence (prepared by linking BGH polyA existing downstream of an expression gene of expression plasmid construct No. 14 and 3 enhancers) into a commercial plasmid.
Figure 55:
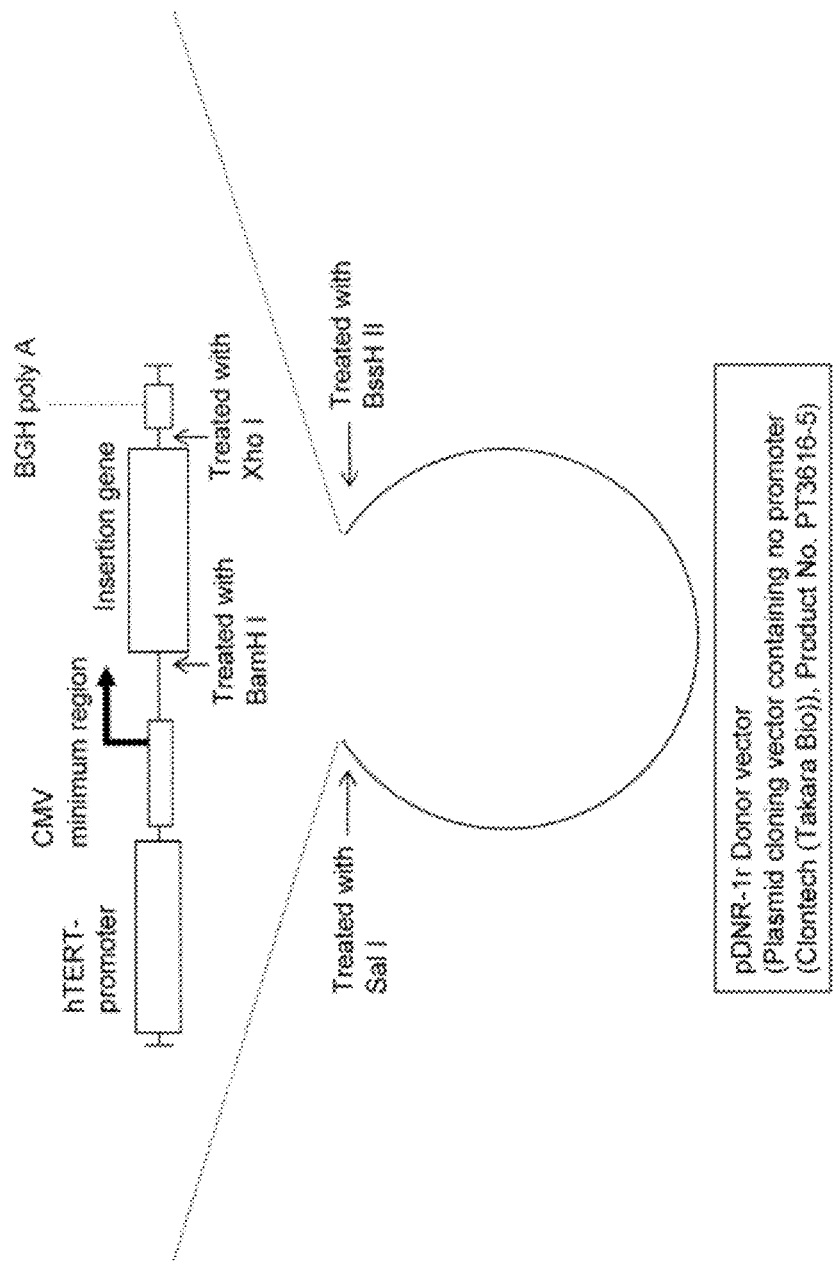
FIG. 55 shows the structure of construct No. 18.
Figure 56:
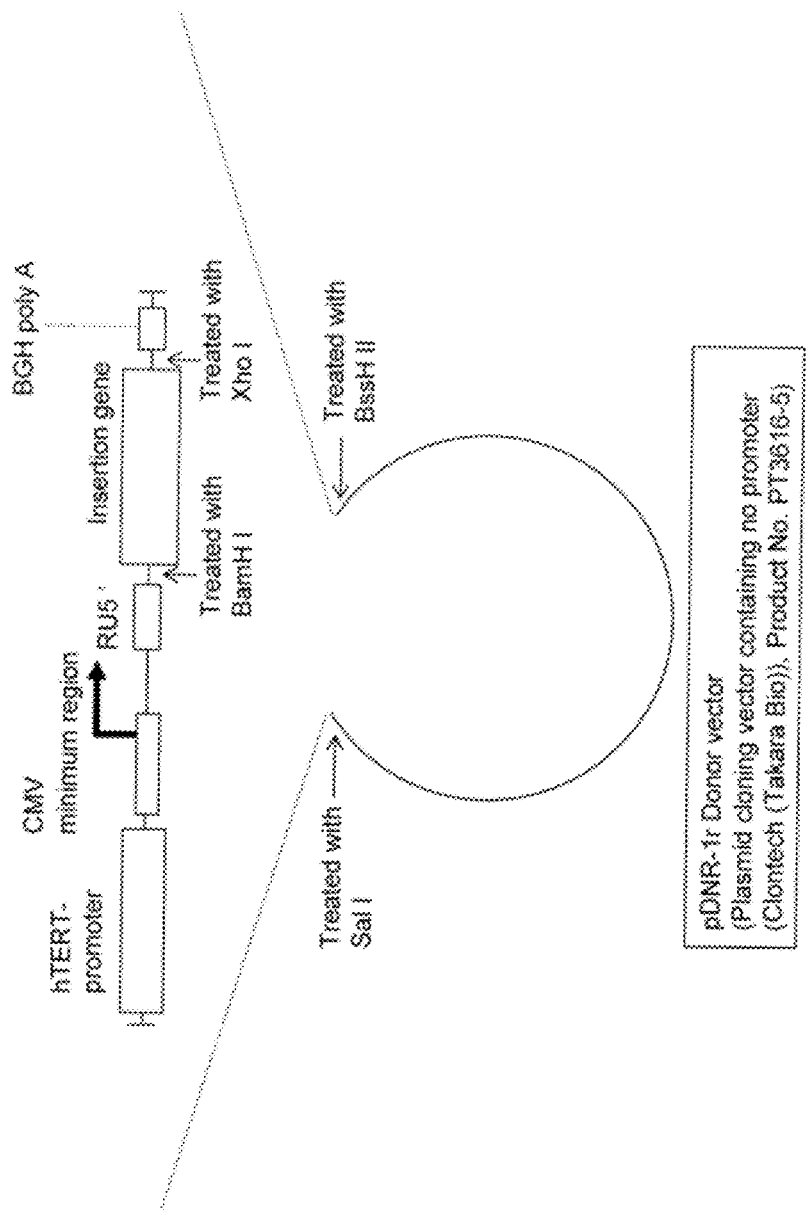
FIG. 56 shows the structure of construct No. 19.

FIG. 54 shows the results. Lane 1 shows the result of a cell extract of cells transfected with a commercial pShuttle vector to which an REIC-coding DNA had been inserted, lane 2 shows the result of a cell extract of cells transfected with an expression vector constructed by inserting c-myc-coding DNA into a commercial pShuttle vector and then inserting 3 enhancers to a site downstream (downstream of BGH poly A) of the c-myc-coding DNA. As shown in FIG. 54, the strongest expression was observed when the expression vector constructed by inserting c-myc-coding DNA into a commercial pShuttle vector and then inserting 3 enhancers into a site downstream of the c-myc-coding DNA (downstream of BGH poly A) had been used. This result demonstrates that the gene expression can be enhanced by incorporation of the portion of 3 enhancers of this system (the backbone of construct No. 14) into a site downstream of the expression gene cassette of a commercial plasmid such as a pShuttle vector. Specifically, the result demonstrates that insertion of the region of 3 enhancers to various gene constructs can enhance target gene expression. The result of this example demonstrates that c-myc gene expression is enhanced by incorporation of the portion of 3 enhancers of this system (the backbone of construct No. 14) into a site downstream of the expression gene cassette of a plasmid for expression of a c-myc gene to be used for preparation of iPS cells. iPS cells are thought to be useful for various types of regeneration medicine. Specifically, the result demonstrates that the enhancer portion is useful for regeneration medicine and the like as a means for enabling stronger expression of namely, reprogramming genes, such as c-myc, or a means for using the thus expressed protein itself as a regeneration factor in vivo or ex vivo.

Example 7

Enhanced Expression Upon the Use of hTERT as Promoter

The expression cassettes of the present invention containing GFP (Green fluorescent protein) as a foreign gene (insertion gene) were prepared. HEK293 cells were transfected with the expression cassettes, and the thus expressed proteins were analyzed by Western blot. Transfection was carried out using FuGENE (trademark)-HD. After 24 hours, GFP in cell culture solutions was detected by Western blotting.

The constructs of the expression cassettes used herein were: construct No. 2 (FIG. 8) used in Example 1 and constructs No. 18, 19, 20, and 21. Constructs No. 18, 19, 20, and 21 are shown in FIG. 55, FIG. 56, FIG. 57, and FIG. 58, respectively. Construct No. 18 is a general gene expression vector containing an hTERT promoter. Such a gene expression vector is advantageous in strong gene expression in an environment where hTERT is expressed at a high level; that is, in cancer cells, and is used when cancer cell-specific gene expression is expected. However, the use of this vector (construct No. 18) results in extremely weak gene expression and this hinders the vector from being clinically applied to gene therapy, protein (drug) production in specific cells, and the like. Construct No. 19 is a plasmid constructed by inserting an RU5 sequence into a site upstream of an expression gene of a general gene expression vector (construct No. 18) containing an hTERT promoter. Construct No. 20 is a plasmid constructed by inserting an hTERT enhancer sequence into a site downstream of a BGH poly A sequence of a general gene expression vector (construct No. 18) containing an hTERT promoter. Construct No. 21 is a plasmid constructed by inserting an RU5' sequence into a site upstream of an expression gene of a general gene expression vector (construct No. 18) containing an hTERT promoter and further inserting an hTERT enhancer sequence into a site downstream of the BGH poly A sequence. FIG. 59-1 and FIG. 59-2 (a continuation from FIG. 59-1) show the full nucleotide sequence (SEQ ID NO: 31) of expression vector construct No. 21. Portions surrounded by frames (1), (2), (3), (4), and (5) in the nucleotide sequence shown in FIG. 59-1 and FIG. 59-2 indicate an hTERT core promoter, a minimal CMV promoter, RU5', a GFP gene, BGH poly A, and an hTERT core promoter, respectively.

Figure 60:
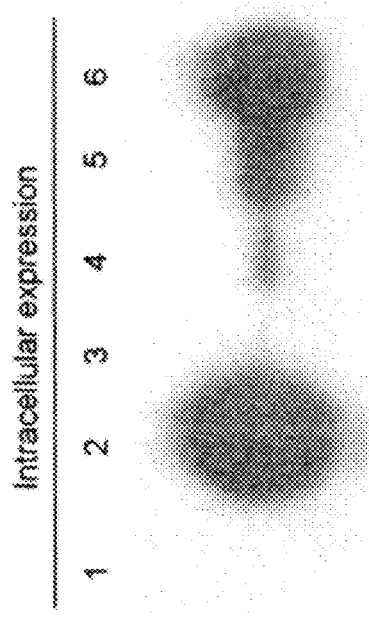
FIG. 60 shows the result of insertion of a gene of interest into a plasmid containing an hTERT promoter and the following expression thereof.

FIG. 60 shows the results of expression. Lane 1 shows the results for a cell extract of cells not caused to express any foreign protein, and lanes 2 to 6 show the results of expression using constructs No. 2, No. 18, No. 19, No. 20, and No. 21, separately. As shown in FIG. 60, expression was observed descending order of strength in constructs No. 18, No. 19, No. 20, No. 21 and No. 2. The results for this example demonstrate that this system (the form of the constructs wherein a target expression gene is flanked by a promoter and an enhancer) is useful for significantly enhancing the gene expression of an hTERT promoter that enables cancer-specific gene expression but has extremely weak gene expression capacity.

Example 8

Expression Upon Simultaneous Transfection with a Plurality of Expression Vectors Having Different Foreign Genes Incorporated Therein Cells were transfected simultaneously with a plasmid constructed by incorporating DsRed (red fluorescent protein)-coding DNA into construct No. 2 (FIG. 20), a plasmid constructed by incorporating Yeast GST (Glutathione S transferase)-coding DNA into construct No. 21 (FIG. 58), and a plasmid constructed by incorporating GFP-coding DNA into construct No. 21 (FIG. 58). The thus expressed proteins were analyzed by Western blot. Transfection was carried out using FuGENE (trademark)-HD. As cells, cells of cancer cell lines, HEK293 cells, Hela cells, PC3 cells, HepG2 cells, HCT116 cells, and MCF7 cells were used. Furthermore, as cells of a normal cell line, OUMS-24 cells (human-derived fibroblasts) and NHK cells (human-derived keratinocyte cells) were used. At 48 hours after transfection, each protein in cell extracts was detected by Western blotting. For DsRed-coding DNA and Yeast GST-coding DNA, cDNAs were prepared by artificial synthesis based on known cDNA sequences.

Western blotting was carried out using an anti-GFP antibody, an anti-6His antibody (MBL, used for detection of 6His-added Telomerase), an anti-tubulin antibody (Sigma), an anti-DsRed antibody (Clontech), and an anti-Yeast GST antibody and cell extracts obtained at 24 hours after transfection (total protein amount: 10 μg).

Figure 61:
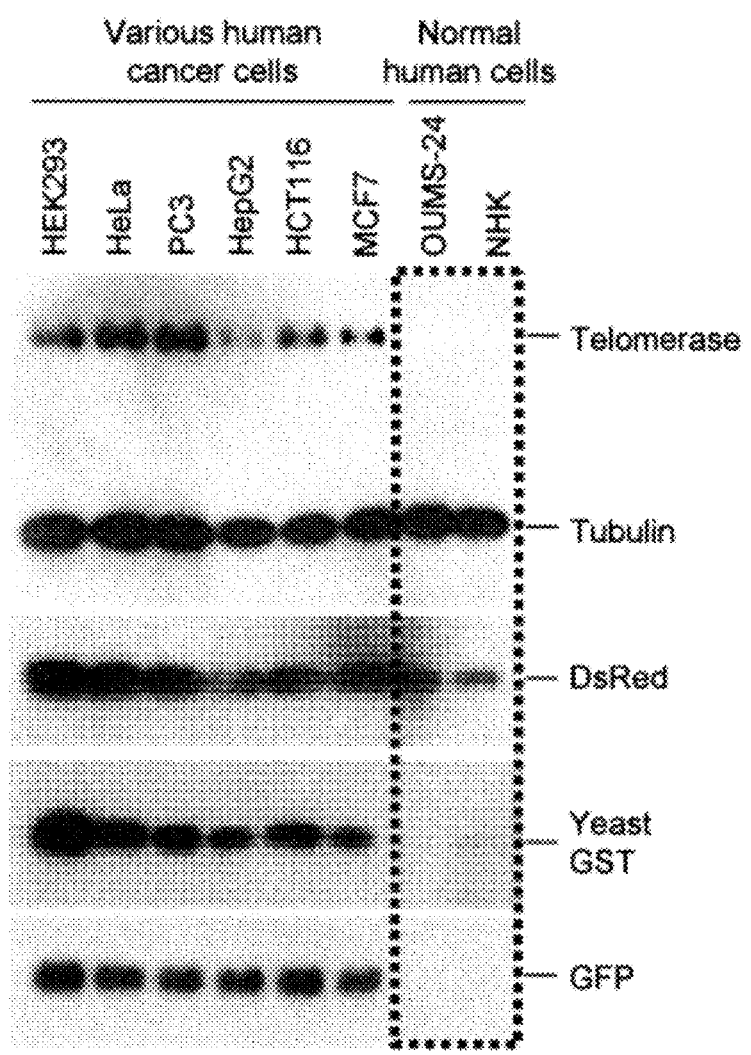
FIG. 61 shows the expression after simultaneous transfection of a plurality of expression vectors into which different foreign genes were incorporated.

FIG. 61 shows the results. As shown in FIG. 61, a plasmid construct (construct No. 21) containing an hTERT promoter is useful for carrying out gene expression specific to only cancer cells in various cancer cells and normal cells. Specifically, in this case, genes were expressed strongly only in cancer cells, and gene expression in normal cells can be suppressed. In this regard, for example, gene expression is observed in both human cancer cells and normal cells in the case of a plasmid construct (construct No. 2) containing a CMV promoter, so that cancer-cell-specific gene expression cannot be achieved. As described above, a plasmid containing an hTERT promoter is useful in that cancer-cell-specific gene expression can be achieved.

Example 9

Examination of the Production Amount of Human Erythropoietin (Human EPO) by HEK293 Cells (Human Embryonic Kidney Cells) Transfected with Expression Vector Containing the Gene Expression Cassette of the Present Invention For secretory expression of human erythropoietin, the DNA fragment of EPO-His tag having the His-tagged C-terminus was incorporated into a vector (referred to as SGE (Super Gene Expression) vector) containing construct No. 14 and the same was incorporated into a pTracer (registered trademark)-EF vector (EF-1α promoter, Invitrogen) as a control.

Figure 62:
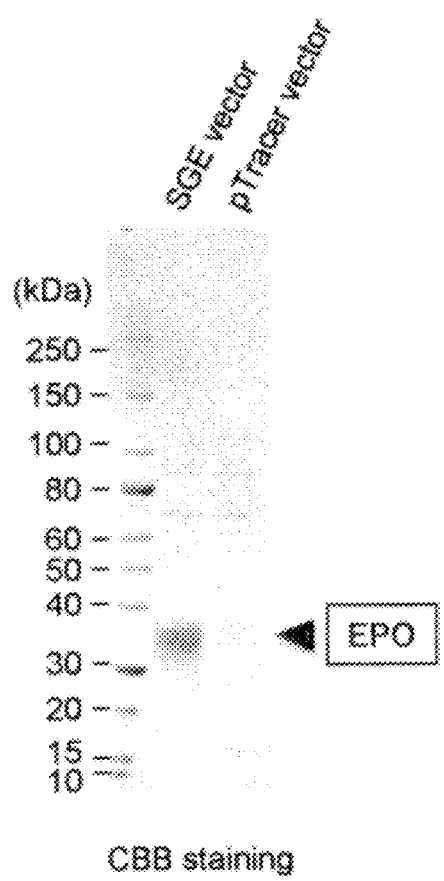
FIG. 62 shows the production of human erythropoietin using the expression vectors of the present invention.

As host cells for secretory expression of human erythropoietin, 30 mL of human kidney-derived cells (FreeStyle 293-F cells (Invitrogen)) at the logarithmic growth phase was seeded at a concentration of $5$-$6 \times 10^5$ cells/mL to a 125 mL-flask. The cells were cultured with shake (125 rpm) overnight at 37° C. in the presence of 8% $CO_2$ using Freestyle 293 Expression 1 Media (Invitrogen). On the next day, the cell concentration was adjusted to $1 \times 10^6$ cells/mL. To 125-mL flask to which 30 mL of 293-F cells had been seeded, 30 μg each of SGE-EPO-His-tag plasmid DNA and pTracer (registered trademark)-EF-EPO-His-tag plasmid DNA were mixed with a transfection reagent: 293 Fectin (Invitrogen) and then transfection was carried out. During 4 days after transfection, cells were cultured with shake at 37° C. in the presence of 8% $CO_2$, and then a culture supernatant was collected. 18 μL of the culture supernatant was separated on SDS-PAGE, and then a glycosylation-type EPO protein with a molecular weight of about 35 kDa was detected by CBB staining (FIG. 62).

Figure 63:
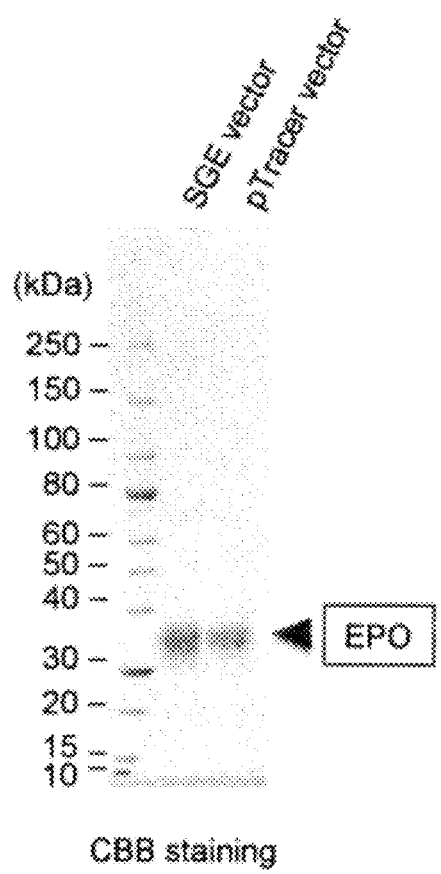
FIG. 63 shows the purity of human erythropoietin produced using the expression vectors of the present invention.

For estimation of the production amount of EPO, the human erythropoietin protein secreted in 25 mL of a culture supernatant collected 4 days later was purified using histidine affinity column chromatography (TALON-Affinity Resin (Clontech)). The eluate was separated on SDS-PAGE and then the purity of the EPO protein was confirmed by CBB staining (FIG. 63). The protein amount of the purified EPO protein was determined by Bradford assay, and then the protein amount obtained in the case of 1 L of the culture solution was calculated from the amount of the purified protein in the case of 25 mL of the culture solution (FIGS. 64A and B). As a result, human erythropoietin could be produced with the use of the SGE vector at an expression level about 8 times higher than that in the case of using the pTracer (registered trademark)-EF vector. Therefore, an extremely highly efficient expression level; that is, about 150 mg (in terms of the level in the case of 1 L of the culture solution), was achieved.

Example 10

Figure 65:
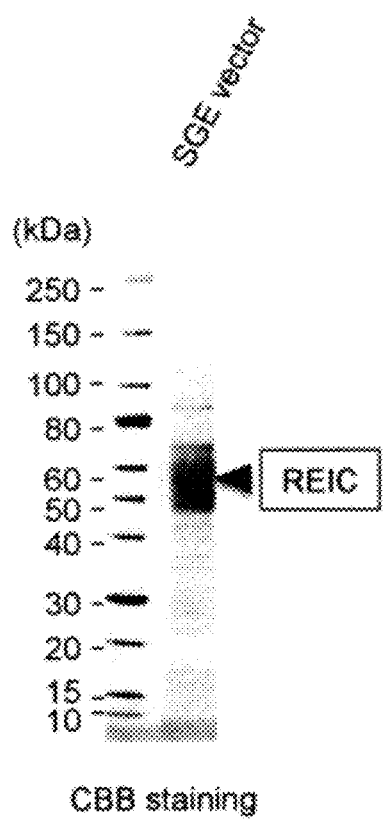
FIG. 65 shows human REIC protein production using the expression vector of the present invention.

Examination of Production Amount of Human REIC (Reduced Expression in Immortalized Cells) Protein by HEK293 Cells (Human Embryonic Kidney Cells) Transfected with Expression Vector Containing the Gene Expression Cassette of the Present Invention According to the method described in Example 1, 293-F cells were adjusted to a concentration of $1 \times 10^6$ cells/mL and then 180 mL of the solution was seeded in each of three 500-mL flasks. Each flask was subjected to transient transfection with an REIC expression SGE vector (the vector containing construct No. 14) (180 μg) using a transfection reagent: 293 Fectin (Invitrogen). During 4 days after transfection, cells were cultured with shake at 37° C. in the presence of 8% $CO_2$, and thus culture supernatants were collected. Each culture supernatant (18 μL) was separated on SDS-PAGE, and then a glycosylated REIC protein with a molecular weight of about 55 kDa was detected by CBB staining (FIG. 65).

Figure 66:
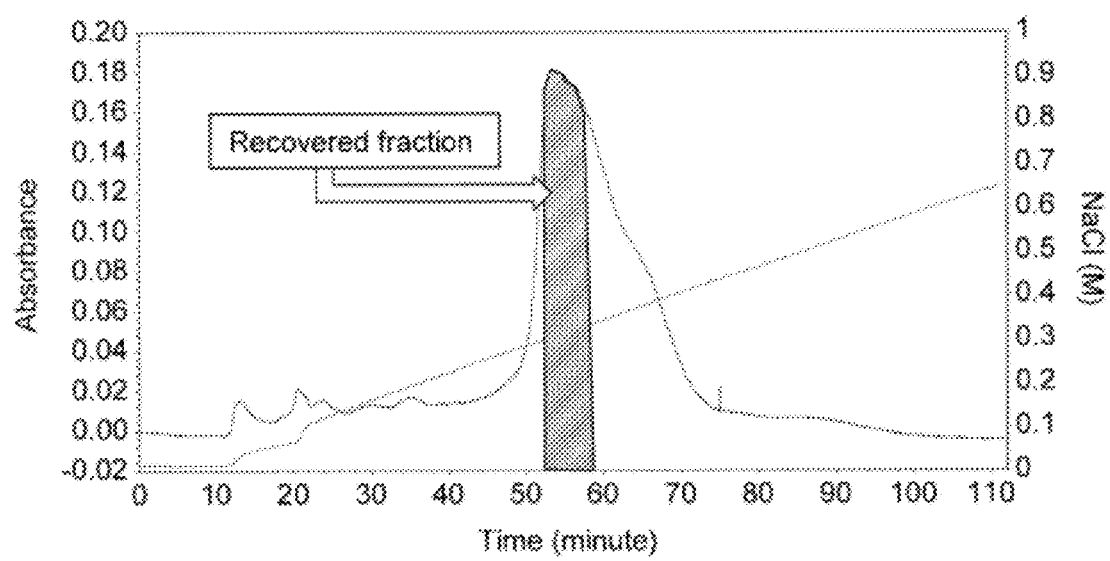
FIG. 66 shows an ion exchange column chromatogram for a human REIC protein produced using the expression vector of the present invention.

The collected culture supernatants were each concentrated by ultrafiltration from 520 mL to 35 mL. The solvent was substituted with 20 mM Hepes Buffer (pH7.2) using Sephadex (Trademark) G25M column chromatography (GE Healthcare), and then a REIC protein-containing fraction was collected. Thereafter, protein adsorption was carried out using anion exchange column chromatography (DEAE-Toyopearl (registered trademark) 650 M, TOSOH Corporation), and then elution was carried out in 20 mM Hepes Buffer (pH 7.2) with a linear concentration gradient (0 M to 0.7 M) of sodium chloride. Under the conditions of the sodium chloride concentration of about 0.35 M, the peak fractions of the REIC protein was confirmed. Each peak fraction was analyzed by SDS-PAGE, and thus fractions composed only of the REIC protein with high purity were collected (FIG. 66). The protein amount of the purified REIC protein was calculated using absorbance (280 nm) and the purified protein amount in the case of 520 mL of the culture solution, so that the protein amount obtained in the case of 1 L of the culture solution was calculated (FIG. 67). As a result, about 50 mg of the purified protein with high purity could be obtained from the culture supernatant subjected to transfection with the REIC expression SGE vector. Specifically, it was demonstrated that the purified protein can be actually collected in an amount as large as about 100 mg in terms of 1 L of the culture solution.

INDUSTRIAL APPLICABILITY

The gene expression cassette of the present invention comprises a DNA construct containing a gene to be expressed and a poly A addition sequence that are located downstream of a $1^{st}$ promoter, wherein an enhancer or a $2^{nd}$ promoter is ligated downstream of the DNA construct. The gene expression cassette realizes the mass production of a target protein through super-high expression, regardless of cell type, gene type, and transfection reagent type. The gene expression cassette can be applied as a reagent in the field of biotechnology and can also be applied extensively as a therapeutic protein remedy or for clinical treatment, examination, and diagnosis using genes. For example, the gene expression cassette can facilitate revolutionary evolution techniques in the field of biotechnology, such as: (1) the functional analysis of unknown genes in specific cells or tissues that have conventionally remained unanalyzed; (2) improvement of therapeutic effects via loading both viral and non-viral vectors with the gene expression cassette in gene therapy; (3) preparation of super cells capable of producing large amounts of a specific human functional protein with the use of human cells, as a method for producing biopharmaceutical products such as antibody drugs used in recent years; and (4) application for an efficient and inexpensive method for producing reagents or diagnostic agents to be used for various forms of assay or clinical diagnosis.

The DNA expression cassette of the present invention can be applied as a reagent in the field of biotechnology and can also be extensively applied for clinical treatment, examination, and diagnosis using genes.

SEQUENCE LISTING FREE TEXT

SEQ ID NOs: 1-16, 19-31 Synthesis

The invention claimed is:

1. A gene expression cassette, which comprises:
   (i) a DNA construct in which a promoter, a gene to be expressed, and a polyA addition sequence are linked in such order; and
   (ii) enhancer(s) or enhancer(s) with an upstream activation sequence (UAS) ligated to the upstream portion thereof, which comprises at least an hTERT enhancer, in such order, wherein the enhancer(s) or the enhancer(s) with a UAS ligated to the upstream portion thereof is ligated immediately downstream of the polyA addition sequence, and can increase the protein expression from the gene compared to a gene expression cassette in which the enhancer(s) are inserted upstream of the promoter.

2. The expression cassette according to claim 1, which does not have another mechanism for gene expression at a site downstream of the ligated enhancer, but has a structure in which a gene to be expressed is flanked by the promoter and the enhancer.

3. The expression cassette according to claim 1, wherein the promoter is selected from the group consisting of a CMV promoter, a CMV i promoter, an SV40 promoter, an hTERT promoter, a β actin promoter, and a CAG promoter.

4. The expression cassette according to claim 1, wherein the enhancer(s) ligated downstream of the polyA addition sequence further comprises at least one enhancer selected from the group consisting of a CMV enhancer, and an SV40 enhancer.

5. The expression cassette according to claim 1, wherein the enhancers ligated downstream of the polyA addition sequence are an hTERT enhancer, an SV40 enhancer, and a CMV enhancer that are linked in such order.

6. The expression cassette according to claim 1, containing at least one of the following elements (i) and (ii):
   (i) RU5' ligated immediately upstream of a gene to be expressed; and
   (ii) SV40-ori ligated to the most upstream portion of the expression cassette.

7. The expression cassette according to claim 1, wherein DNA encoding the protein to be expressed is a therapeutic gene that can be used for treatment of disease, or DNA encoding a protein that can be used for a drug, a diagnostic agent, or a reagent.

8. The expression cassette according to claim 7, wherein the therapeutic gene is a REIC/Dkk-3 gene that is a cancer suppressor gene applicable for the treatment of tumors.

9. The expression cassette according to claim 1, wherein the promoter is an hTERT promoter and the enhancer is an hTERT enhancer.

10. The expression cassette according to claim 1, wherein the promoter is an hTERT promoter, is a CMV promoter, or a CMVi promoter and the enhancer is an hTERT enhancer.

11. A vector, containing the expression cassette according to claim 1.

12. The vector according to claim 11, which is an adenovirus vector or an adeno-associated virus vector.

13. A host cell, containing the vector according to claim 11 or 12.

14. A preparation for disease detection or treatment, comprising the vector according to claim 11.

15. A method for expressing a gene to be expressed using the expression cassette according to claim 1 or the vector according to claim 11, comprising introducing the expression cassette or vector into cells.

16. A method for producing a protein encoded by a gene to be expressed, comprising introducing the expression cassette according to claim 1 or the vector according to claim 11 into a cell, and then culturing the cell.

* * * * *

SEQUENCE LISTING

```
<160> NUMBER OF SEQ ID NOS: 32

<210> SEQ ID NO 1
<211> LENGTH: 50
<212> TYPE: DNA
<213> ORGANISM: Artificial
<220> FEATURE:
<223> OTHER INFORMATION: Synthetic

<400> SEQUENCE: 1
gcggccgcat aacttcgtat agcatacatt atacgaagtt atcagtcgac            50

<210> SEQ ID NO 2
<211> LENGTH: 4579
```

<212> TYPE: DNA
<213> ORGANISM: Artificial
<220> FEATURE:
<223> OTHER INFORMATION: Synthetic

<400> SEQUENCE: 2

| | | | | | |
|---|---|---|---|---|---|
| gcgcgcgggc | ccagtaggta | agtgaacatg | gtcatagctg | tttcctagga | gatcctggtc | 60 |
| atgactagtg | cttggattct | caccaataaa | aaacgcccgg | cggcaaccga | gcgttctgaa | 120 |
| caaatccaga | tggagttctg | aggtcattac | tggatctatc | aacaggagtc | caagcgagct | 180 |
| cgatatcaaa | ttacgccccg | ccctgccact | catcgcagta | ctgttgtaat | tcattaagca | 240 |
| ttctgccgac | atggaagcca | tcacaaacgg | catgatgaac | ctgaatcgcc | agcggcatca | 300 |
| gcaccttgtc | gccttgcgta | taatatttgc | ccatggtgaa | acgggggcg | aagaagttgt | 360 |
| ccatattggc | cacgttttaaa | tcaaaactgg | tgaaactcac | ccagggattg | gctgagacga | 420 |
| aaaacatatt | ctcaataaac | cctttaggga | ataggccag | gttttcaccg | taacacgcca | 480 |
| catcttgcga | atatatgtgt | agaaactgcc | ggaaatcgtc | gtggtattca | ctccagagcg | 540 |
| atgaaaacgt | ttcagtttgc | tcatggaaaa | cggtgtaaca | agggtgaaca | ctatccata | 600 |
| tcaccagctc | accgtctttc | attgccatac | gaaattccgg | atgagcattc | atcaggcggg | 660 |
| caagaatgtg | aataaaggcc | ggataaaact | tgtgcttatt | tttctttacg | gtctttaaaa | 720 |
| aggccgtaat | atccagctga | acggtctggt | tataggtaca | ttgtgtgatt | aaaaaggcaa | 780 |
| ctttatgccc | atgcaacaga | aactataaaa | aatacagaga | atgaaaagaa | acagatagat | 840 |
| ttttagttc | tttaggcccg | tagtctgcaa | atccttttat | gattttctat | caaacaaaag | 900 |
| aggaaaatag | accagttgca | atccaaacga | gagtctaata | gaatgaggtc | gaaaagtaaa | 960 |
| tcgcgcgggt | ttgttactga | taaagcaggc | aagacctaaa | atgtgtaaag | ggcaaagtgt | 1020 |
| atactttggc | gtcacccctt | acatatttta | ggtctttttt | tattgtgcgt | aactaacttg | 1080 |
| ccatcttcaa | acaggagggc | tggaagaagc | agaccgctaa | cacagtacat | aaaaaaggag | 1140 |
| acatgaacga | tgaacatcaa | aaagtttgca | aaacaagcaa | cagtattaac | ctttactacc | 1200 |
| gcactgctgg | caggaggcgc | aactcaagcg | tttgcgaaag | aaacgaacca | aaagccatat | 1260 |
| aaggaaacat | acggcatttc | ccatattaca | cgccatgata | tgctgcaaat | ccctgaacag | 1320 |
| caaaaaaatg | aaaaatatca | agttcctgag | ttcgattcgt | ccacaattaa | aaatatctct | 1380 |
| tctgcaaaag | gcctggacgt | ttgggacagc | tggccattac | aaaacgctga | cggcactgtc | 1440 |
| gcaaactatc | acggctacca | catcgtcttt | gcattagccg | gagatcctaa | aaatgcggat | 1500 |
| gacacatcga | tttacatgtt | ctatcaaaaa | gtcggcgaaa | cttctattga | cagctggaaa | 1560 |
| aacgctggcc | gcgtctttaa | agacagcgac | aaattcgatg | caaatgattc | tatcctaaaa | 1620 |
| gaccaaacac | aagaatggtc | aggttcagcc | acatttacat | ctgacggaaa | aatccgttta | 1680 |
| ttctacactg | atttctccgg | taaacattac | ggcaaacaaa | cactgacaac | tgcacaagtt | 1740 |
| aacgtatcag | catcagacag | ctctttgaac | atcaacggtg | tagaggatta | taaatcaatc | 1800 |
| tttgacggtg | acggaaaaac | gtatcaaaat | gtacagcagt | tcatcgatga | aggcaactac | 1860 |
| agctcaggcg | acaaccatac | gctgagagat | cctcactacg | tagaagataa | aggccacaaa | 1920 |
| tacttagtat | ttgaagcaaa | cactggaact | gaagatggct | accaaggcga | agaatcttta | 1980 |
| tttaacaaag | catactatgg | caaaagcaca | tcattcttcc | gtcaagaaag | tcaaaaactt | 2040 |
| ctgcaaagcg | ataaaaaacg | cacggctgag | ttagcaaacg | gcgctctcgg | tatgattgag | 2100 |
| ctaaacgatg | attacacact | gaaaaaagtg | atgaaaccgc | tgattgcatc | taacacagta | 2160 |

```
acagatgaaa ttgaacgcgc gaacgtcttt aaaatgaacg gcaaatggta cctgttcact    2220
gactcccgcg gatcaaaaat gacgattgac ggcattacgt ctaacgatat ttacatgctt    2280
ggttatgttt ctaattcttt aactggccca tacaagccgc tgaacaaaac tggccttgtg    2340
ttaaaaatgg atcttgatcc taacgatgta acctttactt actcacactt cgctgtacct    2400
caagcgaaag gaaacaatgt cgtgattaca agctatatga caaacagagg attctacgca    2460
gacaaacaat caacgtttgc gcctagcttc ctgctgaaca tcaaaggcaa gaaaacatct    2520
gttgtcaaag acagcatcct tgaacaagga caattaacag ttaacaaata aaaacgcaaa    2580
agaaaatgcc gatatcctat tggcattgac gtcaggtggc acttttcggg gaaatgtgcg    2640
cggaacccct atttgtttat ttttctaaat acattcaaat atgtatccgc tcatgagaca    2700
ataaccctga taaatgcttc aataatattg aaaaaggaag agtatgagta ttcaacattt    2760
ccgtgtcgcc cttattccct tttttgcggc attttgcctt cctgttttg ctcacccaga    2820
aacgctggtg aaagtaaaag atgctgaaga tcagttgggt gcacgagtgg gttacatcga    2880
actggatctc aacagcggta agatccttga gagttttcgc cccgaagaac gttttccaat    2940
gatgagcact tttaaagttc tgctatgtgg cgcggtatta tcccgtattg acgccgggca    3000
agagcaactc ggtcgccgca tacactattc tcagaatgac ttggttgagt actcaccagt    3060
cacagaaaag catcttacgg atggcatgac agtaagagaa ttatgcagtg ctgccataac    3120
catgagtgat aacactgcgg ccaacttact tctgacaacg atcggaggac cgaaggagct    3180
aaccgctttt ttgcacaaca tgggggatca tgtaactcgc cttgatcgtt gggaaccgga    3240
gctgaatgaa gccataccaa acgacgagcg tgacaccacg atgcctgtag caatggcaac    3300
aacgttgcgc aaactattaa ctggcgaact acttactcta gcttcccggc aacaattaat    3360
agactggatg gaggcggata agttgcagg accacttctg cgctcggccc ttccggctgg    3420
ctggtttatt gctgataaat ctggagccgg tgagcgtggg tctcgcggta tcattgcagc    3480
actggggcca gatggtaagc cctcccgtat cgtagttatc tacacgacgg ggagtcaggc    3540
aactatggat gaacgaaata gacagatcgc tgagataggt gcctcactga ttaagcattg    3600
gtaactgtca gaccaagttt actcatatat actttagatt gatttaaaac ttcattttta    3660
atttaaaagg atctaggtga agatccttt tgataatctc atgaccaaaa tcccttaacg    3720
tgagttttcg ttccactgag cgtcagaccc cgtagaaaag atcaaaggat cttcttgaga    3780
tcctttttt ctgcgcgtaa tctgctgctt gcaaacaaaa aaaccaccgc taccagcggt    3840
ggtttgtttg ccggatcaag agctaccaac tcttttttccg aaggtaactg gcttcagcag    3900
agcgcagata ccaaatactg ttcttctagt gtagccgtag ttaggccacc acttcaagaa    3960
ctctgtagca ccgcctacat acctcgctct gctaatcctg ttaccagtgg ctgctgccag    4020
tggcgataag tcgtgtctta ccgggttgga ctcaagacga tagttaccgg ataaggcgca    4080
gcggtcgggc tgaacggggg gttcgtgcac acagcccagc ttggagcgaa cgacctacac    4140
cgaactgaga tacctacagc gtgagctatg agaaagcgcc acgcttcccg aagggagaaa    4200
ggcggacagg tatccggtaa gcggcagggt cggaacagga gagcgcacga gggagcttcc    4260
agggggaaac gcctggtatc tttatagtcc tgtcgggttt cgccacctct gacttgagcg    4320
tcgatttttg tgatgctcgt caggggggcg gagcctatgg aaaaacgcca gcaacgcggc    4380
ctttttacgg ttcctggcct tttgctggcc ttttgctcac atgttctttc ctgcgttatc    4440
ccctgattct gtggataacc gtattaccgc cttgcgcgtg taaaacgacg gccagtgagat    4500
ctgtaatacg actcactata gggcgctagc tgctcgccgc agccgaacga ccgagcgcag    4560
```

| cgagtcagtg agcgaggaa | 4579 |

<210> SEQ ID NO 3
<211> LENGTH: 604
<212> TYPE: DNA
<213> ORGANISM: Artificial
<220> FEATURE:
<223> OTHER INFORMATION: Synthetic

<400> SEQUENCE: 3

| gggctgtgtg cacgaacccc ccgttcagcc cgaccgctgc gccttatccg gtaactatcg | 60 |
| tcttgagtcc aacccggtaa gacacgactt atcgccactg gcagcagcca ctggtaacag | 120 |
| gattagcaga gcgaggtatg taggcggtgc tacagagttc ttgaagtggt ggcctaacta | 180 |
| cggctacact agaagaacag tatttggtat ctgcgctctg ctgaagccag ttacctcgga | 240 |
| aaaagagttg gtagctcttg atccggcaaa caaaccaccg ctggtagcgg tggtttttt | 300 |
| gtttgcaagc agcagattac gcgcagaaaa aaggatctca agaagatcc tttgattttc | 360 |
| taccgaagaa aggcccaccc gtgaaggtga gccagtgagt tgattgcagt ccagttacgc | 420 |
| tggagtctga ggctcgtcct gaatgtgtaa acgacggcc agtttatcta gtcagcttga | 480 |
| ttctagctga tcgtggaccg gaaggtgagc cagtgagttg attgcagtcc agttacgctg | 540 |
| gagtctgagg ctcgtcctga atgatatacg cgtcggaggg ttgcgtttga dacgggcgac | 600 |
| agat | 604 |

<210> SEQ ID NO 4
<211> LENGTH: 1423
<212> TYPE: DNA
<213> ORGANISM: Artificial
<220> FEATURE:
<223> OTHER INFORMATION: Synthetic

<400> SEQUENCE: 4

| atcagttctg gacgagcgag ctgtcgtccg gcggccgcga tcttacggca ttatacgtat | 60 |
| gatcggtcca cgatcagcta gattatctag tcagcttgat gtcatagctg tttcctgagg | 120 |
| ctcaatactg accatttaaa tcatacctga cctccatagc agaaagtcaa aagcctccga | 180 |
| ccggaggctt ttgacttgat cggcacgtaa gaggttccaa ctttcaccat aatgaaataa | 240 |
| gatcactacc gggcgtattt tttgagttat cgagattttc aggagctaag gaagctaaaa | 300 |
| tgagccatat tcaacgggaa acgtcttgct tgaagccgcg attaaattcc aacatggatg | 360 |
| ctgatttata tgggtataaa tgggctcgcg ataatgtcgg gcaatcaggt gcgacaatct | 420 |
| atcgattgta tgggaagccc gatgcgccag agttgtttct gaaacatggc aaaggtagcg | 480 |
| ttgccaatga tgttacagat gagatggtca ggctaaactg gctgacggaa tttatgcctc | 540 |
| ttccgaccat caagcatttt atccgtactc ctgatgatgc atggttactc accactgcga | 600 |
| tccccagggaa aacagcattc caggtattag aagaatatcc tgattcaggt gaaaatattg | 660 |
| ttgatgcgct ggcagtgttc ctgcgccggt tgcattcgat tcctgtttgt aattgtcctt | 720 |
| ttaacggcga tcgcgtattt cgtctcgctc aggcgcaatc acgaatgaat aacggtttgg | 780 |
| ttgatgcgag tgattttgat gacgagcgta atggctggcc tgttgaacaa gtctggaaag | 840 |
| aaatgcataa actcttgcca ttctcaccgg attcagtcgt cactcatggt gatttctcac | 900 |
| ttgataaccct tatttttgac gaggggaaat taataggttg tattgatgtt ggacgagtcg | 960 |
| gaatcgcaga ccgataccag gatcttgcca tcctatggaa ctgcctcggt gagttttctc | 1020 |

| | |
|---|---|
| cttcattaca gaaacggctt tttcaaaaat atggtattga taatcctgat atgaataaat | 1080 |
| tgcagtttca cttgatgctc gatgagtttt tctaatgagg acctaaatgt aatcacctgg | 1140 |
| ctcaccttcg ggtgggcctt tctgcgttgc tggcgttttt ccataggctc cgccccctg | 1200 |
| acgagcatca caaaaatcga tgctcaagtc agaggtggcg aaacccgaca ggactataaa | 1260 |
| gataccaggc gtttccccct ggaagctccc tcgtgcgctc tcctgttccg accctgccgc | 1320 |
| ttaccggata cctgtccgcc tttctccctt cgggaagcgt ggcgctttct catagctcac | 1380 |
| gctgtaggta tctcagttcg gtgtaggtcg ttcgctccaa gct | 1423 |

<210> SEQ ID NO 5
<211> LENGTH: 754
<212> TYPE: DNA
<213> ORGANISM: Artificial
<220> FEATURE:
<223> OTHER INFORMATION: Synthetic

<400> SEQUENCE: 5

| | |
|---|---|
| tccgcgttac ataacttacg gtaaatggcc cgcctggctg accgcccaac gaccccgcc | 60 |
| cattgacgtc aataatgacg tatgttccca tagtaacgcc aatagggact ttccattgac | 120 |
| gtcaatgggt ggagtattta cggtaaactg cccacttggc agtacatcaa gtgtatcata | 180 |
| tgccaagtac gccccctatt gacgtcaatg acggtaaatg gcccgcctgg cattatgccc | 240 |
| agtacatgac cttatgggac tttcctactt ggcagtacat ctacgtatta gtcatcgcta | 300 |
| ttaccatggt gatgcggttt tggcagtaca tcaatgggcg tggatagcgg tttgactcac | 360 |
| ggggatttcc aagtctccac cccattgacg tcaatgggag tttgttttgg caccaaaatc | 420 |
| aacgggactt tccaaaatgt cgtaacaact ccgccccatt gacgcaaatg ggcggtaggc | 480 |
| gtgtacggtg ggaggtctat ataagcagag ctcgtttagt gaaccgtcag atcgcctgga | 540 |
| gacgccatcc acgctgtttt gacctccata agagacaccg gaccgatcc agcctccgcg | 600 |
| gccgggaacg gtgcattgga acgcggattc ccgtgccaa gagtgacgta agtaccgcct | 660 |
| atagactcta taggcacacc cctttggctc ttatgcatga attaatacga ctcactatag | 720 |
| ggagacagac tgttcctttc ctgggtcttt tctg | 754 |

<210> SEQ ID NO 6
<211> LENGTH: 262
<212> TYPE: DNA
<213> ORGANISM: Artificial
<220> FEATURE:
<223> OTHER INFORMATION: Synthetic

<400> SEQUENCE: 6

| | |
|---|---|
| tgactgactg acgtttaaac ccgctgatca gcctcgactg tgccttctag ttgccagcca | 60 |
| tctgttgttt gcccctcccc cgtgccttcc ttgaccctgg aaggtgccac tcccactgtc | 120 |
| ctttcctaat aaaatgagga aattgcatcg cattgtctga gtaggtgtca ttctattctg | 180 |
| gggggtgggg tgggcagga cagcaagggg gaggattggg aagacaatag caggcatgct | 240 |
| ggggatgcgg tgggctctat gg | 262 |

<210> SEQ ID NO 7
<211> LENGTH: 310
<212> TYPE: DNA
<213> ORGANISM: Artificial
<220> FEATURE:
<223> OTHER INFORMATION: Synthetic

<400> SEQUENCE: 7

```
tccgcgttac ataacttacg gtaaatggcc cgcctggctg accgcccaac gaccccccgcc    60 cattgacgtc aataatgacg tatgttccca tagtaacgcc aatagggact ttccattgac   120
gtcaatgggt ggagtattta cggtaaactg cccacttggc agtacatcaa gtgtatcata   180
tgccaagtac gccccctatt gacgtcaatg acggtaaatg gcccgcctgg cattatgccc   240
agtacatgac cttatgggac tttcctactt ggcagtacat ctacgtatta gtcatcgcta   300
ttaccatggt                                                          310
```

<210> SEQ ID NO 8
<211> LENGTH: 1508
<212> TYPE: DNA
<213> ORGANISM: Artificial
<220> FEATURE:
<223> OTHER INFORMATION: Synthetic

<400> SEQUENCE: 8

```
gttccatgtc cttatatgga ctcatctttg cctattgcga cacacactca gtgaacacct    60
actacgcgct gcaaagagcc ccgcaggcct gaggtgcccc cacctcacca ctcttcctat   120
ttttgtgtaa aaatccagct tcttgtcacc acctccaagg aggggagga ggaggaaggc   180 aggttcctct aggctgagcc gaatgcccct ctgtggtccc acgccactga tcgctgcatg   240
cccaccacct gggtacacac agtctgtgat tccggagca gaacggaccc tgcccacccg   300
gtcttgtgtg ctactcagtg gacagaccca aggcaagaaa gggtgacaag gacagggtct   360
tcccaggctg gctttgagtt cctagcaccg cccccgcccc aatcctctgt ggcacatgga   420
gtcttggtcc ccagagtccc ccagcggcct ccagatggtc tgggagggca gttcagctgt   480
ggctgcgcat agcagacata caacggacgg tgggcccaga cccaggctgt gtagacccag   540
cccccccgcc ccgcagtgcc taggtcaccc actaacgccc caggccttgt cttggctggg   600
cgtgactgtt accctcaaaa gcaggcagct ccagggtaaa aggtgccctg ccctgtagag   660
cccaccttcc ttcccagggc tgcggctggg taggtttgta gccttcatca cgggccacct   720
ccagccactg gaccgctggc ccctgccctg tcctggggag tgtggtcctg cgacttctaa   780
gtggccgcaa gccacctgac tcccccaaca ccacactcta cctctcaagc ccaggtctct   840
ccctagtgac ccacccagca catttagcta gctgagcccc acagccagag gtcctcaggc   900
cctgctttca gggcagttgc tctgaagtcg gcaagggga gtgactgcct ggccactcca   960
tgccctccaa gagctccttc tgcaggagcg tacagaaccc agggccctgg cacccgtgca  1020
gaccctggcc caccccacct gggcgctcag tgcccaagag atgtccacac ctaggatgtc  1080
ccgcggtggg tggggggccc gagagacggg caggccgggg gcaggcctgg ccatgcgggg  1140
ccgaaccggg cactgcccag cgtggggcgc ggggccacg gcgcgcgccc ccagcccccg  1200
ggcccagcac cccaaggcgg ccaacgccaa aactctccct cctcctcttc ctcaatctcg  1260
ctctcgctct tttttttttt cgcaaaagga ggggagaggg ggtaaaaaaa tgctgcactg  1320
tgcggcgaag ccggtgagtg agcggcgcgg ggccaatcag cgtgcgccgt tccgaaagtt  1380
gccttttatg gctcgagcgg ccgcggcggc gccctataaa acccagcggc gcgacgcgcc  1440
accaccgccg agaccgcgtc cgccccgcga gcacagagcc tcgcctttgc cgatccgccg  1500
cccgtcca                                                          1508
```

<210> SEQ ID NO 9
<211> LENGTH: 286
<212> TYPE: DNA

<213> ORGANISM: Artificial
<220> FEATURE:
<223> OTHER INFORMATION: Synthetic

<400> SEQUENCE: 9

```
agcttcgagg ggctcgcatc tctccttcac gcgcccgccg ccctacctga ggccgccatc    60
cacgccggtt gagtcgcgtt ctgccgcctc ccgcctgtgg tgcctcctga actgcgtccg   120
ccgtctaggt aagtttaaag ctcaggtcga gaccgggcct ttgtccggcg ctcccttgga   180
gcctacctag actcagccgg ctctccacgc tttgcctgac cctgcttgct caactctacg   240
tctttgtttc gttttctgtt ctgcgccgtt acagatccaa gccacc                  286
```

<210> SEQ ID NO 10
<211> LENGTH: 286
<212> TYPE: DNA
<213> ORGANISM: Artificial
<220> FEATURE:
<223> OTHER INFORMATION: Synthetic

<400> SEQUENCE: 10

```
ggtggcttgg atctgtaacg gcgcagaaca gaaaacgaaa caaagacgta gagttgagca    60
agcagggtca ggcaaagcgt ggagagccgg ctgagtctag gtaggctcca agggagcgcc   120
ggacaaaggc ccggtctcga cctgagcttt aaacttacct agacggcgga cgcagttcag   180
gaggcaccac aggcgggagg cggcagaacg cgactcaacc ggcgtggatg gcggcctcag   240
gtagggcggc gggcgcgtga aggagagatg cgagcccctc gaagct                  286
```

<210> SEQ ID NO 11
<211> LENGTH: 1012
<212> TYPE: DNA
<213> ORGANISM: Artificial
<220> FEATURE:
<223> OTHER INFORMATION: Synthetic

<400> SEQUENCE: 11

```
gtcgacgtcg ccccattgac gtcaatgggc gttacataac ttacggtaaa tggcccgcct    60
ggctgaccgc ccaacgaccc ccgcccattg acgtcaataa tgacgtatgt tcccatagta   120
acgccaatag ggactttcca ttgacgtcaa tgggtggagt atttacggta aactgcccac   180
ttggcagtac atcaagtgta tcatatgcca agtacgcccc ctattgacgt caatgacggt   240
aaatggcccg cctggcatta tgcccagtac atgacctat gggactttcc tacttggcag   300
tacatctacg tattagtcat cgctattacc atggtcccca ttgacgtcaa tgggcgttac   360
ataacttacg gtaaatggcc cgcctggctg accgcccaac gaccccgcc cattgacgtc   420
aataatgacg tatgttccca tagtaacgcc aatagggact tccattgac gtcaatgggt   480
ggagtattta cggtaaactg cccacttggc agtacatcaa gtgtatcata tgccaagtac   540
gcccctatt gacgtcaatg acggtaaatg gcccgcctgg cattatgccc agtacatgac   600
cttatgggac tttcctactt ggcagtacat ctacgtatta gtcatcgcta ttaccatggt   660
ccccattgac gtcaatgggc gttacataac ttacggtaaa tggcccgcct ggctgaccgc   720
ccaacgaccc ccgcccattg acgtcaataa tgacgtatgt tcccatagta acgccaatag   780
ggactttcca ttgacgtcaa tgggtggagt atttacggta aactgcccac ttggcagtac   840
atcaagtgta tcatatgcca agtacgcccc ctattgacgt caatgacggt aaatggcccg   900
cctggcatta tgcccagtac atgacctat gggactttcc tacttggcag tacatctacg   960
tattagtcat cgctattacc atggtcccca ttgacgtcaa tggggactgt                  1012
```

<210> SEQ ID NO 12
<211> LENGTH: 1621
<212> TYPE: DNA
<213> ORGANISM: Artificial
<220> FEATURE:
<223> OTHER INFORMATION: Synthetic

<400> SEQUENCE: 12

| | | | | | |
|---|---|---|---|---|---|
| attgattatt | gactagttat | taatagtaat | caattacggg | gtcattagtt | catagcccat | 60 |
| atatggagtt | ccgcgttaca | taacttacgg | taaatggccc | gcctggctga | ccgcccaacg | 120 |
| acccccgccc | attgacgtca | ataatgacgt | atgttcccat | agtaacgcca | atagggactt | 180 |
| tccattgacg | tcaatgggtg | gagtatttac | ggtaaactgc | ccacttggca | gtacatcaag | 240 |
| tgtatcatat | gccaagtacg | cccctattg | acgtcaatga | cggtaaatgg | cccgcctggc | 300 |
| attatgccca | gtacatgacc | ttatgggact | ttcctacttg | gcagtacatc | tacgtattag | 360 |
| tcatcgctat | taccatggtc | gaggtgagcc | ccacgttctg | cttcactctc | ccatctccc | 420 |
| cccctcccc | acccccaatt | ttgtatttat | ttattttta | attattttgt | gcagcgatgg | 480 |
| gggcggggg | ggggggcgcg | cgccaggcgg | ggcggggcgg | ggcgaggggc | ggggcggggc | 540 |
| gaggcggaga | ggtgcggcgg | cagccaatca | gagcggcgcg | ctccgaaagt | ttccttttat | 600 |
| ggcgaggcgg | cggcggcggc | ggccctataa | aaagcgaagc | gcgcggcggg | cgggagtcgc | 660 |
| tgcgcgctgc | cttcgccccg | tgccccgctc | cgccgccgcc | tcgcgccgcc | cgccccggct | 720 |
| ctgactgacc | gcgttactcc | cacaggtgag | cgggcgggac | ggcccttctc | ctccgggctg | 780 |
| taattagcgc | ttggtttaat | gacggcttgt | ttcttttctg | tggctgcgtg | aaagccttga | 840 |
| ggggctccgg | gagggccctt | tgtgcggggg | gagcggctcg | ggggtgcgt | gcgtgtgtgt | 900 |
| gtgcgtgggg | agcgccgcgt | gcggctccgc | gctgcccggc | ggctgtgagc | gctgcgggcg | 960 |
| cggcgcgggg | ctttgtgcgc | tccgcagtgt | gcgcgagggg | agcgcggccg | ggggcggtgc | 1020 |
| cccgcggtgc | ggggggggct | gcgaggggaa | caaaggctgc | gtgcggggtg | tgtgcgtggg | 1080 |
| ggggtgagca | gggggtgtgg | gcgcgtcggt | cgggctgcaa | ccccccctgc | acccccctcc | 1140 |
| ccgagttgct | gagcacggcc | cggcttcggg | tgcgggctc | cgtacggggc | gtggcgcggg | 1200 |
| gctcgccgtg | ccgggcgggg | ggtggcggca | ggtgggggtg | ccggcgggg | cggggccgcc | 1260 |
| tcgggccggg | gagggctcgg | gggagggggcg | cggcggcccc | cggagcgccg | gcggctgtcg | 1320 |
| aggcgcggcg | agccgcagcc | attgcctttt | atggtaatcg | tgcgagaggg | cgcagggact | 1380 |
| tcctttgtcc | caaatctgtg | cggagccgaa | atctgggagg | cgccgccgca | ccccctctag | 1440 |
| cgggcgcggg | gcgaagcggt | gcggcgccgg | caggaaggaa | atgggcgggg | agggccttcg | 1500 |
| tgcgtcgccg | cgccgccgtc | cccttctccc | tctccagcct | cggggctgtc | cgcggggga | 1560 |
| cggctgcctt | cggggggac | ggggcagggc | ggggttcggc | ttctggcgtg | tgaccggcgg | 1620 |
| c | | | | | | 1621 |

<210> SEQ ID NO 13
<211> LENGTH: 787
<212> TYPE: DNA
<213> ORGANISM: Artificial
<220> FEATURE:
<223> OTHER INFORMATION: Synthetic

<400> SEQUENCE: 13

| | | | | | |
|---|---|---|---|---|---|
| acgcgtcgac | gtcggccata | ccggaattcc | ggggaagatc | ttcccggggt | accccgagga | 60 |

```
ctagttcgac gccggccaag acagcacaga cagattgacc tattggggtg tttcgcgagt      120
gtgagaggga agcgccgcgg cctgtattac tagacctgcc cttcgcctgg ttcgtggcgc      180
cttgtgaccc cgggcccctg ccgcctgcaa gtcgaaattg cgctgtgctc ctgtgctacg      240
gcctgtggct ggactgcctg ctgctgccct actggctggc aagatcaagc tctccctggt      300
ggccgcgatc ctcgcggatc cgcgcccaag cttgggttag ctagccccta attccagcga      360
gaggcagagg gagcgagcgg gcggccggct agggtggaag agccgggcga gcagagctgc      420
gctgcgggcg tcctgggaag ggagatccgg agcgaatagg gggcttcgcc tctggcccag      480 ccctccccgct gatccccag ccagcggtcc gcaacccttg ccgcatccac gaaactttgc      540
ccatagcagc gggcgggcac tttgcactgg aacttacaac acccgagcaa ggacgcgact      600
ctcccgacgc ggggaggcta ttctgcccat ttggggacac ttccccgccg ctgccaggac      660
ccgcttctct gaaaggctct ccttgcagct gcttagacgc tggatttttt tcgggtagtg      720
gaaaaccagc agcctcccgc gccgctcgag cggaaaaggc cttttgctct agagcttggc      780
gcgccaa                                                               787

<210> SEQ ID NO 14
<211> LENGTH: 1225
<212> TYPE: DNA
<213> ORGANISM: Artificial
<220> FEATURE:
<223> OTHER INFORMATION: Synthetic

<400> SEQUENCE: 14
gtcgacgtcg gccataaatt ttttgcaaaa gccttggcct ccaaaaaagc ctcctcacta       60
cttctggaat agctcagagg ccgaggcggc ctcggcctct gcataaataa aaaaaattag      120
tcagccttgg ggcggagaaa ctatcgttgc tgactaattg agatcggagt actgtcctcc      180
gcgttacata acttacggta aatggcccgc ctggctgacc gcccaacgac ccccgcccat      240
tgacgtcaat aatgacgtat gttcccatag taacgccaat agggactttc cattgacgtc      300
aatgggtgga gtatttacgg taaactgccc acttggcagt acatcaagtg tatcatatgc      360
caagtacgcc ccctattgac gtcaatgacg gtaaatggcc cgcctggcat tatgcccagt      420
acatgacctt atgggacttt cctacttggc agtacatcta cgtattagtc atcgctatta      480
ccatggtgat gcggttttgg cagtacatca atgggcgtgg atagcggttt gactcacggg      540
gatttccaag tctccacccc attgacgtca atgggagttt gttttggcac caaaatcaac      600
gggactttcc aaaatgtcgt aacaactccg ccccattgac gcaaatgggc ggtaggcgtg      660
tacggtggga ggtctatata agcagagctc gtttagtgaa ccgtcagatc gcctggagac      720
gccatccacg ctgttttgac ctccatagaa gacaccggga ccgatccagc ctccgcggcc      780
gggaacggtg cattggaacg cggattcccc gtgccaagag tgacgtaagt accgcctata      840
gactctatag gcacacccct ttggctctta tccatcaatt aatacgactc actataggga      900
gacagactgt tccttttcctg ggtctttttct ggcttcgagg ggctcgcatc tctccttcac      960
gcgcccgccg ccctacctga ggccgccatc cacgccggtt gagtcgcgtt ctgccgcctc     1020
ccgcctgtgg tgcctcctga actgcgtccg ccgtctaggt aagtttaaag ctcaggtcga     1080
gaccgggcct ttgtccggcg ctcccttgga gcctacctag actcagccgg ctctccacgc     1140
tttgcctgac cctgcttgct caactctacg tctttgtttc gttttctgtt ctgcgccgtt     1200
acagatccaa gccaccccgg aattc                                          1225
```

```
<210> SEQ ID NO 15
<211> LENGTH: 1283
<212> TYPE: DNA
<213> ORGANISM: Artificial
<220> FEATURE:
<223> OTHER INFORMATION: Synthetic

<400> SEQUENCE: 15
tctagagcta gatgactaac gtttaaaccc gctgatcagc ctcgactgtg ccttctagtt      60
gccagccatc tgttgtttgc ccctcccccg tgccttcctt gaccctggaa ggtgccactc     120
ccactgtcct ttcctaataa aatgaggaaa ttgcatcgca ttgtctgagt aggtgtcatt     180
ctattctggg gggtggggtg gggcaggaca gcaaggggga ggattgggaa gacaatagca     240
ggcatgctgg ggatgcggtg ggctctatgg cggagtactg tcctccgctt cccacgtggc     300
ggagggactg gggacccggg cacccgtcct gcccttcac cttccagctc cgcctcctcc      360
gcgcggaccc cgccccgtcc cgaccctcc cgggtccccg gccagcccc ctccgggccc      420
tcccagcccc tccccttcct ttccgcggcc ccgccctc ctcgcggcgc gagttttgga     480
aagtccccag gctccccagc aggcagaagt atccaaagca tccatctcaa ttagtcagca     540
accaggtgtg gaaagtcccc aggctcccca gcaggcagaa gtatccaaag catccatctc     600
aattagtcag caaccatagt cccgcccta actccgccca tcccgcccct aactccgccc     660
agttccgccc attctccgcc ccatggctga ctaattttttt ttatttatgc agaggccgag     720
gccgcctctg cctctgagct attccagaag tagtgaggag gcttttttgg aggccaaggc     780
ttttgcaaaa agctccgtta cataacttac ggtaaatggc ccgcctggct gaccgcccaa     840
cgacccccgc ccattgacgt caataatgac gtatgttccc atagtaacgc caatagggac     900
tttccattga cgtcaatggg tggagtattt acggtaaact gcccacttgg cagtacatca     960
agtgtatcat atgccaagta cgccccctat tgacgtcaat gacggtaaat ggcccgcctg    1020
gcattatgcc cagtacatga ccttatggga ctttcctact tggcagtaca tctacgtatt    1080
agtcatcgct attaccatgg tgatgcggtt ttggcagtac atcaatgggc gtggatagcg    1140
gtttgactca cggggatttc caagtctcca ccccattgac gtcaatggga gtttgttttg    1200
gcaccaaaat caacgggact ttccaaaatg tcgtaacaac tccgccccat tgacgcaaat    1260
gggcggtagg cgtgttggcg cgc                                           1283

<210> SEQ ID NO 16
<211> LENGTH: 5280
<212> TYPE: DNA
<213> ORGANISM: Artificial
<220> FEATURE:
<223> OTHER INFORMATION: Synthetic

<400> SEQUENCE: 16
gggctgtgtg cacgaacccc ccgttcagcc cgaccgctgc gccttatccg gtaactatcg      60
tcttgagtcc aacccggtaa gacacgactt atcgccactg gcagcagcca ctggtaacag     120
gattagcaga gcgaggtatg taggcggtgc tacagagttc ttgaagtggt ggcctaacta     180
cggctacact agaagaacag tatttggtat ctgcgctctg ctgaagccag ttacctcgga     240
aaaagagttg gtagctcttg atccggcaaa caaaccaccg ctggtagcgg tggttttttt     300
gtttgcaagc agcagattac gcgcagaaaa aaaggatctc aagaagatcc tttgatttc     360
taccgaagaa aggcccaccc gtgaaggtga gccagtgagt tgattgcagt ccagttacgc     420
tggagtctga ggctcgtcct gaatgtgtaa aacgacggcc agtttatcta gtcagcttga    480
```

```
ttctagctga tcgtggaccg gaaggtgagc cagtgagttg attgcagtcc agttacgctg    540
gagtctgagg ctcgtcctga atgatatacg cgtcggaggg ttgcgtttga dacgggcgac    600
agatacgcgt cgacgtcggc cataaatttt ttgcaaaagc cttggcctcc aaaaaagcct    660
cctcactact tctggaatag ctcagaggcc gaggcggcct cggcctctgc ataaataaaa    720
aaaattagtc agccttgggg cggagaaact atcgttgctg actaattgag atcggagtac    780
tgtcctccgc gttacataac ttacggtaaa tggcccgcct ggctgaccgc ccaacgaccc    840
ccgcccattg acgtcaataa tgacgtatgt tcccatagta acgccaatag ggactttcca    900
ttgacgtcaa tgggtggagt atttacggta aactgcccac ttggcagtac atcaagtgta    960
tcatatgcca agtacgcccc ctattgacgt caatgacggt aaatggcccg cctggcatta   1020
tgcccagtac atgaccttat gggactttcc tacttggcag tacatctacg tattagtcat   1080
cgctattacc atggtgatgc ggttttggca gtacatcaat gggcgtggat agcggtttga   1140
ctcacgggga tttccaagtc tccaccccat tgacgtcaat gggagtttgt tttggcacca   1200
aaatcaacgg gactttccaa aatgtcgtaa caactccgcc ccattgacgc aaatgggcgg   1260
taggcgtgta cggtgggagg tctatataag cagagctcgt ttagtgaacc gtcagatcgc   1320
ctggagacgc catccacgct gttttgacct ccatagaaga caccgggacc gatccagcct   1380
ccgcggccgg gaacggtgca ttggaacgcg gattccccgt gccaagagtg acgtaagtac   1440
cgcctataga ctctataggc acaccccttt ggctcttatc catcaattaa tacgactcac   1500
tataggggaga cagactgttc ctttcctggg tcttttctgg cttcgagggg ctcgcatctc   1560
tccttcacgc gcccgccgcc ctacctgagg ccgccatcca cgccggttga gtcgcgttct   1620
gccgcctccc gcctgtggtg cctcctgaac tgcgtccgcc gtctaggtaa gtttaaagct   1680
caggtcgaga ccgggccttt gtccggcgct cccttggagc ctacctagac tcagccggct   1740
ctccacgctt tgcctgaccc tgcttgctca actctacgtc tttgtttcgt tttctgttct   1800
gcgccgttac agatccaagc caccccggaa ttccggggaa gatcttcccg ggtaccccg    1860
aggactagtt cgacgccggc caagacagca cagacagatt gacctattgg ggtgtttcgc   1920
gagtgtgaga gggaagcgcc gcggcctgta ttactagacc tgcccttcgc ctggttcgtg   1980
gcgccttgtg accccgggcc cctgccgcct gcaagtcgaa attgcgctgt gctcctgtgc   2040
tacgcctgt ggctggactg cctgctgctg ccctactggc tggcaagatc aagctctccc    2100
tggtggccgc gatcctcgcg gatccgcgcc caagcttggg ttagctagcc cctaattcca   2160
gcgagaggca gagggagcga gcgggcggcc ggctagggtg gaaagagccgg gcgagcagag   2220
ctgcgctgcg ggcgtcctgg gaaggagat ccggagcgaa taggggggctt cgcctctggc    2280
ccagcctcc cgctgatccc ccagccagcg gtccgcaacc cttgccgcat ccacgaaact    2340
tgcccatag cagcgggcgg gcactttgca ctggaactta caacacccga gcaaggacgc    2400
gactctcccg acgcggggag gctattctgc ccatttgggg acacttcccc gccgctgcca   2460
ggacccgctt ctctgaaagg ctctccttgc agctgcttag acgctggatt tttttcgggt   2520
agtggaaaac cagcagcctc ccgcgccgct cgagcggaaa aggccttttg ctctagagct   2580
agatgactaa cgtttaaacc cgctgatcag cctcgactgt gccttctagt tgccagccat   2640
ctgttgtttg cccctccccc gtgccttcct tgaccctgga aggtgccact cccactgtcc   2700
tttcctaata aaatgaggaa attgcatcgc attgtctgag taggtgtcat tctattctgg   2760
ggggtggggt gggggcaggac agcaagggg aggattggga agacaatagc aggcatgctg    2820
gggatgcggt gggctctatg gcggagtact gtcctccgct tcccacgtgg cggagggact   2880
```

```
ggggacccgg gcacccgtcc tgcccsttca ccttccagct ccgcctcctc cgcgcggacc    2940
ccgcccsgtc ccgacccctc ccgggtcccc ggcccagccc cctccgggcc ctcccagccc    3000
ctcccsttcc tttccgcggc cccgccctct cctcgcggcg cgagttttgg aaagtcccca    3060
ggctccccag caggcagaag tatccaaagc atccatctca attagtcagc aaccaggtgt    3120
ggaaagtccc caggctcccc agcaggcaga agtatccaaa gcatccatct caattagtca    3180
gcaaccatag tcccgcccct aactccgccc atcccgcccc taactccgcc cagttccgcc    3240
cattctccgc cccatggctg actaattttt tttatttatg cagaggccga ggccgcctct    3300
gcctctgagc tattccagaa gtagtgagga ggctttttg gaggcaagg cttttgcaaa    3360 aagctccgtt acataactta cggtaaatgg cccgcctggc tgaccgccca acgaccccg    3420 cccattgacg tcaataatga cgtatgttcc catagtaacg ccaatagggact tttccattg    3480 acgtcaatgg gtggagtatt tacggtaaac tgcccacttg gcagtacatc aagtgtatca    3540
tatgccaagt acgccccta ttgacgtcaa tgacggtaaa tggcccgcct ggcattatgc    3600
ccagtacatg accttatggg actttcctac ttggcagtac atctacgtat tagtcatcgc    3660
tattaccatg gtgatgcggt tttggcagta catcaatggg cgtggatagc ggtttgactc    3720
acggggattt ccaagtctcc accccattga cgtcaatggg agtttgtttt ggcaccaaaa    3780
tcaacgggac tttccaaaat gtcgtaacaa ctccgccca ttgacgcaaa tgggcggtag    3840
gcgtgttggc gcgccaaatc agttctggac gagcgagctg tcgtccggcg ccgcgatct    3900 tacggcatta tacgtatgat cggtccacga tcagctagat tatctagtca gcttgatgtc    3960
atagctgttt cctgaggctc aatactgacc atttaaatca tacctgacct ccatagcaga    4020
aagtcaaaag cctccgaccg gaggcttttg acttgatcgg cacgtaagag gttccaactt    4080
tcaccataat gaaataagat cactaccggg cgtatttttt gagttatcga ttttcagg    4140 agctaaggaa gctaaaatga gccatattca acgggaaacg tcttgcttga agccgcgatt    4200
aaattccaac atggatgctg atttatatgg gtataaatgg gctcgcgata atgtcgggca    4260
atcaggtgcg acaatctatc gattgtatgg gaagcccgat gcgccagagt tgtttctgaa    4320
acatggcaaa ggtagcgttg ccaatgatgt tacagatgag atggtcaggc taaactggct    4380
gacggaattt atgcctcttc cgaccatcaa gcattttatc cgtactcctg atgatgcatg    4440
gttactcacc actgcgatcc cagggaaaac agcattccag gtattagaag aatatcctga    4500
ttcaggtgaa atattgttg atgcgctggc agtgttcctg cgccggttgc attcgattcc    4560
tgtttgtaat tgtccttta acggcgatcg cgtatttcgt ctcgctcagg cgcaatcacg    4620
aatgaataac ggtttggttg gtgcgagtga ttttgatgac gagcgtaatg gctggcctgt    4680
tgaacaagtc tggaaagaaa tgcataaact cttgccattc tcaccggatt cagtcgtcac    4740
tcatggtgat ttctcacttg ataaccttat ttttgacgag gggaaattaa taggttgtat    4800
tgatgttgga cgagtcggaa tcgcagaccg ataccaggat cttgccatcc tatggaactg    4860
cctcggtgag ttttctcctt cattacagaa acggcttttt caaaaatatg gtattgataa    4920
tcctgatatg aataaattgc agtttcactt gatgctcgat gagttttct aatgaggacc    4980 taaatgtaat cacctggctc accttcgggt gggcctttct gcgttgctgg cgttttccca    5040
taggctccgc cccctgacg agcatcacaa aaatcgatgc tcaagtcaga ggtggcgaaa    5100
cccgacagga ctataaagat accaggcgtt tccccctgga agctccctcg tgcgctctcc    5160
tgttccgacc ctgccgctta ccggatacct gtccgccttt ctcccttcgg gaagcgtggc    5220
```

```
gctttctcat agctcacgct gtaggtatct cagttcggtg taggtcgttc gctccaagct    5280
```

<210> SEQ ID NO 17
<211> LENGTH: 1053
<212> TYPE: DNA
<213> ORGANISM: Homo sapiens

<400> SEQUENCE: 17

```
atgcagcggc ttggggccac cctgctgtgc ctgctactgg cggcggcggt ccccacggcc      60
cccgcgcccg ctccgacggc gacctcggct ccagtcaagc ccggcccggc tctcagctac     120
ccgcaggagg aggccaccct caatgagatg ttccgcgagg ttgaggaact ggtggaggac     180
acgcagcaca aattgcgcag cgcggtggaa gagatggagg cagaagaagc tgctgctaaa     240
gcatcatcag aagtgaacct ggcaaactta cctcccagct atcacaatga gaccaacaca     300
gacacgaagg ttggaaataa taccatccat gtgcaccgag aaattcacaa gataaccaac     360
aaccaggctc gacaaatggt cttttcagag acagttatca catctgtggg agacgaagaa     420
ggcagaagga gccacgagtg catcatcgac gaggactgtg gcccagcat gtactgccag     480
tttgccagct ccagtacac ctgccagcca tgccggggcc agaggatgct ctgcaccgg      540
gacagtgagt gctgtggaga ccagctgtgt gtctggggtc actgccacca aatggccacc     600
aggggcagca atgggaccat ctgtgacaac cagagggact gccagccggg gctgtgctgt     660
gccttccaga gaggcctgct gttccctgtg tgcataccc tgcccgtgga gggcgagctt     720
tgccatgacc ccgccagccg gcttctggac ctcatcacct gggagctaga gcctgatgga     780
gccttggacc gatgcccttg tgccagtggc tcctctgcc agcccacag ccacagcctg      840
gtgtatgtgt gcaagccgac cttcgtgggg agccgtgacc aagatgggga gatcctgctg     900
cccagagagg tccccgatga gtatgaagtt ggcagcttca tggaggaggt gcgccaggag     960
ctggaggacc tggagaggag cctgactgaa gagatggcgc tggggagcc tgcggctgcc     1020
gccgctgcac tgctgggagg ggaagagatt tag                                  1053
```

<210> SEQ ID NO 18
<211> LENGTH: 350
<212> TYPE: PRT
<213> ORGANISM: Homo sapiens

<400> SEQUENCE: 18

```
Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Val Glu Asp Thr Gln His Lys
    50                  55                  60

Leu Arg Ser Ala Val Glu Glu Met Glu Ala Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
        115                 120                 125

Ser Glu Thr Val Ile Thr Ser Val Gly Asp Glu Glu Gly Arg Arg Ser
```

|     |     |     |     |     |     |     |     |     |     |     |     |     |     |
| --- | --- | --- | --- | --- | --- | --- | --- | --- | --- | --- | --- | --- | --- |
|     |     |     | 130 |     |     |     | 135 |     |     |     | 140 |     |     |
| His | Glu | Cys | Ile | Ile | Asp | Glu | Asp | Cys | Gly | Pro | Ser | Met | Tyr | Cys | Gln |
| 145 |     |     |     |     | 150 |     |     |     |     | 155 |     |     |     |     | 160 |
| Phe | Ala | Ser | Phe | Gln | Tyr | Thr | Cys | Gln | Pro | Cys | Arg | Gly | Gln | Arg | Met |
|     |     |     |     | 165 |     |     |     |     | 170 |     |     |     |     | 175 |     |
| Leu | Cys | Thr | Arg | Asp | Ser | Glu | Cys | Cys | Gly | Asp | Gln | Leu | Cys | Val | Trp |
|     |     |     | 180 |     |     |     |     | 185 |     |     |     |     | 190 |     |     |
| Gly | His | Cys | Thr | Lys | Met | Ala | Thr | Arg | Gly | Ser | Asn | Gly | Thr | Ile | Cys |
|     |     | 195 |     |     |     |     | 200 |     |     |     |     | 205 |     |     |     |
| Asp | Asn | Gln | Arg | Asp | Cys | Gln | Pro | Gly | Leu | Cys | Cys | Ala | Phe | Gln | Arg |
|     | 210 |     |     |     |     | 215 |     |     |     |     | 220 |     |     |     |     |
| Gly | Leu | Leu | Phe | Pro | Val | Cys | Ile | Pro | Leu | Pro | Val | Glu | Gly | Glu | Leu |
| 225 |     |     |     |     | 230 |     |     |     |     | 235 |     |     |     |     | 240 |
| Cys | His | Asp | Pro | Ala | Ser | Arg | Leu | Leu | Asp | Leu | Ile | Thr | Trp | Glu | Leu |
|     |     |     |     | 245 |     |     |     |     | 250 |     |     |     |     | 255 |     |
| Glu | Pro | Asp | Gly | Ala | Leu | Asp | Arg | Cys | Pro | Cys | Ala | Ser | Gly | Leu | Leu |
|     |     |     | 260 |     |     |     |     | 265 |     |     |     |     | 270 |     |     |
| Cys | Gln | Pro | His | Ser | His | Ser | Leu | Val | Tyr | Val | Cys | Lys | Pro | Thr | Phe |
|     |     | 275 |     |     |     |     | 280 |     |     |     |     | 285 |     |     |     |
| Val | Gly | Ser | Arg | Asp | Gln | Asp | Gly | Glu | Ile | Leu | Leu | Pro | Arg | Glu | Val |
|     | 290 |     |     |     |     | 295 |     |     |     |     | 300 |     |     |     |     |
| Pro | Asp | Glu | Tyr | Glu | Val | Gly | Ser | Phe | Met | Glu | Glu | Val | Arg | Gln | Glu |
| 305 |     |     |     |     | 310 |     |     |     |     | 315 |     |     |     |     | 320 |
| Leu | Glu | Asp | Leu | Glu | Arg | Ser | Leu | Thr | Glu | Glu | Met | Ala | Leu | Gly | Glu |
|     |     |     |     | 325 |     |     |     |     | 330 |     |     |     |     | 335 |     |
| Pro | Ala | Ala | Ala | Ala | Ala | Leu | Leu | Gly | Gly | Glu | Glu | Ile |
|     |     |     | 340 |     |     |     |     | 345 |     |     |     |     | 350 |

<210> SEQ ID NO 19
<211> LENGTH: 1072
<212> TYPE: DNA
<213> ORGANISM: Artificial
<220> FEATURE:
<223> OTHER INFORMATION: Synthetic

<400> SEQUENCE: 19

```
acgcgtcgac gtcggccata aattttttgc aaaagccttg gcctccaaaa aagcctcctc      60
actacttctg gaatagctca gaggccgagg cggcctcggc ctctgcataa ataaaaaaaa     120
ttagtcagcc ttggggcgga gaaactatcg ttgctgacta attgagatcg gagtactgtc     180
ctccgtggaa agtccccagg ctccccagca ggcagaagta tgcaaagcat gcatctcaat     240
tagtcagcaa ccaggtgtgg aaagtcccca ggctccccag caggcagaag tatgcaaagc     300
atgcatctca attagtcagc aaccatagtc ccgcccctaa ctccgcccat ccgccccta      360
actccgccca gttccgccca ttctccgccc catggctgac taattttttt tatttatgca     420
gaggccgagg ccgcctctgc ctctgagcta ttccagaagt agtgaggagg ctttttggga    480
ggcctaggct tttgcaaaaa gctctacggt gggaggtcta taagcaga gctcgtttag     540
tgaaccgtca gatcgcctgg agacgccatc cacgctgttt tgacctccat agaagacacc    600
gggaccgatc cagcctccgc ggccgggaac ggtgcattgg aacgcggatt ccccgtgcca    660
agagtgacgt aagtaccgcc tatagactct ataggcacac ccctttggct cttatccatc    720
aattaatacg actcactata gggagacaga ctgttccttt cctgggtctt ttctggcttc    780
gaggggctcg catctctcct tcacgcgccc gccgccctac ctgaggccgc catccacgcc    840
```

| | |
|---|---|
| ggttgagtcg cgttctgccg cctcccgcct gtggtgcctc ctgaactgcg tccgccgtct | 900 |
| aggtaagttt aaagctcagg tcgagaccgg gcctttgtcc ggcgctccct tggagcctac | 960 |
| ctagactcag ccggctctcc acgctttgcc tgaccctgct tgctcaactc tacgtctttg | 1020 |
| tttcgttttc tgttctgcgc cgttacagat ccaagccacc ccggaattcc gg | 1072 |

```
<210> SEQ ID NO 20
<211> LENGTH: 942
<212> TYPE: DNA
<213> ORGANISM: Artificial
<220> FEATURE:
<223> OTHER INFORMATION: Synthetic

<400> SEQUENCE: 20
```

| | |
|---|---|
| acgcgtcgac gtcggccata aattttttgc aaaagccttg gcctccaaaa aagcctcctc | 60 |
| actacttctg gaatagctca gaggccgagg cggcctcggc tctgcataa ataaaaaaaa | 120 |
| ttagtcagcc ttggggcgga gaaactatcg ttgctgacta attgagatcg gagtactgtc | 180 |
| ctccgcttcc cacgtggcgg agggactggg gaccccggga cccgtcctgc cccttcacct | 240 |
| tccagctccg cctcctccgc gcggaccccg cccgtcccg accctcccg ggtccccggc | 300 |
| ccagcccct ccgggccctc ccagccctc cccttcctt ccgcggcccc gcctctcct | 360 |
| cgcggcgcga gttttacggt gggaggtcta tataagcaga gctcgtttag tgaaccgtca | 420 |
| gatcgcctgg agacgccatc cacgctgttt tgacctccat agaagacacc gggaccgatc | 480 |
| cagcctccgc ggccgggaac ggtgcattgg aacgcggatt ccccgtgcca agagtgacgt | 540 |
| aagtaccgcc tatagactct ataggcacac ccctttggct cttatccatc aattaatacg | 600 |
| actcactata gggagacaga ctgttccttt cctgggtctt ttctggcttc gaggggctcg | 660 |
| catctctcct tcacgcgccc gccgcccctac ctgaggccgc catccacgcc ggttgagtcg | 720 |
| cgttctgccg cctcccgcct gtggtgcctc ctgaactgcg tccgccgtct aggtaagttt | 780 |
| aaagctcagg tcgagaccgg gcctttgtcc ggcgctccct tggagcctac ctagactcag | 840 |
| ccggctctcc acgctttgcc tgaccctgct tgctcaactc tacgtctttg tttcgttttc | 900 |
| tgttctgcgc cgttacagat ccaagccacc ccggaattcc gg | 942 |

```
<210> SEQ ID NO 21
<211> LENGTH: 747
<212> TYPE: DNA
<213> ORGANISM: Artificial
<220> FEATURE:
<223> OTHER INFORMATION: Synthetic

<400> SEQUENCE: 21
```

| | |
|---|---|
| ccggaattcc ggaccatggt gagcaagggc gaggagctgt tcaccggggt ggtgcccatc | 60 |
| ctggtcgagc tggacggcga cgtaaacggc cacaagttca gcgtgtccgg cgagggcgag | 120 |
| ggcgatgcca cctacggcaa gctgaccctg aagttcatct gcaccaccgg caagctgccc | 180 |
| gtgccctggc ccaccctcgt gaccaccctg acctacggcg tgcagtgctt cagccgctac | 240 |
| cccgaccaca tgaagcagca cgacttcttc aagtccgcca tgcccgaagg ctacgtccag | 300 |
| gagcgcacca tcttcttcaa ggacgacggc aactacaaga cccgcgccga ggtgaagttc | 360 |
| gagggcgaca ccctggtgaa ccgcatcgag ctgaagggca tcgacttcaa ggaggacggc | 420 |
| aacatcctgg ggcacaagct ggagtacaac tacaacagcc acaacgtcta tatcatggcc | 480 |
| gacaagcaga agaacggcat caaggtgaac ttcaagatcc gccacaacat cgaggacggc | 540 |
| agcgtgcagc tcgccgacca ctaccagcag aacaccccca tcggcgacgg ccccgtgctg | 600 |

| | |
|---|---|
| ctgcccgaca accactacct gagcacccag tccgccctga gcaaagaccc caacgagaag | 660 |
| cgcgatcaca tggtcctgct ggagttcgtg accgccgccg ggatcactct cggcatggac | 720 |
| gagctgtaca agtgacgcgg atccgcg | 747 |

<210> SEQ ID NO 22
<211> LENGTH: 3696
<212> TYPE: DNA
<213> ORGANISM: Artificial
<220> FEATURE:
<223> OTHER INFORMATION: Synthetic

<400> SEQUENCE: 22

| | |
|---|---|
| acgcgtcgac gtcggccata aattttttgc aaaagccttg gcctccaaaa aagcctcctc | 60 |
| actacttctg gaatagctca gaggccgagg cggcctcggc ctctgcataa ataaaaaaaa | 120 |
| ttagtcagcc ttgggcggga gaaactatcg ttgctgacta attgagatcg gagtactgtc | 180 |
| ctccgcgtta cataacttac ggtaaatggc ccgcctggct gaccgcccaa cgaccccgc | 240 |
| ccattgacgt caataatgac gtatgttccc atagtaacgc caatagggac tttccattga | 300 |
| cgtcaatggg tggagtattt acggtaaact gcccacttgg cagtacatca agtgtatcat | 360 |
| atgccaagta cgccccctat tgacgtcaat gacggtaaat ggcccgcctg gcattatgcc | 420 |
| cagtacatga cctatgggga ctttcctact tggcagtaca tctacgtatt agtcatcgct | 480 |
| attaccatgg tgatgcggtt ttggcagtac atcaatgggc gtggatagcg gtttgactca | 540 |
| cggggatttc caagtctcca ccccattgac gtcaatggga gtttgttttg gcaccaaaat | 600 |
| caacgggact ttccaaaatg tcgtaacaac tccgccccat tgacgcaaat gggcggtagg | 660 |
| cgtgtacggt gggaggtcta tataagcaga gctcgtttag tgaaccgtca gatcgcctgg | 720 |
| agacgccatc cacgctgttt tgacctccat agaagacacc gggaccgatc cagcctccgc | 780 |
| ggccgggaac ggtgcattgg aacgcggatt ccccgtgcca agagtgacgt aagtaccgcc | 840 |
| tatagactct ataggcacac ccctttggct cttatccatc aattaatacg actcactata | 900 |
| gggagacaga ctgttccttt cctgggtctt ttctggcttc gagggctcg catctctcct | 960 |
| tcacgcgccc gccgccctac ctgaggccgc catccacgcc ggttgagtcg cgttctgccg | 1020 |
| cctcccgcct gtggtgcctc ctgaactgcg tccgccgtct aggtaagttt aaagctcagg | 1080 |
| tcgagaccgg gcctttgtcc ggcgctccct tggagcctac ctagactcag ccggctctcc | 1140 |
| acgctttgcc tgaccctgct tgctcaactc tacgtctttg tttcgttttc tgttctgcgc | 1200 |
| cgttacagat ccaagccacc ccggaattcc ggaccatggt gagcaagggc gaggagctgt | 1260 |
| tcaccggggt ggtgcccatc ctggtcgagc tggacggcga cgtaaacggc cacaagttca | 1320 |
| gcgtgtccgg cgagggcgag ggcgatgcca cctacgcaa gctgaccctg aagttcatct | 1380 |
| gcaccaccgg caagctgccc gtgccctggc ccaccctcgt gaccaccctg acctacggcg | 1440 |
| tgcagtgctt cagccgctac cccgaccaca tgaagcagca cgacttcttc aagtccgcca | 1500 |
| tgcccgaagg ctacgtccag gagcgcacca tcttcttcaa ggacgacggc aactacaaga | 1560 |
| cccgcgccga ggtgaagttc gagggcgaca ccctggtgaa ccgcatcgag ctgaagggca | 1620 |
| tcgacttcaa ggaggacggc aacatcctgg ggcacaagct ggagtacaac tacaacagcc | 1680 |
| acaacgtcta tatcatggcc gacaagcaga agaacggcat caaggtgaac ttcaagatcc | 1740 |
| gccacaacat cgaggacggc agcgtgcagc tcgccgacca ctaccagcag aacacccca | 1800 |
| tcggcgacgg ccccgtgctg ctgcccgaca accactacct gagcacccag tccgccctga | 1860 |

```
gcaaagaccc caacgagaag cgcgatcaca tggtcctgct ggagttcgtg accgccgccg    1920
ggatcactct cggcatggac gagctgtaca agtgacgcgg atccgcgccc aagcttgggt    1980
tagctagccc ctaattccag cgagaggcag agggagcgag cgggcggccg gctagggtgg    2040
aagagccggg cgagcagagc tgcgctgcgg cgtcctggg aagggagatc cggagcgaat     2100
agggggcttc gcctctggcc cagccctccc gctgatcccc cagccagcgg tccgcaaccc    2160
ttgccgcatc cacgaaactt tgcccatagc agcgggcggg cactttgcac tggaacttac    2220
aacacccgag caaggacgcg actctcccga cgcggggagg ctattctgcc catttgggga    2280
cacttccccg ccgctgccag gacccgcttc tctgaaaggc tctccttgca gctgcttaga    2340
cgctggattt ttttcgggta gtggaaaacc agcagcctcc cgcgccgctc gagcggaaaa    2400
ggccttttgc tctagagcta gatgactaac gtttaaaccc gctgatcagc ctcgactgtg    2460
ccttctagtt gccagccatc tgttgtttgc cctcccccg tgccttcctt gaccctggaa      2520
ggtgccactc ccactgtcct ttcctaataa aatgaggaaa ttgcatcgca ttgtctgagt    2580
aggtgtcatt ctattctggg gggtggggtg ggcaggaca gcaaggggga ggattgggaa      2640
gacaatagca ggcatgctgg ggatgcggtg ggctctatgg cggagtactg tcctccgctt    2700
cccacgtggc ggagggactg gggacccggg cacccgtcct gcccccttcac cttccagctc    2760 cgcctcctcc gcgcggaccc cgccccgtcc cgaccccctcc cgggtccccg gcccagcccc    2820
ctccgggccc tcccagcccc tcccttcct ttccgcggcc ccgccctctc ctcgcggcgc      2880
gagttttgga aagtccccag gctccccagc aggcagaagt atccaaagca tccatctcaa    2940
ttagtcagca accaggtgtg gaaagtcccc aggctcccca gcaggcagaa gtatccaaag    3000
catccatctc aattagtcag caaccatagt cccgccccta actccgccca tcccgcccct    3060
aactccgccc agttccgccc attccgccc ccatggctga ctaattttttt ttatttatgc    3120 agaggccgag gccgcctctg cctctgagct attccagaag tagtgaggag gcttttttgg    3180
aggccaaggc ttttgcaaaa agctccgtta cataacttac ggtaaatggc ccgcctggct    3240
gaccgcccaa cgacccccgc ccattgacgt caataatgac gtatgttccc atagtaacgc    3300
caatagggac tttccattga cgtcaatggg tggagtattt acggtaaact gcccacttgg    3360
cagtacatca agtgtatcat atgccaagta cgccccctat tgacgtcaat gacggtaaat    3420
ggcccgcctg gcattatgcc cagtacatga ccttatggga ctttcctact tggcagtaca    3480
tctacgtatt agtcatcgct attaccatgg tgatgcggtt ttggcagtac atcaatgggc    3540
gtggatagcg gtttgactca cggggatttc caagtctcca ccccattgac gtcaatggga    3600
gtttgttttg gcaccaaaat caacgggact ttccaaaatg tcgtaacaac tccgccccat    3660
tgacgcaaat gggcggtagg cgtgttggcg cgccaa                              3696
```

<210> SEQ ID NO 23
<211> LENGTH: 3536
<212> TYPE: DNA
<213> ORGANISM: Artificial
<220> FEATURE:
<223> OTHER INFORMATION: Synthetic

<400> SEQUENCE: 23

```
acgcgtcgac gtcggccata aatttttgc aaaagccttg gcctccaaaa aagcctcctc     60
actacttctg gaatagctca gaggccgagg cggcctcggc ctctgcataa ataaaaaaaa    120
ttagtcagcc ttgggcgga gaaactatcg ttgctgacta attgagatcg gagtactgtc     180
ctccgtggaa agtccccagg ctccccagca ggcagaagta tgcaaagcat gcatctcaat    240
```

```
tagtcagcaa ccaggtgtgg aaagtcccca ggctccccag caggcagaag tatgcaaagc    300
atgcatctca attagtcagc aaccatagtc ccgcccctaa ctccgcccat cccgcccta     360 actccgccca gttccgccca ttctccgccc catggctgac taattttttt tatttatgca    420
gaggccgagg ccgcctctgc ctctgagcta ttccagaagt agtgaggagg ctttttttgga   480 ggcctaggct tttgcaaaaa gctctacggt gggaggtcta tataagcaga gctcgtttag    540
tgaaccgtca gatcgcctgg agacgccatc cacgctgttt tgacctccat agaagacacc    600
gggaccgatc cagcctccgc ggccgggaac ggtgcattgg aacgcggatt ccccgtgcca    660
agagtgacgt aagtaccgcc tatagactct ataggcacac ccctttggct cttatccatc    720
aattaatacg actcactata gggagacaga ctgttccttt cctgggtctt ttctggcttc    780
gaggggctcg catctctcct tcacgcgccc gccgccctac ctgaggccgc catccacgcc    840
ggttgagtcg cgttctgccg cctcccgcct gtggtgcctc ctgaactgcg tccgccgtct    900
aggtaagttt aaagctcagg tcgagaccgg gcctttgtcc ggcgctccct tggagcctac    960
ctagactcag ccggctctcc acgctttgcc tgaccctgct tgctcaactc tacgtctttg   1020
tttcgttttc tgttctgcgc cgttacagat ccaagccacc ccggaattcc ggaccatggt   1080
gagcaagggc gaggagctgt tcaccggggt ggtgcccatc ctggtcgagc tggacggcga   1140
cgtaaacggc cacaagttca gcgtgtccgg cgagggcgag ggcgatgcca cctacggcaa   1200
gctgaccctg aagttcatct gcaccaccgg caagctgccc gtgccctggc ccaccctcgt   1260
gaccaccctg acctacggcg tgcagtgctt cagccgctac cccgaccaca tgaagcagca   1320
cgacttcttc aagtccgcca tgcccgaagg ctacgtccag gagcgcacca tcttcttcaa   1380
ggacgacggc aactacaaga cccgcgccga ggtgaagttc gagggcgaca ccctggtgaa   1440
ccgcatcgag ctgaagggca tcgacttcaa ggaggacggc aacatcctgg ggcacaagct   1500
ggagtacaac tacaacagcc acaacgtcta tatcatggcc gacaagcaga agaacggcat   1560
caaggtgaac ttcaagatcc gccacaacat cgaggacggc agcgtgcagc tcgccgacca   1620
ctaccagcag aacaccccca tcggcgacgg ccccgtgctg ctgcccgaca accactacct   1680
gagcacccag tccgccctga gcaaagaccc caacgagaag cgcgatcaca tggtcctgct   1740
ggagttcgtg accgccgccg ggatcactct cggcatggac gagctgtaca agtgacgcgg   1800
atccgcgccc aagcttgggt tagctagccc ctaattccag cgagaggcag agggagcgag   1860
cgggcggccg gctagggtgg aagagccggg cgagcagagc tgcgctgcgg gcgtcctggg   1920
aagggagatc cggagcgaat aggggggctt gcctctggcc cagccctccc gctgatcccc   1980
cagccagcgg tccgcaaccc ttgccgcatc cacgaaactt gcccatagc agcgggcggg   2040 cactttgcac tggaacttac aacacccgag caaggacgcg actctcccga cgcggggagg   2100
ctattctgcc catttgggga cacttccccg ccgctgccag gacccgcttc tctgaaaggc   2160
tctccttgca gctgcttaga cgctggattt ttttcgggta gtggaaaacc agcagcctcc   2220
cgcgccgctc gagcggaaaa ggccttttgc tctagagcta gatgactaac gtttaaaccc   2280
gctgatcagc ctcgactgtg ccttctagtt gccagccatc tgttgtttgc cctcccccg    2340 tgccttcctt gaccctggaa ggtgccactc ccactgtcct ttcctaataa aatgaggaaa   2400
ttgcatcgca ttgtctgagt aggtgtcatt ctattctggg gggtggggtg ggcaggaca    2460 gcaaggggga ggattgggaa gacaatagca ggcatgctgg ggatgcggtg ggctctatgg   2520
cggagtactg tcctccgctt cccacgtggc ggagggactg gggacccggg cacccgtcct   2580
```

-continued

| | |
|---|---|
| gcccctccac cttccagctc cgcctcctcc gcgcggaccc cgccccgtcc cgacccctcc | 2640 |
| cgggtcccg gcccagcccc ctccgggccc tcccagcccc tccccttcct ttccgcggcc | 2700 |
| ccgccctctc ctcgcggcgc gagttttgga aagtcccag gctcccagc aggcagaagt | 2760 |
| atccaaagca tccatctcaa ttagtcagca accaggtgtg gaaagtcccc aggctcccca | 2820 |
| gcaggcagaa gtatccaaag catccatctc aattagtcag caaccatagt cccgcccta | 2880 |
| actccgccca tcccgcccct aactccgccc agttccgccc attctccgcc ccatggctga | 2940 |
| ctaatttttt ttatttatgc agaggccgag gccgcctctg cctctgagct attccagaag | 3000 |
| tagtgaggag gctttttgg aggccaaggc ttttgcaaaa agctccgtta cataacttac | 3060 |
| ggtaaatggc ccgcctggct gaccgcccaa cgaccccgc ccattgacgt caataatgac | 3120 |
| gtatgttccc atagtaacgc caatagggac tttccattga cgtcaatggg tggagtattt | 3180 |
| acggtaaact gcccacttgg cagtacatca agtgtatcat atgccaagta cgcccctat | 3240 |
| tgacgtcaat gacggtaaat ggcccgcctg gcattatgcc cagtacatga ccttatggga | 3300 |
| cttctctact tggcagtaca tctacgtatt agtcatcgct attaccatgg tgatgcggtt | 3360 |
| ttggcagtac atcaatgggc gtggatagcg gtttgactca cggggatttc caagtctcca | 3420 |
| ccccattgac gtcaatggga gtttgttttg gcaccaaaat caacgggact ttccaaaatg | 3480 |
| tcgtaacaac tccgccccat tgacgcaaat gggcggtagg cgtgttggcg cgccaa | 3536 |

<210> SEQ ID NO 24  
<211> LENGTH: 3406  
<212> TYPE: DNA  
<213> ORGANISM: Artificial  
<220> FEATURE:  
<223> OTHER INFORMATION: Synthetic

<400> SEQUENCE: 24

| | |
|---|---|
| acgcgtcgac gtcggccata aatttttgc aaaagccttg gcctccaaaa aagcctcctc | 60 |
| actacttctg gaatagctca gaggccgagg cggcctcggc ctctgcataa ataaaaaaaa | 120 |
| ttagtcagcc ttgggcgga gaaactatcg ttgctgacta attgagatcg gagtactgtc | 180 |
| ctccgcttcc cacgtggcgg agggactggg gacccgggca cccgtcctgc cccttcacct | 240 |
| tccagctccg cctcctccgc gcggaccccg ccccgtcccg accctcccg ggtccccggc | 300 |
| ccagcccccct ccgggccctc ccagcccctc cccttccttt ccgcggcccc gccctctcct | 360 |
| cgcggcgcga gttttacggt gggaggtcta tataagcaga gctcgtttag tgaaccgtca | 420 |
| gatcgcctgg agacgccatc cacgctgttt tgacctccat agaagacacc gggaccgatc | 480 |
| cagcctccgc ggccgggaac ggtgcattgg aacgcggatt ccccgtgcca agagtgacgt | 540 |
| aagtaccgcc tatagactct ataggcacac ccctttggct cttatccatc aattaatacg | 600 |
| actcactata gggagacaga ctgttccttt cctgggtctt ttctggcttc gaggggctcg | 660 |
| catctctcct tcacgcgccc gccgcccac ctgaggccgc catccacgcc ggttgagtcg | 720 |
| cgttctgccg cctcccgcct gtggtgcctc ctgaactgcg tccgccgtct aggtaagttt | 780 |
| aaagctcagg tcgagaccgg gcctttgtcc ggcgctccct ggagcctac ctagactcag | 840 |
| ccggctctcc acgctttgcc tgaccctgct tgctcaactc tacgtctttg tttcgttttc | 900 |
| tgttctgcgc cgttacagat ccaagccacc ccggaattcc ggaccatggt gagcaagggc | 960 |
| gaggagctgt tcaccggggt ggtgcccatc ctggtcgagc tggacggcga cgtaaacggc | 1020 |
| cacaagttca gcgtgtccgg cgagggcgag ggcgatgcca cctacggcaa gctgaccctg | 1080 |
| aagttcatct gcaccaccgg caagctgccc gtgccctggc ccaccctcgt gaccaccctg | 1140 |

```
acctacggcg tgcagtgctt cagccgctac cccgaccaca tgaagcagca cgacttcttc    1200
aagtccgcca tgcccgaagg ctacgtccag gagcgcacca tcttcttcaa ggacgacggc    1260
aactacaaga cccgcgccga ggtgaagttc gagggcgaca ccctggtgaa ccgcatcgag    1320
ctgaagggca tcgacttcaa ggaggacggc aacatcctgg ggcacaagct ggagtacaac    1380
tacaacagcc acaacgtcta tatcatggcc gacaagcaga agaacggcat caaggtgaac    1440
ttcaagatcc gccacaacat cgaggacggc agcgtgcagc tcgccgacca ctaccagcag    1500
aacaccccca tcggcgacgg ccccgtgctg ctgcccgaca accactacct gagcacccag    1560
tccgccctga gcaaagaccc caacgagaag cgcgatcaca tggtcctgct ggagttcgtg    1620
accgccgccg ggatcactct cggcatggac gagctgtaca agtgacgcgg atccgcgccc    1680
aagcttgggt tagctagccc ctaattccag cgagaggcag agggagcgag cgggcggccg    1740
gctagggtgg aagagccggg cgagcagagc tgcgctgcgg gcgtcctggg aagggagatc    1800
cggagcgaat aggggggcttc gcctctggcc cagccctccc gctgatcccc cagccagcgg    1860
tccgcaaccc ttgccgcatc cacgaaactt tgcccatagc agcgggcggg cactttgcac    1920
tggaacttac aacacccgag caaggacgcg actctcccga cgcggggagg ctattctgcc    1980
catttgggga cacttccccg ccgctgccag gacccgcttc tctgaaaggc tctccttgca    2040
gctgcttaga cgctggatttt ttttcgggta gtggaaaacc agcagcctcc cgcgccgctc    2100
gagcggaaaa ggccttttgc tctagagcta gatgactaac gtttaaaccc gctgatcagc    2160
ctcgactgtg ccttctagtt gccagccatc tgttgtttgc cctcccccg tgccttcctt    2220 gaccctggaa ggtgccactc ccactgtcct ttcctaataa aatgaggaaa ttgcatcgca    2280
ttgtctgagt aggtgtcatt ctattctggg gggtggggtg gggcaggaca gcaaggggga    2340
ggattgggaa gacaatagca ggcatgctgg ggatgcggtg ggctctatgg cggagtactg    2400
tcctccgctt cccacgtggc ggagggactg gggacccggg cacccgtcct gcccttcac    2460 cttccagctc cgcctcctcc gcgcggaccc cgccccgtcc cgacccctcc cgggtccccg    2520
gcccagcccc ctccgggccc tcccagcccc tcccctccct ttccgcggcc ccgccctctc    2580
ctcgcggcgc gagttttgga aagtccccag gctccccagc aggcagaagt atccaaagca    2640
tccatctcaa ttagtcagca accaggtgtg gaaagtcccc aggctcccca gcaggcagaa    2700
gtatccaaag catccatctc aattagtcag caaccatagt cccgcccta actccgccca    2760 tcccgcccct aactccgccc agttccgccc attctccgcc ccatggctga ctaattttt    2820 ttatttatgc agaggccgag gccgcctctg cctctgagct attccagaag tagtgaggag    2880
gcttttttgg aggccaaggc ttttgcaaaa agctccgtta cataacttac ggtaaatggc    2940
ccgcctggct gaccgcccaa cgaccccgc ccattgacgt caataatgac gtatgttccc    3000
atagtaacgc caatagggac tttccattga cgtcaatggg tggagtattt acggtaaact    3060
gcccacttgg cagtacatca agtgtatcat atgccaagta cgccccctat tgacgtcaat    3120
gacggtaaat ggcccgcctg gcattatgcc cagtacatga ccttatggga ctttcctact    3180
tggcagtaca tctacgtatt agtcatcgct attaccatgg tgatgcggtt ttggcagtac    3240
atcaatgggc gtggatagcg gtttgactca cggggatttc caagtctcca ccccattgac    3300
gtcaatggga gtttgttttg gcaccaaaat caacgggact ttccaaaatg tcgtaacaac    3360
tccgccccat tgacgcaaat gggcggtagg cgtgttggcg cgccaa              3406
```

<210> SEQ ID NO 25

```
<211> LENGTH: 634
<212> TYPE: DNA
<213> ORGANISM: Artificial
<220> FEATURE:
<223> OTHER INFORMATION: Synthetic

<400> SEQUENCE: 25
ccggaattcc ggaccatggg ggtgcacgaa tgtcctgcct ggctgtggct tctcctgtcc      60
ctgctgtcgc tccctctggg cctcccagtc ctgggcgccc caccacgcct catctgtgac     120
agccgagtcc tggagaggta cctcttggag gccaaggagg ccgagaatat cacgacgggc     180
tgtgctgaac actgcagctt gaatgagaat atcactgtcc agacaccaa agttaatttc      240 tatgcctgga agaggatgga ggtcgggcag caggccgtag aagtctggca gggcctggcc     300
ctgctgtcgg aagctgtcct gcggggccag gccctgttgg tcaactcttc ccagccgtgg     360
gagcccctgc agctgcatgt ggataaagcc gtcagtggcc ttcgcagcct caccactctg     420
cttcgggctc tgggagccca gaaggaagcc atctcccctc agatgcggc ctcagctgct      480 ccactccgaa caatcactgc tgacactttc cgcaaactct ccgagtcta ctccaatttc      540 ctccggggaa agctgaagct gtacacaggg gaggcctgca ggacagggga cagaggacca     600
ggtcatcacc accatcacca ttgagctcta gagc                                 634

<210> SEQ ID NO 26
<211> LENGTH: 778
<212> TYPE: DNA
<213> ORGANISM: Artificial
<220> FEATURE:
<223> OTHER INFORMATION: Synthetic

<400> SEQUENCE: 26
gaattccggc cgctcgagcg gaccatggag aaagacacac tcctgctatg ggtcctgctt      60
ctctgggttc caggttccac aggtgacatt gtgctgaccc aatctccagc ttctttggct     120
gtatctctag gacagagggc caccatctcc tgcagagcca gcgaaagtgt tgataattat     180
ggctttagtt ttatgaactg gttccagcag aaaccaggac agcccccaa actcctcatc      240 tatgctatat ccaaccgagg gtccggggtc cctgccaggt ttagtggcag tgggtctggg     300
acagacttca gcctcaacat ccatcctgta gaggaggatg atcctgcaat gtatttctgt     360
cagcaaacta aggaggttcc gtggacgttc ggtggaggca ccaagctgga atcaaacgg      420 gctgatgctg caccaactgt atccatcttc ccaccatcca gtgagcagtt aacatctgga     480
ggtgcctcag tcgtgtgctt cttgaacaac ctctacccca aagacatcaa tgtcaagtgg     540
aagattgatg gcagtgaacg acaaaatggc gtcctgaaca gttggactga tcaggacagc     600
aaagacagca cctacagcat gagcagcacc ctcacgttga ccaaggacga gtatgaacga     660
cataacagct atacctgtga ggccactcac aagacatcaa cttcacccat tgtcaagagc     720
ttcaacagga atgagtgtgg accgggccat caccaccatc accattgagc tctagagc      778

<210> SEQ ID NO 27
<211> LENGTH: 1489
<212> TYPE: DNA
<213> ORGANISM: Artificial
<220> FEATURE:
<223> OTHER INFORMATION: Synthetic

<400> SEQUENCE: 27
gaattccgga ccatggggaa cttcgggctc agcttgattt ccttgccct cattttaaaa      60 ggtgtccagt gtgaggtgca cctggtggag tctgggggag acttagtgaa gcctggaggg     120
```

```
tccctgaaac tctcctgtgc agcctctgga ttcactttca gtcactatgg catgtcttgg      180
gttcgccaga ctccagacaa gaggctggag tgggtcgcaa ccattggtag tcgtggtact      240
tacacccact atccagacag tgtgaaggga cgattcacca tctccagaga caatgacaag      300
aacgccctgt acctgcaaat gaacagtctg aagtctgaag acacagccat gtattactgt      360
gcaagaagaa gtgaatttta ttactacggt aatacctact attactctgc tatggactac      420
tggggtcaag agcctcagt caccgtctcc tcagccaaaa cgacaccccc atctgtctat      480
ccactggccc ctggatctgc tgcccaaact aactccatgg tgaccctggg atgcctggtc      540
aagggctatt ccctgagcc agtgacagtg acctggaact ctggggtccct gtccagcggt      600 gtgcacacct tcccagctgt cctgcagtct gacctctaca ctctgagcag ctcagtgact      660
gtcccctcca gcacctggcc cagcgagacc gtcacctgca acgttgccca cccggccagc      720
agcaccaagg tggacaagaa aattgtgccc agggattgtg gttgtaagcc ttgcatatgt      780
acagtcccag aagtatcatc tgtcttcatc ttccccccaa agcccaagga tgtgctcacc      840
attactctga ctcctaaggt cacgtgtgtt gtggtagaca tcagcaagga tgatcccgag      900
gtccagttca gctggtttgt agatgatgtg gaggtgcaca cagctcagac gcaacccgg      960 gaggagcagt tcaacagcac tttccgctca gtcagtgaac ttcccatcat gcaccaggac     1020
tggcccaatg caaggagtt caaatgcagg gtcaacagtg cagctttccc tgcccccatc     1080
gagaaaacca tctccaaaac caaaggcaga ccgaaggctc acaggtgta caccattcca     1140 cctcccaagg agcagatggc caaggataaa gtcagtctga cctgcatgat aacagacttc     1200
ttccctgaag acattactgt ggagtggcag tggaatgggc agccagcgga gaactacaag     1260
aacactcagc ccatcatgaa cacgaatggc tcttacttcg tctacagcaa gctcaatgtg     1320
cagaagagca actgggaggc aggaaatact ttcacctgct ctgtgttaca tgagggcctg     1380
cacaaccacc atactgagaa gagcctctcc cactctcctg gtaaaggacc gggccatcac     1440
caccatcacc attgacgcgg atccgcgagg actagtcctg ctctagagc                 1489
```

<210> SEQ ID NO 28
<211> LENGTH: 2355
<212> TYPE: DNA
<213> ORGANISM: Artificial
<220> FEATURE:
<223> OTHER INFORMATION: Synthetic

<400> SEQUENCE: 28

```
tctagagcac catgcagcgg cttggggcca ccctgctgtg cctgctgctg gcggcggcgg       60
tccccacggc ccccgcgccc gctccgacgg cgacctcggc tccagtcaag cccggcccgg      120
ctctcagcta cccgcaggag gaggccacct caatgagat gttccgcgag gttgaggaac      180
tgatggagga cacgcagcac aaattgcgca gcgcggtgga agagatggag cagaagaag      240 ctgctgctaa agcatcatca gaagtgaacc tggcaaactt acctcccagc tatcacaatg      300
agaccaacac agacacgaag gttggaaata ataccatcca tgtgcaccga gaaattcaca      360
agataaccaa caaccagact ggacaaatgg tcttttcaga gacagttatc acatctgtgg      420
gagacgaaga aggcagaagg agccacgagt gcatcatcga cgaggactgt gggcccagca      480
tgtactgcca gtttgccagc ttccagtaca cctgccagcc atgccggggc cagaggatgc      540
tctgcacccg ggacagtgag tgctgtggag accagctgtg tgtctggggt cactgcacca      600
aaatggccac caggggcagc aatggggacca tctgtgacaa ccagagggac tgccagccgg      660
```

```
ggctgtgctg tgccttccag agaggcctgc tgttccctgt gtgcacaccc ctgcccgtgg      720
agggcgagct tgccatgac cccgccagcc ggcttctgga cctcatcacc tgggagctag       780
agcctgatgg agccttggac cgatgccctt gtgccagtgg cctcctctgc cagccccaca      840
gccacagcct ggtgtatgtg tgcaagccga ccttcgtggg gagccgtgac caagatgggg      900
agatcctgct gcccagagag gtccccgatg agtatgaagt tggcagcttc atggaggagg      960
tgcgccagga gctggaggac ctggagagga gcctgactga agagatggcg ctgggggagc      1020
ctgcggctgc cgccgctgca ctgctgggag gggaagagat ttaggggta ccccggctag       1080 atgactaacg tttaaacccg ctgatcagcc tcgactgtgc cttctagttg ccagccatct      1140
gttgtttgcc cctcccccgt gccttccttg accctggaag gtgccactcc cactgtcctt      1200
tcctaataaa atgaggaaat tgcatcgcat tgtctgagta ggtgtcattc tattctgggg      1260
ggtggggtgg ggcaggacag caaggggag gattgggaag acaatagcag gcatgctggg       1320
gatgcggtgg gctctatggc ggagtactgt cctccgcttc ccacgtggcg agggactgg       1380 ggacccgggc acccgtcctg cccccttcacc ttccagctcc gcctcctccg cgcggacccc     1440
gccccgtccc gacccctccc gggtccccgg cccagccccc tccgggccct cccagcccct     1500 cccttcctt tccgcggccc cgccctctcc tcgcggcgcg agttttggaa agtccccagg      1560
ctccccagca ggcagaagta tccaaagcat ccatctcaat tagtcagcaa ccaggtgtgg     1620
aaagtcccca ggctccccag caggcagaag tatccaaagc atccatctca attagtcagc     1680
aaccatagtc ccgcccctaa ctccgcccat cccgccccta actccgccca gttccgccca     1740
ttctccgccc catggctgac taattttttt tatttatgca gaggccgagg ccgcctctgc     1800
ctctgagcta ttccagaagt agtgaggagg cttttttgga ggccaaggct tttgcaaaaa     1860
gctccgttac ataacttacg gtaaatggcc cgcctggctg accgcccaac gaccccccgcc    1920 cattgacgtc aataatgacg tatgttccca tagtaacgcc aatagggact ttccattgac     1980
gtcaatgggt ggagtattta cggtaaactg cccacttggc agtacatcaa gtgtatcata     2040
tgccaagtac gcccccctatt gacgtcaatg acggtaaatg gcccgcctgg cattatgccc    2100
agtacatgac cttatgggac tttcctactt ggcagtacat ctacgtatta gtcatcgcta     2160
ttaccatggt gatgcggttt tggcagtaca tcaatgggcg tggatagcgg tttgactcac     2220
ggggatttcc aagtctccac cccattgacg tcaatgggag tttgttttgg caccaaaatc     2280
aacgggactt tccaaaatgt cgtaacaact ccgccccatt gacgcaaatg gcggtaggc      2340 gtgttgccgg aattc                                                      2355
```

<210> SEQ ID NO 29
<211> LENGTH: 1413
<212> TYPE: DNA
<213> ORGANISM: Artificial
<220> FEATURE:
<223> OTHER INFORMATION: Synthetic

<400> SEQUENCE: 29

```
atgttcatgc cttcttcttt ttcctacagc tcctgggcaa cgtgctggtt attgtgctgt      60
ctcatcattt tggcaaagaa ttcgcccttc accatgcccc tcaacgtgaa cttcaccaac      120
aggaactatg acctcgacta cgactccgta cagccctatt tcatctgcga cgaggaagag      180
aatttctatc accagcaaca gcagagcgag ctgcagccgc ccgcgcccag tgaggatatc      240
tggaagaaat tcgagctgct tcccaccccg ccctgtccc cgagccgccg ctccgggctc       300
tgctctccat cctatgttgc ggtcgctacg tccttctccc caagggaaga cgatgacggc      360
```

```
ggcggtggca acttctccac cgccgatcag ctggagatga tgaccgagtt acttggagga      420
gacatggtga accagagctt catctgcgat cctgacgacg agaccttcat caagaacatc      480
atcatccagg actgtatgtg gagcggtttc tcagccgctg ccaagctggt ctcggagaag      540
ctggcctcct accaggctgc cgcaaagac agcaccagcc tgagcccgc ccgcgggcac        600 agcgtctgct ccacctccag cctgtacctg caggacctca ccgccgccgc gtccgagtgc      660
attgacccct cagtggtctt tccctacccg ctcaacgaca gcagctcgcc caaatcctgt      720
acctcgtccg attccacggc cttctctcct tcctcggact cgctgctgtc ctccgagtcc      780
tccccacggg ccagccctga gcccctagtg ctgcatgagg agacaccgcc caccaccagc      840
agcgactctg aagaagagca agaagatgag gaagaaattg atgtggtgtc tgtggagaag      900
aggcaaaccc ctgccaagag gtcggagtcg ggctcatctc catcccgagg ccacagcaaa      960
cctccgcaca gcccactggt cctcaagagg tgccacgtct ccactcacca gcacaactac     1020
gccgcacccc cctccacaag gaaggactat ccagctgcca gagggccaa gttggacagt      1080 ggcagggtcc tgaagcagat cagcaacaac cgcaagtgct ccagccccag gtcctcagac     1140
acggaggaaa acgacaagag gcggacacac aacgtcttgg aacgtcagag gaggaacgag     1200
ctgaagcgca gcttttttgc cctgcgtgac cagatccctg aattggaaaa caacgaaaag     1260
gcccccaagg tagtgatcct caaaaaagcc accgcctaca tcctgtccat tcaagcagac     1320
gagcacaagc tcacctctga aaaggactta ttgaggaaac gacgagaaca gttgaaacac     1380
aaactcgaac agcttcgaaa ctctggtgca taa                                  1413

<210> SEQ ID NO 30
<211> LENGTH: 1285
<212> TYPE: DNA
<213> ORGANISM: Artificial
<220> FEATURE:
<223> OTHER INFORMATION: Synthetic

<400> SEQUENCE: 30
gtttaaaccc gctgatcagc ctcgactgtg ccttctagtt gccagccatc tgttgtttgc       60
ccctcccccg tgccttcctt gaccctggaa ggtgccactc ccactgtcct ttcctaataa      120
aatgaggaaa ttgcatcgca ttgtctgagt aggtgtcatt ctattctggg gggtggggtg      180
gggcaggaca gcaaggggga ggattgggaa gacaatagca ggcatgctgg ggatgcggtg      240
ggctctatgg cggagtactg tcctccgctt cccacgtggc ggagggactg gtcctccgct      300
tcccacgtgg cggagggact ggggacccgg gcacccgtcc tgccccttca ccttccagct      360
ccgcctcctc cgcgcggacc ccgccccgtc ccgaccctc ccgggtcccc ggcccagccc       420
cctccgggcc ctcccagccc ctcccccttcc tttccgcggc ccgccctct cctgcgggcg     480 cgagttttgg aaagtcccca ggctccccag caggcagaag tatccaaagc atccatctca      540
attagtcagc aaccaggtgt ggaaagtccc caggctcccc agcaggcaga agtatccaaa      600
gcatccatct caattagtca gcaaccatag tcccgcccct aactccgccc atcccgcccc      660
taactccgcc cagttccgcc cattctccgc cccatggctg actaattttt tttatttatg      720
cagaggccga ggccgcctct gcctctgagc tattccagaa gtagtgagga ggcttttttg      780
gaggccaagg cttttgcaaa aagctccgtt acataactta cggtaaatgg cccgcctggc      840
tgaccgccca acgaccccg cccattgacg tcaataatga cgtatgttcc catagtaacg       900
ccaataggga ctttccattg acgtcaatgg gtggagtatt tacggtaaac tgcccacttg      960
```

| | |
|---|---|
| gcagtacatc aagtgtatca tatgccaagt acgcccccta ttgacgtcaa tgacggtaaa | 1020 |
| tggcccgcct ggcattatgc ccagtacatg accttatggg actttcctac ttggcagtac | 1080 |
| atctacgtat tagtcatcgc tattaccatg gtgatgcggt tttggcagta catcaatggg | 1140 |
| cgtggatagc ggtttgactc acggggattt ccaagtctcc accccattga cgtcaatggg | 1200 |
| agtttgtttt ggcaccaaaa tcaacgggac tttccaaaat gtcgtaacaa ctccgcccca | 1260 |
| ttgacgcaaa tgggcggtag gcgtg | 1285 |

```
<210> SEQ ID NO 31
<211> LENGTH: 1968
<212> TYPE: DNA
<213> ORGANISM: Artificial
<220> FEATURE:
<223> OTHER INFORMATION: Synthetic

<400> SEQUENCE: 31
```

| | |
|---|---|
| gtcgacgtcg gccataccgg aattccggct tcccacgtgg cggagggact ggggacccgg | 60 |
| gcacccgtcc tgccccttca ccttccagct ccgcctcctc cgcgcggacc ccgcccgtc | 120 |
| ccgaccctc ccgggtcccc ggcccagccc cctccgggcc ctcccagccc ctcccttcc | 180 |
| tttccgcggc cccgccctct cctcgcgcg cgagtttcag gcagcgctgc gtcctgctgc | 240 |
| gcacgtgggg taggcgtgta cggtgggagg cctatataag cagagctcgt ttagtgaacc | 300 |
| gtcagatcgc ctggagacgc catccacgct gttttgacct ccatagaaga caccgggacc | 360 |
| gatccagcct ccgcggcccc gcattcgagc tcggtacccg gcccaagctt gggagcttcg | 420 |
| aggggctcgc atctctcctt cacgcgcccg ccgccctacc tgaggccgcc atccacgccg | 480 |
| gttgagtcgc gttctgccgc ctcccgcctg tggtgcctcc tgaactgcgt ccgccgtcta | 540 |
| ggtaagttta aagctcaggt cgagaccggg cctttgtccg cgctcccctt ggagcctacc | 600 |
| tagactcagc cggctctcca cgctttgcct gaccctgctt gctcaactct acgtcttttgt | 660 |
| ttcgtttttct gttctgcgcc gttacagatc caagccaccc caagcttgg gcgggatccc | 720 |
| gaccatggtg agcaagggcg aggagctgtt caccggggtg gtgcccatcc tggtcgagct | 780 |
| ggacggcgac gtaaacggcc acaagttcag cgtgtccggc gagggcgagg gcgatgccac | 840 |
| ctacggcaag ctgacccctga agttcatctg caccaccggc aagctgcccg tgccctggcc | 900 |
| caccctcgtg accaccctga cctacggcgt gcagtgcttc agccgctacc ccgaccacat | 960 |
| gaagcagcac gacttcttca agtccgccat gcccgaaggc tacgtccagg agcgcaccat | 1020 |
| cttcttcaag gacgacggca actacaagac ccgcgccgag gtgaagttcg agggcgacac | 1080 |
| cctggtgaac cgcatcgagc tgaagggcat cgacttcaag gaggacggca acatcctggg | 1140 |
| gcacaagctg gagtacaact acaacagcca caacgtctat atcatggccg acaagcagaa | 1200 |
| gaacggcatc aaggtgaact tcaagatccg ccacaacatc gaggacggca gcgtgcagct | 1260 |
| cgccgaccac taccagcaga acaccccat cggcgacggc ccgtgctgc tgcccgacaa | 1320 |
| ccactacctg agcacccagt ccgccctgag caaagacccc aacgagaagc gcgatcacat | 1380 |
| ggtcctgctg gagttcgtga ccgccgccgg gatcactctc ggcatggacg agctgtacaa | 1440 |
| gtgaccgctc gagcgggctc tagaggttta aacccgctga tcagcctcga ctgtgccttc | 1500 |
| tagttgccag ccatctgttg tttgcccctc ccccgtgcct tccttgaccc tggaaggtgc | 1560 |
| cactcccact gtccttttcct aataaaatga ggaaattgca tcgcattgtc tgagtaggtg | 1620 |
| tcattctatt ctggggggtg gggtgggca ggacagcaag ggggaggatt gggaagacaa | 1680 |
| tagcaggcat gctggggatg cggtgggctc tatggatgca tccaatgcat tggatgcatc | 1740 |

```
ttcccacgtg gcggagggac tggggacccg ggcacccgtc ctgccccttc accttccagc    1800
tccgcctcct ccgcgcggac cccgcccegt cccgacccct cccgggtccc cggcccagcc    1860
ccctccgggc cctcccagcc cctcccettc ctttccgcgg ccccgccctc tcctcgcggc    1920
gcgagtttca ggcagcgctg cgtcctgctg cgcacgtggt tggcgcgc                 1968

<210> SEQ ID NO 32
<211> LENGTH: 72
<212> TYPE: DNA
<213> ORGANISM: Artificial
<220> FEATURE:
<223> OTHER INFORMATION: Synthetic

<400> SEQUENCE: 32
atcgattcta gactagttta attaatttaa atcgattagc taagatctga tcaaattaat    60
taaatttagc ta                                                        72
```